(12) United States Patent
Mesiwala et al.

(10) Patent No.: US 12,427,034 B2
(45) Date of Patent: *Sep. 30, 2025

(54) IMPLANTS FOR SPINAL FIXATION AND OR FUSION

(71) Applicant: SI-Bone Inc., Santa Clara, CA (US)

(72) Inventors: Ali H. Mesiwala, Claremont, CA (US); Mark A. Reiley, Delray Beach, FL (US); Paul M. Sand, Redwood City, CA (US); Bret W. Schneider, San Jose, CA (US); Scott A. Yerby, Montara, CA (US); Christopher I. Shaffrey, Durham, NC (US); Robert K. Eastlack, La Jolla, CA (US); Juan S. Uribe, Paradise Valley, AZ (US); Isador H. Lieberman, Plano, TX (US); Frank M. Phillips, Chicago, IL (US); David W. Polly, Edina, MN (US); Phillip J. Singer, Bowling Green, KY (US); Jeffrey B. Phelps, North Richland Hills, TX (US); Derek P. Lindsey, San Jose, CA (US); Patrick Kahn, Livermore, CA (US); Nikolas F. Kerr, Milpitas, CA (US); Francois Follini, Austin, TX (US)

(73) Assignee: SI-Bone Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,820

(22) Filed: May 3, 2023

(65) Prior Publication Data
US 2023/0270559 A1  Aug. 31, 2023

Related U.S. Application Data

(63) Continuation of application No. 17/649,265, filed on Jan. 28, 2022, now Pat. No. 11,678,997, which is a
(Continued)

(51) Int. Cl.
*A61B 17/70* (2006.01)
*A61F 2/28* (2006.01)
(Continued)

(52) U.S. Cl.
CPC ........ *A61F 2/4455* (2013.01); *A61B 17/7055* (2013.01); *A61F 2/28* (2013.01);
(Continued)

(58) Field of Classification Search
CPC ...... A61F 2/4455; A61F 2/28; A61F 2/30771; A61F 2/442; A61F 2/4611;
(Continued)

(56) References Cited

U.S. PATENT DOCUMENTS

| 1,951,278 A | 3/1934 | Ericsson |
| 2,136,471 A | 11/1938 | Schneider |

(Continued)

FOREIGN PATENT DOCUMENTS

| CN | 1128944 A | 8/1996 |
| CN | 1190882 A | 8/1998 |

(Continued)

OTHER PUBLICATIONS

Stuart et al.; U.S. Appl. No. 18/356,880 entitled "Sacro-iliac join stabilizing implants and methods of implantation," filed Jul. 21, 2023.
(Continued)

*Primary Examiner* — Bruce E Snow
(74) *Attorney, Agent, or Firm* — Shay Glenn LLP

(57) ABSTRACT

Bone implants, including methods of use and assembly. The bone implants, which are optionally composite implants, generally include a distal anchoring region and a growth region that is proximal to the distal anchoring region. The distal anchoring region can have one or more distal surface features that adapt the distal anchoring region for anchoring
(Continued)

into iliac bone. The growth region can have one or more growth features that adapt the growth region to facilitate at least one of bony on-growth, in-growth, or through-growth. The implants may be positioned along a posterior sacral alar-iliac ("SAI") trajectory. The implants may be coupled to one or more bone stabilizing constructs, such as rod elements thereof.

12 Claims, 51 Drawing Sheets

Related U.S. Application Data continuation of application No. 16/874,149, filed on May 14, 2020, now Pat. No. 11,234,830, which is a continuation of application No. PCT/US2020/018402, filed on Feb. 14, 2020, which is a continuation of application No. 16/276,430, filed on Feb. 14, 2019, now Pat. No. 11,369,419.

(60) Provisional application No. 62/933,250, filed on Nov. 8, 2019, provisional application No. 62/859,646, filed on Jun. 10, 2019.

(51) Int. Cl.
　　*A61F 2/30*　　　(2006.01)
　　*A61F 2/44*　　　(2006.01)
　　*A61B 17/02*　　　(2006.01)
　　*A61F 2/46*　　　(2006.01)

(52) U.S. Cl.
　　CPC .......... *A61F 2/30771* (2013.01); *A61F 2/442* (2013.01); *A61B 17/0218* (2013.01); *A61B 17/025* (2013.01); *A61B 2017/0256* (2013.01); *A61F 2002/2835* (2013.01); *A61F 2002/3085* (2013.01); *A61F 2/4611* (2013.01)

(58) Field of Classification Search
　　CPC ..... A61F 2002/2835; A61F 2002/3085; A61B 17/7055; A61B 17/0218; A61B 17/025; A61B 2017/0256
　　See application file for complete search history.

(56) References Cited

U.S. PATENT DOCUMENTS

| | | |
|---|---|---|
| 2,243,717 A | 5/1941 | Moreira |
| 2,414,882 A | 1/1947 | Longfellow |
| 2,562,419 A | 7/1951 | Ferris |
| 2,675,801 A | 4/1954 | Bambara et al. |
| 2,697,433 A | 12/1954 | Zehnder |
| 3,076,453 A | 2/1963 | Tronzo |
| 3,506,982 A | 4/1970 | Steffee |
| 3,694,821 A | 10/1972 | Moritz |
| 3,709,218 A | 1/1973 | Halloran |
| 3,744,488 A | 7/1973 | Cox |
| 4,059,115 A | 11/1977 | Jumashev et al. |
| 4,156,943 A | 6/1979 | Collier |
| 4,197,645 A | 4/1980 | Scheicher |
| 4,292,964 A | 10/1981 | Ulrich |
| 4,341,206 A | 7/1982 | Perrett et al. |
| 4,344,190 A | 8/1982 | Lee et al. |
| 4,399,813 A | 8/1983 | Barber |
| 4,423,721 A | 1/1984 | Otte et al. |
| 4,475,545 A | 10/1984 | Ender |
| 4,501,269 A | 2/1985 | Bagby |
| 4,569,338 A | 2/1986 | Edwards |
| 4,612,918 A | 9/1986 | Slocum |
| 4,622,959 A | 11/1986 | Marcus |
| 4,630,601 A | 12/1986 | Harder et al. |
| 4,638,799 A | 1/1987 | Moore |
| 4,657,550 A | 4/1987 | Daher |
| 4,743,256 A | 5/1988 | Brantigan |
| 4,773,402 A | 9/1988 | Asher et al. |
| 4,787,378 A | 11/1988 | Sodhi |
| 4,790,303 A | 12/1988 | Steffee |
| 4,834,757 A | 5/1989 | Brantigan |
| 4,846,162 A | 7/1989 | Moehring |
| 4,877,019 A | 10/1989 | Vives |
| 4,878,915 A | 11/1989 | Brantigan |
| 4,898,186 A | 2/1990 | Ikada et al. |
| 4,904,261 A | 2/1990 | Dove et al. |
| 4,950,270 A | 8/1990 | Bowman et al. |
| 4,961,740 A | 10/1990 | Ray et al. |
| 4,969,888 A | 11/1990 | Scholten et al. |
| 4,981,481 A | 1/1991 | Kranz et al. |
| 5,034,011 A | 7/1991 | Howland |
| 5,034,013 A | 7/1991 | Kyle et al. |
| 5,035,697 A | 7/1991 | Frigg |
| 5,041,118 A | 8/1991 | Wasilewski |
| 5,053,035 A | 10/1991 | McLaren |
| 5,059,193 A | 10/1991 | Kuslich |
| 5,066,296 A | 11/1991 | Chapman et al. |
| 5,098,434 A | 3/1992 | Serbousek |
| 5,102,414 A | 4/1992 | Kirsch |
| 5,108,397 A | 4/1992 | White |
| 5,122,141 A | 6/1992 | Simpson et al. |
| 5,139,498 A | 8/1992 | Astudillo Ley |
| 5,139,500 A | 8/1992 | Schwartz |
| 5,147,367 A | 9/1992 | Ellis |
| 5,147,402 A | 9/1992 | Bohler et al. |
| 5,190,551 A | 3/1993 | Chin et al. |
| 5,197,961 A | 3/1993 | Castle |
| 5,242,444 A | 9/1993 | MacMillan |
| 5,298,254 A | 3/1994 | Prewett et al. |
| 5,334,205 A | 8/1994 | Cain |
| 5,380,325 A | 1/1995 | Lahille et al. |
| 5,390,683 A | 2/1995 | Pisharodi |
| 5,433,718 A | 7/1995 | Brinker |
| 5,443,466 A | 8/1995 | Shah |
| 5,458,638 A | 10/1995 | Kuslich et al. |
| 5,470,334 A | 11/1995 | Ross et al. |
| 5,480,402 A | 1/1996 | Kim |
| 5,569,249 A | 10/1996 | James et al. |
| 5,591,235 A | 1/1997 | Kuslich |
| 5,593,409 A | 1/1997 | Michelson |
| 5,607,424 A | 3/1997 | Tropiano |
| 5,609,635 A | 3/1997 | Michelson |
| 5,609,636 A | 3/1997 | Kohrs et al. |
| 5,626,616 A | 5/1997 | Speece |
| 5,643,264 A | 7/1997 | Sherman et al. |
| 5,645,599 A | 7/1997 | Samani |
| 5,658,337 A | 8/1997 | Kohrs et al. |
| 5,667,510 A | 9/1997 | Combs |
| 5,669,909 A | 9/1997 | Zdeblick et al. |
| 5,672,178 A | 9/1997 | Petersen |
| 5,683,391 A | 11/1997 | Boyd |
| 5,709,683 A | 1/1998 | Bagby |
| 5,713,904 A | 2/1998 | Errico et al. |
| 5,716,358 A | 2/1998 | Ochoa et al. |
| 5,725,581 A | 3/1998 | Brånemark |
| 5,743,912 A | 4/1998 | LaHille et al. |
| 5,759,035 A | 6/1998 | Ricci |
| 5,766,174 A | 6/1998 | Perry |
| 5,766,252 A | 6/1998 | Henry et al. |
| 5,766,261 A | 6/1998 | Neal et al. |
| 5,788,699 A | 8/1998 | Bobst et al. |
| 5,800,440 A | 9/1998 | Stead |
| 5,868,749 A | 2/1999 | Reed |
| 5,897,556 A | 4/1999 | Drewry et al. |
| 5,928,239 A | 7/1999 | Mirza |
| 5,941,885 A | 8/1999 | Jackson |
| 5,961,522 A | 10/1999 | Mehdizadeh |
| 5,961,554 A | 10/1999 | Janson et al. |
| 6,010,507 A | 1/2000 | Rudloff |
| 6,015,409 A | 1/2000 | Jackson |
| 6,030,162 A | 2/2000 | Huebner et al. |
| 6,053,916 A | 4/2000 | Moore |
| 6,056,749 A | 5/2000 | Kuslich |
| 6,066,175 A | 5/2000 | Henderson et al. |

(56) References Cited

U.S. PATENT DOCUMENTS

| | | |
|---|---|---|
| 6,086,589 A | 7/2000 | Kuslich et al. |
| 6,096,080 A | 8/2000 | Nicholson et al. |
| 6,120,292 A | 9/2000 | Buser et al. |
| 6,120,504 A | 9/2000 | Brumback et al. |
| 6,143,031 A | 11/2000 | Knothe et al. |
| 6,197,062 B1 | 3/2001 | Fenlin |
| 6,206,924 B1 | 3/2001 | Timm |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,264,657 B1 | 7/2001 | Urbahns et al. |
| 6,270,528 B1 | 8/2001 | McKay |
| 6,287,343 B1 | 9/2001 | Kuslich et al. |
| 6,302,885 B1 | 10/2001 | Essiger |
| 6,302,914 B1 | 10/2001 | Michelson |
| 6,306,140 B1 | 10/2001 | Siddiqui |
| 6,319,253 B1 | 11/2001 | Ackeret et al. |
| 6,406,498 B1 | 6/2002 | Tormala et al. |
| 6,409,768 B1 | 6/2002 | Tepic et al. |
| 6,436,139 B1 | 8/2002 | Shapiro et al. |
| 6,451,020 B1 | 9/2002 | Zucherman et al. |
| 6,471,707 B1 | 10/2002 | Miller et al. |
| 6,485,518 B1 | 11/2002 | Cornwall et al. |
| 6,497,707 B1 | 12/2002 | Bowman et al. |
| 6,517,541 B1 | 2/2003 | Sesic |
| 6,520,969 B2 | 2/2003 | Lambrecht et al. |
| 6,524,314 B1 | 2/2003 | Dean et al. |
| 6,527,775 B1 | 3/2003 | Warburton |
| 6,556,857 B1 | 4/2003 | Estes et al. |
| 6,558,386 B1 | 5/2003 | Cragg |
| 6,565,566 B1 | 5/2003 | Wagner et al. |
| 6,575,899 B1 | 6/2003 | Foley et al. |
| 6,575,991 B1 | 6/2003 | Chesbrough et al. |
| 6,579,293 B1 | 6/2003 | Chandran |
| 6,582,431 B1 | 6/2003 | Ray |
| 6,582,467 B1 | 6/2003 | Teitelbaum et al. |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,607,530 B1 | 8/2003 | Carl et al. |
| 6,620,163 B1 | 9/2003 | Michelson |
| 6,635,059 B2 | 10/2003 | Randall et al. |
| 6,666,868 B2 | 12/2003 | Fallin |
| 6,669,529 B1 | 12/2003 | Scaries |
| 6,673,075 B2 | 1/2004 | Santilli |
| 6,692,501 B2 | 2/2004 | Michelson |
| 6,712,852 B1 | 3/2004 | Chung et al. |
| 6,723,099 B1 | 4/2004 | Goshert |
| 6,723,100 B2 | 4/2004 | Biedermann et al. |
| 6,740,118 B2 | 5/2004 | Eisermann et al. |
| 6,743,257 B2 | 6/2004 | Castro |
| D493,533 S | 7/2004 | Blain |
| 6,793,656 B1 | 9/2004 | Mathews |
| 6,827,740 B1 | 12/2004 | Michelson |
| 6,984,235 B2 | 1/2006 | Huebner |
| 6,989,033 B1 | 1/2006 | Schmidt |
| 6,991,461 B2 | 1/2006 | Gittleman |
| 6,993,406 B1 | 1/2006 | Cesarano et al. |
| 7,018,416 B2 | 3/2006 | Hanson et al. |
| 7,118,579 B2 | 10/2006 | Michelson |
| 7,147,666 B1 | 12/2006 | Grisoni |
| 7,175,663 B1 | 2/2007 | Stone |
| 7,211,085 B2 | 5/2007 | Michelson |
| 7,223,269 B2 | 5/2007 | Chappuis |
| 7,300,439 B2 | 11/2007 | May |
| 7,314,488 B2 | 1/2008 | Reiley |
| 7,335,205 B2 | 2/2008 | Aeschlimann et al. |
| 7,338,500 B2 | 3/2008 | Chappuis |
| 7,396,365 B2 | 7/2008 | Michelson |
| 7,452,359 B1 | 11/2008 | Michelson |
| 7,452,369 B2 | 11/2008 | Barry |
| 7,481,831 B2 | 1/2009 | Bonutti |
| 7,527,649 B1 | 5/2009 | Blain |
| 7,534,254 B1 | 5/2009 | Michelson |
| 7,537,616 B1 | 5/2009 | Branch et al. |
| 7,569,054 B2 | 8/2009 | Michelson |
| 7,569,059 B2 | 8/2009 | Cerundolo |
| 7,601,155 B2 | 10/2009 | Petersen |
| 7,608,097 B2 | 10/2009 | Kyle |
| 7,608,098 B1 | 10/2009 | Stone et al. |
| 7,648,509 B2 | 1/2010 | Stark |
| 7,686,805 B2 | 3/2010 | Michelson |
| 7,699,852 B2 | 4/2010 | Frankel et al. |
| 7,708,761 B2 | 5/2010 | Petersen |
| 7,727,235 B2 | 6/2010 | Contiliano et al. |
| 7,758,646 B2 | 7/2010 | Khandkar et al. |
| 7,780,704 B2 | 8/2010 | Markworth et al. |
| 7,846,162 B2 | 12/2010 | Nelson et al. |
| 7,850,732 B2 | 12/2010 | Heinz |
| 7,857,832 B2 | 12/2010 | Culbert et al. |
| 7,887,565 B2 | 2/2011 | Michelson |
| 7,892,265 B2 | 2/2011 | Perez-Cruet et al. |
| 7,901,439 B2 | 3/2011 | Horton |
| 7,909,832 B2 | 3/2011 | Michelson |
| 7,922,765 B2 | 4/2011 | Reiley |
| 7,942,879 B2 | 5/2011 | Christie et al. |
| 7,951,176 B2 | 5/2011 | Grady et al. |
| 8,052,728 B2 | 11/2011 | Hestad |
| 8,062,365 B2 | 11/2011 | Schwab |
| 8,066,705 B2 | 11/2011 | Michelson |
| 8,066,709 B2 | 11/2011 | Michelson |
| 8,092,505 B2 | 1/2012 | Sommers |
| 8,142,481 B2 | 3/2012 | Warnick |
| 8,202,305 B2 | 6/2012 | Reiley |
| 8,221,499 B2 | 7/2012 | Lazzara et al. |
| 8,257,398 B2 | 9/2012 | Jackson |
| 8,268,099 B2 | 9/2012 | O'Neill et al. |
| 8,308,779 B2 | 11/2012 | Reiley |
| 8,308,783 B2 | 11/2012 | Morris et al. |
| 8,317,862 B2 | 11/2012 | Troger et al. |
| 8,348,950 B2 | 1/2013 | Assell et al. |
| 8,350,186 B2 | 1/2013 | Jones et al. |
| 8,353,932 B2 | 1/2013 | Jackson |
| 8,388,667 B2 | 3/2013 | Reiley et al. |
| 8,394,129 B2 | 3/2013 | Lopez |
| 8,398,635 B2 | 3/2013 | Vaidya |
| 8,398,682 B2 | 3/2013 | Jackson et al. |
| 8,414,648 B2 | 4/2013 | Reiley |
| 8,425,570 B2 | 4/2013 | Reiley |
| 8,430,930 B2 | 4/2013 | Hunt |
| 8,444,693 B2 | 5/2013 | Reiley |
| 8,449,585 B2 | 5/2013 | Wallenstein et al. |
| 8,467,851 B2 | 6/2013 | Mire et al. |
| 8,470,004 B2 | 6/2013 | Reiley |
| 8,475,505 B2 | 7/2013 | Nebosky et al. |
| 8,529,608 B2 | 9/2013 | Terrill et al. |
| 8,597,299 B2 | 12/2013 | Farr et al. |
| 8,608,802 B2 | 12/2013 | Bagga et al. |
| D697,209 S | 1/2014 | Walthall et al. |
| 8,641,737 B2 | 2/2014 | Matthis et al. |
| 8,641,766 B2 | 2/2014 | Donner et al. |
| 8,663,298 B2 | 3/2014 | Keyer et al. |
| 8,663,332 B1 | 3/2014 | To et al. |
| 8,672,986 B2 | 3/2014 | Klaus et al. |
| 8,734,462 B2 | 5/2014 | Reiley et al. |
| 8,778,026 B2 | 7/2014 | Mauldin |
| 8,840,623 B2 | 9/2014 | Reiley |
| 8,840,651 B2 | 9/2014 | Reiley |
| 8,845,693 B2 | 9/2014 | Smith et al. |
| 8,858,601 B2 | 10/2014 | Reiley |
| 8,888,827 B2 | 11/2014 | Harper et al. |
| 8,894,685 B2 | 11/2014 | Mickiewicz et al. |
| 8,920,477 B2 | 12/2014 | Reiley |
| 8,926,670 B2 | 1/2015 | Jackson |
| 8,936,623 B2 | 1/2015 | Jackson |
| 8,945,190 B2 | 2/2015 | Culbert et al. |
| 8,945,193 B2 | 2/2015 | Kirschman |
| 8,951,254 B2 | 2/2015 | Mayer et al. |
| 8,951,295 B2 | 2/2015 | Matityahu et al. |
| 8,961,571 B2 | 2/2015 | Lee et al. |
| 8,979,911 B2 | 3/2015 | Martineau et al. |
| 8,986,348 B2 | 3/2015 | Reiley |

(56) References Cited

U.S. PATENT DOCUMENTS

| | | |
|---|---|---|
| RE45,484 E | 4/2015 | Foley et al. |
| 9,039,743 B2 | 5/2015 | Reiley |
| 9,044,321 B2 | 6/2015 | Mauldin et al. |
| 9,060,876 B1 | 6/2015 | To et al. |
| 9,089,371 B1 | 7/2015 | Faulhaber |
| D738,498 S | 9/2015 | Frey et al. |
| 9,131,955 B2 | 9/2015 | Swofford |
| 9,149,286 B1 | 10/2015 | Greenhalgh et al. |
| 9,173,692 B1 | 11/2015 | Kaloostian |
| 9,198,676 B2 | 12/2015 | Pilgeram et al. |
| 9,220,535 B2 | 12/2015 | Röbling et al. |
| 9,314,286 B2 | 4/2016 | Bottlang et al. |
| 9,314,348 B2 | 4/2016 | Emstad |
| 9,358,047 B2 | 6/2016 | Mishra et al. |
| 9,358,057 B1 | 6/2016 | Whipple et al. |
| 9,375,243 B1 | 6/2016 | Vestgaarden |
| 9,375,323 B2 | 6/2016 | Reiley |
| 9,445,852 B2 | 9/2016 | Sweeney |
| 9,451,999 B2 | 9/2016 | Simpson et al. |
| 9,452,065 B1 | 9/2016 | Lawson |
| 9,486,264 B2 | 11/2016 | Reiley et al. |
| 9,492,201 B2 | 11/2016 | Reiley |
| 9,498,264 B2 | 11/2016 | Harshman et al. |
| 9,510,872 B2 | 12/2016 | Donner et al. |
| 9,517,095 B2 | 12/2016 | Vaidya |
| 9,526,548 B2 | 12/2016 | Asfora |
| 9,554,909 B2 | 1/2017 | Donner |
| 9,561,063 B2 | 2/2017 | Reiley |
| 9,566,100 B2 | 2/2017 | Asfora |
| 9,603,613 B2 | 3/2017 | Schoenefeld et al. |
| 9,603,644 B2 * | 3/2017 | Sweeney .............. A61B 17/863 |
| D783,821 S | 4/2017 | Folsom et al. |
| 9,615,856 B2 | 4/2017 | Arnett et al. |
| 9,622,783 B2 | 4/2017 | Reiley et al. |
| 9,655,656 B2 | 5/2017 | Whipple |
| 9,662,124 B2 | 5/2017 | Assell et al. |
| 9,662,128 B2 | 5/2017 | Reiley |
| 9,662,157 B2 | 5/2017 | Schneider et al. |
| 9,662,158 B2 | 5/2017 | Reiley |
| 9,675,394 B2 | 6/2017 | Reiley |
| 9,743,969 B2 | 8/2017 | Reiley |
| 9,757,154 B2 | 9/2017 | Donner et al. |
| 9,763,695 B2 | 9/2017 | Mirda |
| 9,763,802 B2 | 9/2017 | Baynham |
| 9,775,648 B2 | 10/2017 | Greenberg et al. |
| 9,788,866 B2 | 10/2017 | Jackson |
| 9,808,292 B2 | 11/2017 | Jackson |
| 9,808,298 B2 | 11/2017 | Stroncek et al. |
| 9,808,299 B2 | 11/2017 | Goel et al. |
| 9,808,337 B2 | 11/2017 | Housman et al. |
| 9,820,789 B2 | 11/2017 | Reiley |
| 9,826,986 B2 | 11/2017 | Donner et al. |
| 9,833,321 B2 | 12/2017 | Rindal et al. |
| 9,839,448 B2 | 12/2017 | Reckling et al. |
| 9,848,889 B2 | 12/2017 | Taylor et al. |
| 9,848,892 B2 | 12/2017 | Biedermann et al. |
| 9,883,874 B1 | 2/2018 | Vestgaarden |
| 9,888,911 B2 | 2/2018 | Siegal |
| 9,931,141 B2 * | 4/2018 | Jimenez .............. A61B 17/863 |
| 9,936,983 B2 | 4/2018 | Mesiwala et al. |
| 9,949,776 B2 | 4/2018 | Mobasser et al. |
| 9,949,843 B2 | 4/2018 | Reiley et al. |
| D816,843 S | 5/2018 | Lewis |
| 9,956,013 B2 | 5/2018 | Reiley et al. |
| 9,993,276 B2 | 6/2018 | Russell |
| 9,993,277 B2 | 6/2018 | Krinke et al. |
| 9,999,449 B2 | 6/2018 | Bonutti |
| 10,004,547 B2 | 6/2018 | Reiley |
| 10,034,676 B2 | 7/2018 | Donner |
| 10,058,430 B2 | 8/2018 | Donner et al. |
| 10,064,670 B2 | 9/2018 | Mootien et al. |
| D831,828 S | 10/2018 | Horton et al. |
| 10,166,022 B2 | 1/2019 | Early et al. |
| 10,166,033 B2 | 1/2019 | Reiley et al. |
| 10,179,014 B1 | 1/2019 | Menmuir et al. |
| 10,188,403 B2 | 1/2019 | Mirochinik et al. |
| 10,188,432 B2 | 1/2019 | Jackson et al. |
| 10,188,442 B2 | 1/2019 | Mazel |
| 10,194,951 B2 | 2/2019 | Jackson et al. |
| 10,194,962 B2 | 2/2019 | Schneider et al. |
| 10,201,427 B2 | 2/2019 | Mauldin et al. |
| 10,219,841 B1 | 3/2019 | Compton et al. |
| 10,219,885 B2 | 3/2019 | Mamo et al. |
| D846,977 S | 4/2019 | Williams et al. |
| D847,336 S | 4/2019 | Asfora et al. |
| 10,245,044 B2 | 4/2019 | Petersen |
| 10,245,076 B2 | 4/2019 | Fitzpatrick |
| 10,245,087 B2 | 4/2019 | Donner et al. |
| 10,258,380 B2 | 4/2019 | Sinha |
| 10,258,393 B2 | 4/2019 | Caploon et al. |
| 10,258,394 B2 | 4/2019 | Harshman et al. |
| 10,271,882 B2 | 4/2019 | Biedermann et al. |
| D847,994 S | 5/2019 | Asfora et al. |
| 10,278,737 B2 | 5/2019 | Smith |
| 10,285,745 B2 | 5/2019 | Cummins et al. |
| 10,292,778 B2 | 5/2019 | Kostrzewski et al. |
| D850,616 S | 6/2019 | Asfora et al. |
| 10,314,631 B2 | 6/2019 | Gonzalez Blohm et al. |
| 10,321,937 B2 | 6/2019 | Cormier et al. |
| 10,321,945 B2 | 6/2019 | Schifano et al. |
| 10,335,200 B2 | 7/2019 | Jackson |
| 10,335,202 B2 | 7/2019 | Ziolo et al. |
| 10,335,204 B2 | 7/2019 | Matthis et al. |
| 10,335,206 B2 | 7/2019 | Nichols et al. |
| 10,335,211 B2 | 7/2019 | Chan et al. |
| 10,335,212 B2 | 7/2019 | Paolino et al. |
| 10,335,216 B2 | 7/2019 | Mari et al. |
| 10,335,217 B2 | 7/2019 | Lindner |
| 10,342,586 B2 | 7/2019 | Schneider |
| 10,349,983 B2 | 7/2019 | Purcell et al. |
| 10,349,986 B2 | 7/2019 | Wall et al. |
| 10,357,287 B2 | 7/2019 | Schlaepfer et al. |
| 10,363,070 B2 | 7/2019 | Jackson et al. |
| 10,363,073 B2 | 7/2019 | Raina et al. |
| 10,363,140 B2 | 7/2019 | Mauldin et al. |
| 10,363,143 B2 | 7/2019 | Neubardt |
| 10,368,919 B2 | 8/2019 | Pham et al. |
| 10,413,332 B2 | 9/2019 | Schumacher et al. |
| 10,426,539 B2 | 10/2019 | Schifano et al. |
| 10,433,880 B2 | 10/2019 | Donner et al. |
| 10,441,319 B2 | 10/2019 | Jackson et al. |
| 10,456,268 B2 | 10/2019 | Mercier et al. |
| 10,463,402 B2 | 11/2019 | Biester et al. |
| 10,478,227 B2 | 11/2019 | Leff et al. |
| 10,485,596 B2 | 11/2019 | Koller et al. |
| 10,492,841 B2 | 12/2019 | Hartdegen et al. |
| 10,492,921 B2 | 12/2019 | McShane, III et al. |
| 10,517,734 B2 | 12/2019 | Donner |
| 10,531,898 B2 | 1/2020 | Boulot |
| 10,531,904 B2 | 1/2020 | Kolb |
| 10,537,340 B2 | 1/2020 | Mirochinik et al. |
| D875,931 S | 2/2020 | Asfora et al. |
| 10,555,758 B2 | 2/2020 | Magee et al. |
| 10,588,676 B2 | 3/2020 | Kang et al. |
| 10,588,677 B2 | 3/2020 | McDonnell |
| 10,595,917 B2 | 3/2020 | Loftus |
| 10,596,003 B2 | 3/2020 | Donner et al. |
| 10,603,054 B2 | 3/2020 | Asfora et al. |
| 10,603,055 B2 | 3/2020 | Donner et al. |
| 10,603,087 B2 | 3/2020 | Brenzel et al. |
| 10,603,176 B2 | 3/2020 | Arnold et al. |
| 10,610,275 B2 | 4/2020 | Brianza |
| 10,610,276 B2 | 4/2020 | Lutz |
| 10,610,370 B2 | 4/2020 | Baynham |
| 10,610,728 B2 | 4/2020 | Fano et al. |
| 10,617,453 B2 | 4/2020 | Beckett et al. |
| 10,653,454 B2 | 5/2020 | Frey et al. |
| 10,653,455 B2 | 5/2020 | Lehman et al. |
| 10,653,544 B2 | 5/2020 | Forsell |
| 10,660,657 B2 | 5/2020 | Slobitker et al. |
| 10,660,679 B2 | 5/2020 | Kang et al. |
| 10,660,684 B2 | 5/2020 | Kang et al. |
| 10,667,923 B2 | 6/2020 | Sullivan et al. |
| 10,682,131 B2 | 6/2020 | Fallin et al. |

(56) References Cited

U.S. PATENT DOCUMENTS

| | | |
|---|---|---|
| 10,682,150 B2 | 6/2020 | Stark |
| 10,682,437 B2 | 6/2020 | Roth |
| 10,709,570 B2 | 7/2020 | Stauffer et al. |
| 10,711,334 B2 | 7/2020 | Patel et al. |
| 10,729,475 B2 | 8/2020 | Childs |
| 10,729,482 B2 | 8/2020 | Fantigrossi et al. |
| 10,743,995 B2 | 8/2020 | Fallin et al. |
| D895,111 S | 9/2020 | Frey et al. |
| 10,758,283 B2 | 9/2020 | Frey et al. |
| 10,758,285 B2 | 9/2020 | Geist et al. |
| 10,792,074 B2 | 10/2020 | Jackson |
| 10,799,277 B2 | 10/2020 | Kulper et al. |
| 10,799,367 B2 | 10/2020 | Vrionis et al. |
| 10,806,597 B2 | 10/2020 | Soumac et al. |
| 10,842,511 B2 | 11/2020 | Patel et al. |
| 10,842,634 B2 | 11/2020 | Pasini et al. |
| D904,615 S | 12/2020 | Asfora et al. |
| D905,232 S | 12/2020 | Schifano et al. |
| 10,856,922 B2 | 12/2020 | Loke et al. |
| 10,864,029 B2 | 12/2020 | Redmond et al. |
| 10,898,333 B2 | 1/2021 | Cordaro |
| 10,905,472 B2 | 2/2021 | Mari et al. |
| 10,912,654 B2 | 2/2021 | Scheland |
| 10,932,838 B2 | 3/2021 | Mehl et al. |
| 10,939,944 B2 | 3/2021 | Wapner et al. |
| 10,959,758 B2 | 3/2021 | Mesiwala et al. |
| 10,959,830 B2 | 3/2021 | Williams et al. |
| 10,987,142 B2 | 4/2021 | Poelstra et al. |
| 10,993,754 B2 | 5/2021 | Kuntz et al. |
| 10,993,757 B2 | 5/2021 | Schifano et al. |
| 11,006,985 B2 | 5/2021 | Caploon et al. |
| D921,898 S | 6/2021 | Schifano et al. |
| D922,568 S | 6/2021 | Schifano et al. |
| 11,033,309 B2 | 6/2021 | Zadeh |
| 11,051,856 B2 | 7/2021 | Jackson |
| 11,052,229 B2 | 7/2021 | Althoff et al. |
| 11,058,443 B2 | 7/2021 | Siccardi et al. |
| 11,071,573 B2 | 7/2021 | Schneider et al. |
| 11,116,519 B2 | 9/2021 | Sand et al. |
| 11,116,557 B2 | 9/2021 | Zander et al. |
| 11,147,591 B2 | 10/2021 | Jackson |
| 11,147,597 B2 | 10/2021 | Jackson |
| 11,147,688 B2 | 10/2021 | Reckling et al. |
| D935,025 S | 11/2021 | Schifano et al. |
| 11,166,821 B2 | 11/2021 | Sazy |
| 11,172,939 B2 | 11/2021 | Donner et al. |
| 11,224,467 B2 | 1/2022 | Peterson et al. |
| 11,234,830 B2 * | 2/2022 | Mesiwala ............ A61F 2/30988 |
| 11,259,854 B2 | 3/2022 | Thornes et al. |
| 11,266,767 B2 | 3/2022 | Roth et al. |
| 11,273,043 B1 | 3/2022 | Abbasi |
| 11,284,798 B2 | 3/2022 | Donner et al. |
| 11,284,887 B2 | 3/2022 | Hartdegen et al. |
| 11,291,485 B2 | 4/2022 | Mauldin et al. |
| 11,298,747 B2 | 4/2022 | Klein et al. |
| D951,455 S | 5/2022 | Ginn |
| 11,318,020 B2 | 5/2022 | Bohl |
| 11,331,123 B2 | 5/2022 | Ballard et al. |
| 11,337,821 B2 | 5/2022 | Mauldin et al. |
| 11,369,419 B2 | 6/2022 | Mesiwala et al. |
| 11,419,653 B2 | 8/2022 | Castro |
| 11,419,654 B2 | 8/2022 | Castro |
| 11,446,069 B2 | 9/2022 | Mauldin et al. |
| 11,452,548 B2 | 9/2022 | Harshman et al. |
| 11,471,286 B2 | 10/2022 | Mauldin et al. |
| 11,478,287 B2 | 10/2022 | Mauldin et al. |
| 11,510,801 B2 | 11/2022 | Archbold |
| D972,137 S | 12/2022 | Schifano et al. |
| 11,517,361 B2 | 12/2022 | Major et al. |
| 11,571,245 B2 | 2/2023 | Stuart et al. |
| 11,580,268 B2 | 2/2023 | Suddaby |
| 11,607,251 B2 | 3/2023 | Albert et al. |
| 11,607,256 B1 | 3/2023 | Folsom et al. |
| 11,633,292 B2 | 4/2023 | Reiley |
| 11,672,570 B2 | 6/2023 | Stuart et al. |
| 11,672,664 B2 | 6/2023 | Mauldin et al. |
| 11,678,997 B2 * | 6/2023 | Mesiwala ............... A61F 2/442 623/17.16 |
| 11,684,378 B2 | 6/2023 | Reiley et al. |
| 11,737,884 B2 | 8/2023 | Vestgaarden |
| 11,806,197 B2 | 11/2023 | Frey et al. |
| 11,850,156 B2 | 12/2023 | Mauldin et al. |
| 11,883,296 B2 | 1/2024 | Morgenstern Lopez et al. |
| 12,053,208 B2 | 8/2024 | Vitale et al. |
| 2001/0012942 A1 | 8/2001 | Estes et al. |
| 2001/0046518 A1 | 11/2001 | Sawhney |
| 2001/0047207 A1 | 11/2001 | Michelson |
| 2001/0049529 A1 | 12/2001 | Cachia et al. |
| 2002/0019637 A1 | 2/2002 | Frey et al. |
| 2002/0029043 A1 | 3/2002 | Ahrens et al. |
| 2002/0038123 A1 | 3/2002 | Visotsky et al. |
| 2002/0049497 A1 | 4/2002 | Mason |
| 2002/0077641 A1 | 6/2002 | Michelson |
| 2002/0082598 A1 | 6/2002 | Teitelbaum |
| 2002/0120275 A1 | 8/2002 | Schmieding et al. |
| 2002/0120335 A1 | 8/2002 | Angelucci et al. |
| 2002/0128652 A1 | 9/2002 | Ferree |
| 2002/0143334 A1 | 10/2002 | von Hoffmann et al. |
| 2002/0143335 A1 | 10/2002 | von Hoffmann et al. |
| 2002/0151903 A1 | 10/2002 | Takei et al. |
| 2002/0169507 A1 | 11/2002 | Malone |
| 2002/0183858 A1 | 12/2002 | Contiliano et al. |
| 2002/0198527 A1 | 12/2002 | Mückter |
| 2003/0018336 A1 | 1/2003 | Vandewalle |
| 2003/0032961 A1 | 2/2003 | Pelo et al. |
| 2003/0050642 A1 | 3/2003 | Schmieding et al. |
| 2003/0065332 A1 | 4/2003 | TenHuisen et al. |
| 2003/0074000 A1 | 4/2003 | Roth et al. |
| 2003/0078660 A1 | 4/2003 | Clifford et al. |
| 2003/0083668 A1 | 5/2003 | Rogers et al. |
| 2003/0083688 A1 | 5/2003 | Simonson |
| 2003/0088251 A1 | 5/2003 | Braun et al. |
| 2003/0097131 A1 | 5/2003 | Schon et al. |
| 2003/0139815 A1 | 7/2003 | Grooms et al. |
| 2003/0181979 A1 | 9/2003 | Ferree |
| 2003/0181982 A1 | 9/2003 | Kuslich |
| 2003/0199983 A1 | 10/2003 | Michelson |
| 2003/0229358 A1 | 12/2003 | Errico et al. |
| 2003/0233146 A1 | 12/2003 | Grinberg et al. |
| 2003/0233147 A1 | 12/2003 | Nicholson et al. |
| 2004/0010315 A1 | 1/2004 | Song |
| 2004/0024458 A1 | 2/2004 | Senegas et al. |
| 2004/0034422 A1 | 2/2004 | Errico et al. |
| 2004/0073216 A1 | 4/2004 | Lieberman |
| 2004/0073314 A1 | 4/2004 | White et al. |
| 2004/0082955 A1 | 4/2004 | Zirkle |
| 2004/0087948 A1 | 5/2004 | Suddaby |
| 2004/0097927 A1 | 5/2004 | Yeung et al. |
| 2004/0106925 A1 | 6/2004 | Culbert |
| 2004/0117022 A1 | 6/2004 | Mamay et al. |
| 2004/0127990 A1 | 7/2004 | Bartish, Jr. et al. |
| 2004/0138750 A1 | 7/2004 | Mitchell |
| 2004/0138753 A1 | 7/2004 | Ferree |
| 2004/0147929 A1 | 7/2004 | Biedermann et al. |
| 2004/0158324 A1 | 8/2004 | Lange |
| 2004/0176287 A1 | 9/2004 | Harrison et al. |
| 2004/0176853 A1 | 9/2004 | Sennett et al. |
| 2004/0181282 A1 | 9/2004 | Zucherman et al. |
| 2004/0186572 A1 | 9/2004 | Lange et al. |
| 2004/0210221 A1 | 10/2004 | Kozak et al. |
| 2004/0225360 A1 | 11/2004 | Malone |
| 2004/0230305 A1 | 11/2004 | Gorensek et al. |
| 2004/0260286 A1 | 12/2004 | Ferree |
| 2004/0267369 A1 | 12/2004 | Lyons et al. |
| 2005/0015059 A1 | 1/2005 | Sweeney |
| 2005/0015146 A1 | 1/2005 | Louis et al. |
| 2005/0033435 A1 | 2/2005 | Belliard et al. |
| 2005/0037319 A1 | 2/2005 | Bulard et al. |
| 2005/0049590 A1 | 3/2005 | Alleyne et al. |
| 2005/0055023 A1 | 3/2005 | Sohngen et al. |
| 2005/0070905 A1 | 3/2005 | Donnelly et al. |
| 2005/0070907 A1 | 3/2005 | Abernathie |
| 2005/0071004 A1 | 3/2005 | Re et al. |
| 2005/0075641 A1 | 4/2005 | Singhatat et al. |

(56) References Cited

U.S. PATENT DOCUMENTS

| | | |
|---|---|---|
| 2005/0080415 A1 | 4/2005 | Keyer et al. |
| 2005/0107878 A1 | 5/2005 | Conchy |
| 2005/0112397 A1 | 5/2005 | Rolfe et al. |
| 2005/0113919 A1 | 5/2005 | Cragg et al. |
| 2005/0124993 A1 | 6/2005 | Chappuis |
| 2005/0131409 A1 | 6/2005 | Chervitz et al. |
| 2005/0137605 A1 | 6/2005 | Assell et al. |
| 2005/0143837 A1 | 6/2005 | Ferree |
| 2005/0149192 A1 | 7/2005 | Zucherman et al. |
| 2005/0159749 A1 | 7/2005 | Levy et al. |
| 2005/0159812 A1 | 7/2005 | Dinger et al. |
| 2005/0165398 A1 | 7/2005 | Reiley |
| 2005/0192572 A1 | 9/2005 | Abdelgany et al. |
| 2005/0216082 A1 | 9/2005 | Wilson et al. |
| 2005/0228384 A1 | 10/2005 | Zucherman et al. |
| 2005/0246021 A1 | 11/2005 | Ringeisen et al. |
| 2005/0251146 A1 | 11/2005 | Martz et al. |
| 2005/0273101 A1 | 12/2005 | Schumacher |
| 2005/0277940 A1 | 12/2005 | Neff |
| 2006/0004396 A1 | 1/2006 | Easley et al. |
| 2006/0025771 A1 | 2/2006 | Jackson |
| 2006/0036247 A1 | 2/2006 | Michelson |
| 2006/0036251 A1 | 2/2006 | Reiley |
| 2006/0036252 A1 | 2/2006 | Baynham et al. |
| 2006/0054171 A1 | 3/2006 | Dall |
| 2006/0058793 A1 | 3/2006 | Michelson |
| 2006/0058800 A1 | 3/2006 | Ainsworth et al. |
| 2006/0062825 A1 | 3/2006 | Maccecchini |
| 2006/0084986 A1 | 4/2006 | Grinberg et al. |
| 2006/0089644 A1 | 4/2006 | Felix |
| 2006/0089656 A1 | 4/2006 | Allard et al. |
| 2006/0095038 A1 | 5/2006 | Jackson |
| 2006/0111779 A1 | 5/2006 | Petersen |
| 2006/0129247 A1 | 6/2006 | Brown et al. |
| 2006/0142772 A1 | 6/2006 | Ralph et al. |
| 2006/0161163 A1 | 7/2006 | Shino |
| 2006/0178673 A1 | 8/2006 | Curran |
| 2006/0195094 A1 | 8/2006 | McGraw et al. |
| 2006/0217717 A1 | 9/2006 | Whipple |
| 2006/0241600 A1 | 10/2006 | Ensign et al. |
| 2006/0241776 A1 | 10/2006 | Brown et al. |
| 2006/0271054 A1 | 11/2006 | Sucec et al. |
| 2006/0293662 A1 | 12/2006 | Boyer, II et al. |
| 2007/0027544 A1 | 2/2007 | McCord et al. |
| 2007/0038219 A1 | 2/2007 | Matthis et al. |
| 2007/0049933 A1 | 3/2007 | Ahn et al. |
| 2007/0066977 A1 | 3/2007 | Assell et al. |
| 2007/0073295 A1 | 3/2007 | Biederman et al. |
| 2007/0083265 A1 | 4/2007 | Malone |
| 2007/0088362 A1 | 4/2007 | Bonutti et al. |
| 2007/0093841 A1 | 4/2007 | Hoogland |
| 2007/0093898 A1 | 4/2007 | Schwab et al. |
| 2007/0106383 A1 | 5/2007 | Abdou |
| 2007/0149976 A1 | 6/2007 | Hale et al. |
| 2007/0156144 A1 | 7/2007 | Ulrich et al. |
| 2007/0156241 A1 | 7/2007 | Reiley et al. |
| 2007/0156246 A1 | 7/2007 | Meswania et al. |
| 2007/0161985 A1 | 7/2007 | Demakas et al. |
| 2007/0161989 A1 | 7/2007 | Heinz et al. |
| 2007/0173820 A1 | 7/2007 | Trieu |
| 2007/0219634 A1 | 9/2007 | Greenhalgh et al. |
| 2007/0233080 A1 | 10/2007 | Na et al. |
| 2007/0233146 A1 | 10/2007 | Henniges et al. |
| 2007/0233247 A1 | 10/2007 | Schwab |
| 2007/0250166 A1 | 10/2007 | McKay |
| 2007/0270833 A1 | 11/2007 | Bonutti et al. |
| 2007/0270858 A1 | 11/2007 | Trieu et al. |
| 2007/0270879 A1 | 11/2007 | Isaza et al. |
| 2007/0282443 A1 | 12/2007 | Globerman et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0021480 A1 | 1/2008 | Chin et al. |
| 2008/0065093 A1 | 3/2008 | Assell et al. |
| 2008/0065215 A1 | 3/2008 | Reiley |
| 2008/0071356 A1 | 3/2008 | Greenhalgh et al. |
| 2008/0109083 A1 | 5/2008 | Van Hoeck et al. |
| 2008/0125868 A1 | 5/2008 | Branemark et al. |
| 2008/0132901 A1 | 6/2008 | Recoules-Arche et al. |
| 2008/0140082 A1 | 6/2008 | Erdem et al. |
| 2008/0147079 A1 | 6/2008 | Chin et al. |
| 2008/0154314 A1 | 6/2008 | McDevitt |
| 2008/0154374 A1 | 6/2008 | Labrom |
| 2008/0161810 A1 | 7/2008 | Melkent |
| 2008/0161927 A1 | 7/2008 | Savage et al. |
| 2008/0183204 A1 | 7/2008 | Greenhalgh et al. |
| 2008/0234758 A1 | 9/2008 | Fisher et al. |
| 2008/0249579 A1 | 10/2008 | Taylor |
| 2008/0255562 A1 | 10/2008 | Gil et al. |
| 2008/0255618 A1 | 10/2008 | Fisher et al. |
| 2008/0255622 A1 | 10/2008 | Mickiewicz et al. |
| 2008/0255664 A1 | 10/2008 | Hogendijk et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0294202 A1 | 11/2008 | Peterson et al. |
| 2008/0306554 A1 | 12/2008 | McKinley |
| 2009/0012529 A1 | 1/2009 | Blain et al. |
| 2009/0018660 A1 | 1/2009 | Roush |
| 2009/0024174 A1 | 1/2009 | Stark |
| 2009/0036927 A1 | 2/2009 | Vestgaarden |
| 2009/0037148 A1 | 2/2009 | Lin et al. |
| 2009/0043393 A1 | 2/2009 | Duggal et al. |
| 2009/0082810 A1 | 3/2009 | Bhatnagar et al. |
| 2009/0082869 A1 | 3/2009 | Slemker et al. |
| 2009/0099602 A1 | 4/2009 | Aflatoon |
| 2009/0099610 A1 | 4/2009 | Johnson et al. |
| 2009/0105770 A1 | 4/2009 | Berrevooets et al. |
| 2009/0118771 A1 | 5/2009 | Gonzalez-Hernandez |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0171394 A1 | 7/2009 | Adbou |
| 2009/0187247 A1 | 7/2009 | Metcalf, Jr. et al. |
| 2009/0216238 A1 | 8/2009 | Stark |
| 2009/0270929 A1 | 10/2009 | Suddaby |
| 2009/0287254 A1 | 11/2009 | Nayet et al. |
| 2009/0312798 A1 | 12/2009 | Varela |
| 2009/0319043 A1 | 12/2009 | McDevitt et al. |
| 2009/0324678 A1 | 12/2009 | Thorne et al. |
| 2010/0003638 A1 | 1/2010 | Collins et al. |
| 2010/0022535 A1 | 1/2010 | Lee et al. |
| 2010/0076502 A1 | 3/2010 | Guyer et al. |
| 2010/0081107 A1 | 4/2010 | Bagambisa et al. |
| 2010/0094290 A1 | 4/2010 | Vaidya |
| 2010/0094295 A1 | 4/2010 | Schnieders et al. |
| 2010/0094420 A1 | 4/2010 | Grohowski |
| 2010/0106194 A1 | 4/2010 | Bonutti et al. |
| 2010/0106195 A1 | 4/2010 | Serhan et al. |
| 2010/0114174 A1 | 5/2010 | Jones et al. |
| 2010/0114317 A1 | 5/2010 | Lambrecht et al. |
| 2010/0131011 A1 | 5/2010 | Stark |
| 2010/0137990 A1 | 6/2010 | Apatsidis et al. |
| 2010/0145461 A1 | 6/2010 | Landry et al. |
| 2010/0160977 A1 | 6/2010 | Gephart et al. |
| 2010/0168798 A1 | 7/2010 | Clineff |
| 2010/0191292 A1 | 7/2010 | DeMeo et al. |
| 2010/0228301 A1 | 9/2010 | Greenhalgh et al. |
| 2010/0262242 A1 | 10/2010 | Chavatte et al. |
| 2010/0268228 A1 | 10/2010 | Petersen |
| 2010/0280619 A1 | 11/2010 | Yuan et al. |
| 2010/0280622 A1 | 11/2010 | McKinley |
| 2010/0286778 A1 | 11/2010 | Eisermann et al. |
| 2010/0298889 A1 | 11/2010 | Wilberg et al. |
| 2010/0331851 A1 | 12/2010 | Huene |
| 2010/0331893 A1 | 12/2010 | Geist et al. |
| 2011/0009869 A1 | 1/2011 | Marino et al. |
| 2011/0009966 A1 | 1/2011 | Michelson |
| 2011/0022089 A1 | 1/2011 | Assell et al. |
| 2011/0029019 A1 | 2/2011 | Ainsworth et al. |
| 2011/0040338 A1 | 2/2011 | Jackson |
| 2011/0040362 A1 | 2/2011 | Godara et al. |

(56) References Cited

U.S. PATENT DOCUMENTS

| | | |
|---|---|---|
| 2011/0046737 A1 | 2/2011 | Teisen |
| 2011/0060373 A1 | 3/2011 | Russell et al. |
| 2011/0060375 A1 | 3/2011 | Bonutti |
| 2011/0066190 A1 | 3/2011 | Schaller et al. |
| 2011/0082551 A1 | 4/2011 | Kraus |
| 2011/0093020 A1 | 4/2011 | Wu |
| 2011/0098747 A1 | 4/2011 | Donner et al. |
| 2011/0098816 A1 | 4/2011 | Jacob et al. |
| 2011/0098817 A1 | 4/2011 | Eckhardt et al. |
| 2011/0106175 A1 | 5/2011 | Rezach |
| 2011/0153018 A1 | 6/2011 | Walters et al. |
| 2011/0160866 A1 | 6/2011 | Laurence et al. |
| 2011/0178561 A1 | 7/2011 | Roh |
| 2011/0184417 A1 | 7/2011 | Kitch et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196372 A1 | 8/2011 | Murase |
| 2011/0213432 A1 | 9/2011 | Geist et al. |
| 2011/0230966 A1 | 9/2011 | Trieu |
| 2011/0238074 A1 | 9/2011 | Ek |
| 2011/0238124 A1 | 9/2011 | Richelsoph |
| 2011/0238181 A1 | 9/2011 | Trieu |
| 2011/0245930 A1 | 10/2011 | Alley et al. |
| 2011/0257755 A1 | 10/2011 | Bellemere et al. |
| 2011/0264229 A1 | 10/2011 | Donner |
| 2011/0276098 A1 | 11/2011 | Biedermann et al. |
| 2011/0295272 A1 | 12/2011 | Assell et al. |
| 2011/0295370 A1 | 12/2011 | Suh et al. |
| 2011/0313471 A1 | 12/2011 | McLean et al. |
| 2011/0313532 A1 | 12/2011 | Hunt |
| 2011/0319995 A1 | 12/2011 | Voellmicke et al. |
| 2012/0004730 A1 | 1/2012 | Castro |
| 2012/0035667 A1 | 2/2012 | Van Nortwick et al. |
| 2012/0083887 A1 | 4/2012 | Purcell et al. |
| 2012/0095560 A1 | 4/2012 | Donner |
| 2012/0179256 A1 | 7/2012 | Reiley |
| 2012/0191191 A1 | 7/2012 | Trieu |
| 2012/0215315 A1 | 8/2012 | Hochschuler et al. |
| 2012/0226318 A1 | 9/2012 | Wenger et al. |
| 2012/0253398 A1 | 10/2012 | Metcalf et al. |
| 2012/0259372 A1* | 10/2012 | Glazer ............... A61B 17/686 606/301 |
| 2012/0271424 A1 | 10/2012 | Crawford |
| 2012/0277866 A1 | 11/2012 | Kalluri et al. |
| 2012/0296428 A1 | 11/2012 | Donner |
| 2012/0323285 A1 | 12/2012 | Assell et al. |
| 2013/0018427 A1 | 1/2013 | Pham et al. |
| 2013/0030456 A1 | 1/2013 | Assell et al. |
| 2013/0030529 A1 | 1/2013 | Hunt |
| 2013/0035727 A1 | 2/2013 | Datta |
| 2013/0053852 A1 | 2/2013 | Greenhalgh et al. |
| 2013/0053854 A1 | 2/2013 | Schoenefeld et al. |
| 2013/0053902 A1 | 2/2013 | Trudeau |
| 2013/0053963 A1 | 2/2013 | Davenport |
| 2013/0072984 A1 | 3/2013 | Robinson |
| 2013/0085535 A1 | 4/2013 | Greenhalgh et al. |
| 2013/0096683 A1 | 4/2013 | Kube |
| 2013/0116793 A1 | 5/2013 | Kloss |
| 2013/0123850 A1 | 5/2013 | Schoenefeld et al. |
| 2013/0123935 A1 | 5/2013 | Hunt et al. |
| 2013/0131678 A1 | 5/2013 | Dahners |
| 2013/0144343 A1 | 6/2013 | Arnett et al. |
| 2013/0158609 A1 | 6/2013 | Mikhail et al. |
| 2013/0172736 A1 | 7/2013 | Abdou |
| 2013/0197590 A1 | 8/2013 | Assell et al. |
| 2013/0203088 A1 | 8/2013 | Baerlecken et al. |
| 2013/0218215 A1 | 8/2013 | Ginn et al. |
| 2013/0218282 A1 | 8/2013 | Hunt |
| 2013/0231746 A1 | 9/2013 | Ginn et al. |
| 2013/0237988 A1 | 9/2013 | Mauldin |
| 2013/0245703 A1 | 9/2013 | Warren et al. |
| 2013/0245763 A1 | 9/2013 | Mauldin |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0274890 A1 | 10/2013 | McKay |
| 2013/0325129 A1 | 12/2013 | Huang |
| 2014/0012334 A1 | 1/2014 | Armstrong et al. |
| 2014/0012340 A1 | 1/2014 | Beck et al. |
| 2014/0012384 A1 | 1/2014 | Kana et al. |
| 2014/0031934 A1 | 1/2014 | Trieu |
| 2014/0031935 A1 | 1/2014 | Donner et al. |
| 2014/0031938 A1 | 1/2014 | Lechmann et al. |
| 2014/0031939 A1 | 1/2014 | Wolfe et al. |
| 2014/0046380 A1 | 2/2014 | Asfora |
| 2014/0074175 A1 | 3/2014 | Ehler et al. |
| 2014/0088596 A1 | 3/2014 | Assell et al. |
| 2014/0088707 A1 | 3/2014 | Donner et al. |
| 2014/0121776 A1 | 5/2014 | Hunt |
| 2014/0135927 A1 | 5/2014 | Pavlov et al. |
| 2014/0142700 A1 | 5/2014 | Donner et al. |
| 2014/0172026 A1 | 6/2014 | Biedermann et al. |
| 2014/0172027 A1 | 6/2014 | Biedermann et al. |
| 2014/0200618 A1 | 7/2014 | Donner et al. |
| 2014/0207240 A1 | 7/2014 | Stoffman et al. |
| 2014/0257294 A1 | 9/2014 | Gedet et al. |
| 2014/0257408 A1 | 9/2014 | Trieu et al. |
| 2014/0276846 A1 | 9/2014 | Mauldin et al. |
| 2014/0276851 A1 | 9/2014 | Schneider et al. |
| 2014/0277139 A1 | 9/2014 | Vrionis et al. |
| 2014/0277165 A1 | 9/2014 | Katzman et al. |
| 2014/0277460 A1 | 9/2014 | Schifano et al. |
| 2014/0277462 A1 | 9/2014 | Yerby et al. |
| 2014/0277463 A1 | 9/2014 | Yerby et al. |
| 2014/0288649 A1 | 9/2014 | Hunt |
| 2014/0288650 A1 | 9/2014 | Hunt |
| 2014/0296982 A1 | 10/2014 | Cheng |
| 2014/0330382 A1 | 11/2014 | Mauldin |
| 2014/0364917 A1 | 12/2014 | Sandstrom et al. |
| 2015/0012051 A1 | 1/2015 | Warren et al. |
| 2015/0039037 A1 | 2/2015 | Donner et al. |
| 2015/0080951 A1 | 3/2015 | Yeh |
| 2015/0080972 A1 | 3/2015 | Chin et al. |
| 2015/0094765 A1 | 4/2015 | Donner et al. |
| 2015/0112444 A1 | 4/2015 | Aksu |
| 2015/0147397 A1 | 5/2015 | Altschuler |
| 2015/0150683 A1 | 6/2015 | Donner et al. |
| 2015/0173805 A1 | 6/2015 | Donner et al. |
| 2015/0173904 A1 | 6/2015 | Stark |
| 2015/0182268 A1 | 7/2015 | Donner et al. |
| 2015/0190149 A1 | 7/2015 | Assell et al. |
| 2015/0190187 A1 | 7/2015 | Parent et al. |
| 2015/0209094 A1 | 7/2015 | Anderson |
| 2015/0216566 A1 | 8/2015 | Mikhail et al. |
| 2015/0238203 A1 | 8/2015 | Asfora |
| 2015/0250513 A1 | 9/2015 | De Lavigne Sainte |
| 2015/0250611 A1 | 9/2015 | Schifano et al. |
| 2015/0250612 A1 | 9/2015 | Schifano et al. |
| 2015/0257892 A1 | 9/2015 | Lechmann et al. |
| 2015/0313720 A1 | 11/2015 | Lorio |
| 2015/0320450 A1 | 11/2015 | Mootien et al. |
| 2015/0320451 A1 | 11/2015 | Mootien et al. |
| 2015/0320469 A1 | 11/2015 | Biedermann et al. |
| 2015/0342753 A1 | 12/2015 | Donner et al. |
| 2016/0000488 A1 | 1/2016 | Cross, III |
| 2016/0022429 A1 | 1/2016 | Greenhalgh et al. |
| 2016/0095711 A1 | 4/2016 | Castro |
| 2016/0095721 A1 | 4/2016 | Schell et al. |
| 2016/0100870 A1 | 4/2016 | Lavigne et al. |
| 2016/0106477 A1 | 4/2016 | Hynes et al. |
| 2016/0106479 A1 | 4/2016 | Hynes et al. |
| 2016/0120661 A1 | 5/2016 | Schell et al. |
| 2016/0143671 A1 | 5/2016 | Jimenez |
| 2016/0157908 A1 | 6/2016 | Cawley et al. |
| 2016/0166291 A1 | 6/2016 | Goel et al. |
| 2016/0166301 A1 | 6/2016 | Papangelou et al. |
| 2016/0175113 A1 | 6/2016 | Lins |
| 2016/0184103 A1 | 6/2016 | Fonte et al. |
| 2016/0213487 A1 | 7/2016 | Wilson et al. |
| 2016/0242820 A1 | 8/2016 | Whipple et al. |
| 2016/0242912 A1 | 8/2016 | Lindsey et al. |
| 2016/0249940 A1 | 9/2016 | Stark |
| 2016/0287171 A1 | 10/2016 | Sand et al. |

(56) References Cited

U.S. PATENT DOCUMENTS

| | | |
|---|---|---|
| 2016/0287301 A1 | 10/2016 | Mehl et al. |
| 2016/0310188 A1 | 10/2016 | Marino et al. |
| 2016/0310197 A1 | 10/2016 | Black et al. |
| 2016/0324643 A1 | 11/2016 | Donner et al. |
| 2016/0324656 A1 | 11/2016 | Morris et al. |
| 2016/0374727 A1 | 12/2016 | Greenhalgh et al. |
| 2017/0014235 A1 | 1/2017 | Jones et al. |
| 2017/0020573 A1 | 1/2017 | Cain et al. |
| 2017/0020585 A1 | 1/2017 | Harshman et al. |
| 2017/0086885 A1 | 3/2017 | Duncan et al. |
| 2017/0128083 A1 | 5/2017 | Germain |
| 2017/0128214 A1 | 5/2017 | Mayer |
| 2017/0135733 A1 | 5/2017 | Donner et al. |
| 2017/0135737 A1 | 5/2017 | Krause |
| 2017/0143513 A1 | 5/2017 | Sandstrom et al. |
| 2017/0156879 A1 | 6/2017 | Janowski |
| 2017/0156880 A1 | 6/2017 | Halverson et al. |
| 2017/0202511 A1 | 7/2017 | Chang et al. |
| 2017/0209155 A1 | 7/2017 | Petersen |
| 2017/0216036 A1 | 8/2017 | Cordaro |
| 2017/0224393 A1 | 8/2017 | Lavigne et al. |
| 2017/0246000 A1 | 8/2017 | Pavlov et al. |
| 2017/0258498 A1 | 9/2017 | Redmond et al. |
| 2017/0258506 A1 | 9/2017 | Redmond et al. |
| 2017/0258606 A1 | 9/2017 | Afzal |
| 2017/0266007 A1 | 9/2017 | Gelaude et al. |
| 2017/0296344 A1 | 10/2017 | Souza et al. |
| 2017/0303938 A1 | 10/2017 | Rindal et al. |
| 2017/0333205 A1 | 11/2017 | Joly et al. |
| 2017/0348034 A1 | 12/2017 | LaPierre et al. |
| 2017/0354442 A1 | 12/2017 | Kim et al. |
| 2017/0360570 A1 | 12/2017 | Berndt et al. |
| 2018/0008256 A1 | 1/2018 | Fallin et al. |
| 2018/0036041 A1 | 2/2018 | Pham et al. |
| 2018/0042652 A1 | 2/2018 | Mari et al. |
| 2018/0042735 A1 | 2/2018 | Schell et al. |
| 2018/0092677 A1* | 4/2018 | Peterson .............. A61B 17/866 |
| 2018/0104063 A1 | 4/2018 | Asaad |
| 2018/0104068 A1 | 4/2018 | Sack |
| 2018/0110624 A1 | 4/2018 | Arnone |
| 2018/0110626 A1 | 4/2018 | McShane, III et al. |
| 2018/0200063 A1 | 7/2018 | Kahmer et al. |
| 2018/0214192 A1* | 8/2018 | Roby .................... A61L 31/146 |
| 2018/0228613 A1 | 8/2018 | Jones et al. |
| 2018/0228617 A1 | 8/2018 | Srour et al. |
| 2018/0228621 A1 | 8/2018 | Reiley et al. |
| 2018/0235643 A1 | 8/2018 | Lins et al. |
| 2018/0243097 A1 | 8/2018 | Jones et al. |
| 2018/0256232 A1 | 9/2018 | Russell |
| 2018/0256351 A1 | 9/2018 | Bishop et al. |
| 2018/0256352 A1 | 9/2018 | Nyahay et al. |
| 2018/0256361 A1 | 9/2018 | Bishop et al. |
| 2018/0280139 A1 | 10/2018 | Jones et al. |
| 2018/0280140 A1 | 10/2018 | Jones et al. |
| 2018/0289504 A1 | 10/2018 | Arthurs et al. |
| 2018/0296227 A1 | 10/2018 | Meek et al. |
| 2018/0296347 A1 | 10/2018 | Hamzey et al. |
| 2018/0296363 A1 | 10/2018 | Berry |
| 2018/0303520 A1 | 10/2018 | Rajpal |
| 2018/0303623 A1 | 10/2018 | Shoshtaev |
| 2018/0303624 A1 | 10/2018 | Shoshtaev |
| 2018/0317971 A1 | 11/2018 | Prevost |
| 2018/0360512 A1 | 12/2018 | Mari |
| 2018/0368894 A1 | 12/2018 | Wieland et al. |
| 2019/0000636 A1 | 1/2019 | Kim et al. |
| 2019/0008562 A1 | 1/2019 | Melton et al. |
| 2019/0046684 A1 | 2/2019 | Roth |
| 2019/0076258 A1 | 3/2019 | Black et al. |
| 2019/0076266 A1 | 3/2019 | Trudeau et al. |
| 2019/0083270 A1 | 3/2019 | Milz et al. |
| 2019/0091027 A1 | 3/2019 | Asaad et al. |
| 2019/0117827 A1 | 4/2019 | Roth |
| 2019/0125371 A1 | 5/2019 | Asfora et al. |
| 2019/0125408 A1 | 5/2019 | Asfora et al. |
| 2019/0133613 A1 | 5/2019 | Reiley et al. |
| 2019/0133769 A1 | 5/2019 | Tetsworth et al. |
| 2019/0133783 A1 | 5/2019 | Unger et al. |
| 2019/0142606 A1 | 5/2019 | Freudenberger |
| 2019/0150910 A1 | 5/2019 | Jones et al. |
| 2019/0151113 A1 | 5/2019 | Sack |
| 2019/0151114 A1 | 5/2019 | Sack |
| 2019/0167326 A1 | 6/2019 | Greenhalgh et al. |
| 2019/0183653 A1 | 6/2019 | Gregersen et al. |
| 2019/0231554 A1 | 8/2019 | Bishop et al. |
| 2019/0239935 A1 | 8/2019 | Willis et al. |
| 2019/0247094 A1 | 8/2019 | Yacoub et al. |
| 2019/0254840 A1 | 8/2019 | Gray et al. |
| 2019/0262048 A1 | 8/2019 | Sutika |
| 2019/0262049 A1 | 8/2019 | Tempco et al. |
| 2019/0290441 A1 | 9/2019 | Tong et al. |
| 2019/0298528 A1 | 10/2019 | Lindsey et al. |
| 2019/0298542 A1 | 10/2019 | Kloss |
| 2019/0328546 A1 | 10/2019 | Palagi et al. |
| 2019/0343564 A1 | 11/2019 | Tempco et al. |
| 2019/0343565 A1 | 11/2019 | Tempco et al. |
| 2019/0343566 A1 | 11/2019 | Tempco et al. |
| 2019/0343567 A1 | 11/2019 | Tempco et al. |
| 2019/0343640 A1 | 11/2019 | Donner et al. |
| 2019/0343644 A1 | 11/2019 | Ryan et al. |
| 2019/0343645 A1 | 11/2019 | Miccio et al. |
| 2019/0343652 A1 | 11/2019 | Petersheim et al. |
| 2019/0343653 A1 | 11/2019 | McKay |
| 2019/0388131 A1 | 12/2019 | Mehl et al. |
| 2019/0388228 A1 | 12/2019 | Donner et al. |
| 2019/0388242 A1 | 12/2019 | Harris et al. |
| 2020/0000595 A1 | 1/2020 | Jones et al. |
| 2020/0022817 A1 | 1/2020 | Crossgrove et al. |
| 2020/0038069 A1 | 2/2020 | Jones et al. |
| 2020/0046512 A1 | 2/2020 | Newman et al. |
| 2020/0069431 A1 | 3/2020 | Boehm et al. |
| 2020/0100822 A1 | 4/2020 | Lipow |
| 2020/0129214 A1 | 4/2020 | Pepper et al. |
| 2020/0138485 A1 | 5/2020 | Kuwamura et al. |
| 2020/0138492 A1 | 5/2020 | Kavanagh |
| 2020/0146721 A1 | 5/2020 | Sadiq |
| 2020/0149137 A1 | 5/2020 | Roth |
| 2020/0170679 A1 | 6/2020 | Sciubba et al. |
| 2020/0206390 A1 | 7/2020 | Roth |
| 2020/0222088 A1 | 7/2020 | Kraus |
| 2020/0222195 A1 | 7/2020 | Assell et al. |
| 2020/0246158 A1 | 8/2020 | Bergey |
| 2020/0254140 A1 | 8/2020 | Roth |
| 2020/0315647 A1 | 10/2020 | Fojtik et al. |
| 2020/0315666 A1 | 10/2020 | Nichols et al. |
| 2020/0315669 A1 | 10/2020 | Dejardin |
| 2020/0345507 A1 | 11/2020 | Reiley |
| 2020/0345508 A1 | 11/2020 | Reiley |
| 2020/0345510 A1 | 11/2020 | Reiley |
| 2020/0375750 A1 | 12/2020 | Abbasi et al. |
| 2020/0397491 A1 | 12/2020 | Frey et al. |
| 2021/0022882 A1 | 1/2021 | Dang et al. |
| 2021/0107093 A1 | 4/2021 | Tempco |
| 2021/0169660 A1 | 6/2021 | Reckling et al. |
| 2021/0212734 A1 | 7/2021 | Mesiwala et al. |
| 2021/0228360 A1 | 7/2021 | Hunt et al. |
| 2021/0236146 A1 | 8/2021 | Donner et al. |
| 2021/0338454 A1 | 11/2021 | Afzal |
| 2021/0346038 A1 | 11/2021 | Fiechter et al. |
| 2021/0353337 A1 | 11/2021 | Kaufmann et al. |
| 2021/0353338 A1 | 11/2021 | Meek et al. |
| 2021/0393408 A1 | 12/2021 | Ginn |
| 2021/0393409 A1 | 12/2021 | Ginn |
| 2022/0031474 A1 | 2/2022 | Reckling et al. |
| 2022/0096098 A1 | 3/2022 | Sand et al. |
| 2022/0117640 A1 | 4/2022 | Schneider et al. |
| 2022/0273447 A1 | 9/2022 | Ginn |
| 2022/0273448 A1 | 9/2022 | Ginn et al. |
| 2022/0280303 A1 | 9/2022 | Mauldin et al. |
| 2022/0296377 A1 | 9/2022 | Ginn et al. |
| 2022/0296378 A1 | 9/2022 | Ginn |
| 2022/0304813 A1 | 9/2022 | Ginn et al. |
| 2022/0304814 A1 | 9/2022 | Ginn |
| 2022/0354665 A1 | 11/2022 | Mesiwala et al. |
| 2022/0409381 A1 | 12/2022 | Ginn |

(56) References Cited

U.S. PATENT DOCUMENTS

| | | |
|---|---|---|
| 2023/0000526 A1 | 1/2023 | Follini et al. |
| 2023/0000630 A1 | 1/2023 | Ginn et al. |
| 2023/0000631 A1 | 1/2023 | Ginn et al. |
| 2023/0000639 A1 | 1/2023 | Stuart et al. |
| 2023/0076180 A1 | 3/2023 | Schifano et al. |
| 2023/0095586 A1 | 3/2023 | Mauldin et al. |
| 2023/0210667 A1 | 7/2023 | Lindsey et al. |
| 2023/0263553 A1 | 8/2023 | Compton et al. |
| 2023/0285054 A1 | 9/2023 | Mehl et al. |
| 2023/0293206 A1 | 9/2023 | Mundis, Jr. et al. |
| 2023/0321317 A1 | 10/2023 | Suh |
| 2023/0329765 A1 | 10/2023 | Lavigne et al. |
| 2023/0390078 A1 | 12/2023 | Bergey et al. |
| 2023/0404762 A1 | 12/2023 | Ginn et al. |
| 2024/0050131 A1 | 2/2024 | Bannigan et al. |
| 2024/0130742 A1 | 4/2024 | Reiley et al. |
| 2024/0206885 A1 | 6/2024 | Sand et al. |
| 2024/0252717 A1 | 8/2024 | Suh et al. |
| 2024/0261107 A1 | 8/2024 | Ginn et al. |
| 2024/0285410 A1 | 8/2024 | Ginn et al. |
| 2025/0040972 A1 | 2/2025 | Schneider et al. |

FOREIGN PATENT DOCUMENTS

| | | |
|---|---|---|
| CN | 1909848 A | 2/2007 |
| CN | 101795632 A | 8/2010 |
| CN | 102361601 A | 2/2012 |
| CN | 102429716 A | 5/2012 |
| CN | 104968283 A | 10/2015 |
| CN | 109124748 A | 6/2017 |
| DE | 102011001264 A1 | 9/2012 |
| DE | 102012106336 A1 | 1/2014 |
| EP | 1287796 A1 | 3/2003 |
| EP | 2070481 B1 | 2/2012 |
| EP | 2796104 A1 | 10/2014 |
| EP | 2590576 B1 | 10/2015 |
| EP | 2749238 B1 | 3/2017 |
| EP | 2887899 B1 | 8/2017 |
| EP | 2341852 B1 | 8/2018 |
| EP | 2496162 B1 | 10/2018 |
| EP | 3484387 A1 | 5/2019 |
| EP | 3501457 A1 | 6/2019 |
| EP | 356044/8 A1 | 10/2019 |
| EP | 3593745 A2 | 1/2020 |
| EP | 3616634 A1 | 3/2020 |
| EP | 3661441 A1 | 6/2020 |
| EP | 2408389 B1 | 4/2021 |
| JP | 59200642 A | 11/1984 |
| JP | 05-176942 A | 7/1993 |
| JP | 05184615 A | 7/1993 |
| JP | 09149906 A | 10/1997 |
| JP | 10-85231 A | 4/1998 |
| JP | 11318931 A | 11/1999 |
| JP | 2002509753 A | 4/2002 |
| JP | 2003511198 A | 3/2003 |
| JP | 2003533329 A | 11/2003 |
| JP | 2003534046 A | 11/2003 |
| JP | 2004121841 | 4/2004 |
| JP | 2004512895 | 4/2004 |
| JP | 2004516866 | 6/2004 |
| JP | 2006506181 | 2/2006 |
| JP | 2007535973 A | 12/2007 |
| JP | 2008540036 A | 11/2008 |
| JP | 2009000501 A | 1/2009 |
| JP | 2009521990 A | 6/2009 |
| JP | 2009533159 A | 9/2009 |
| JP | 2010137016 A | 6/2010 |
| JP | 2011041802 A | 3/2011 |
| JP | 2011512939 A | 4/2011 |
| JP | 2012030105 A | 2/2012 |
| JP | 2014000402 A | 1/2014 |
| JP | 2014147820 A | 8/2014 |
| JP | 2015510506 A | 4/2015 |
| JP | 2015171520 A | 10/2015 |
| JP | 2015531282 A | 11/2015 |
| JP | 2016515857 A | 6/2016 |
| JP | 2017528251 A | 9/2017 |
| JP | 2017533759 A | 11/2017 |
| JP | 2019506993 A | 3/2019 |
| WO | WO97/31517 A2 | 8/1997 |
| WO | WO01/17445 A1 | 3/2001 |
| WO | WO02/38054 | 5/2002 |
| WO | WO03/007839 A2 | 1/2003 |
| WO | WO04/02344 | 1/2004 |
| WO | WO2004/043277 A1 | 5/2004 |
| WO | WO2005/009729 A2 | 2/2005 |
| WO | WO2006/003316 | 1/2006 |
| WO | WO2006/023793 A2 | 3/2006 |
| WO | WO2006/074321 A2 | 7/2006 |
| WO | WO2006/116850 A1 | 11/2006 |
| WO | WO2008/153723 A1 | 12/2008 |
| WO | WO2009/025884 A2 | 2/2009 |
| WO | WO2009/029074 A1 | 3/2009 |
| WO | WO2010/105196 A1 | 9/2010 |
| WO | WO2011/010463 A1 | 1/2011 |
| WO | WO2011/110865 A2 | 9/2011 |
| WO | WO2011/124874 A1 | 10/2011 |
| WO | WO2011/149557 A1 | 12/2011 |
| WO | WO2012/015976 A1 | 2/2012 |
| WO | WO2012/048008 A1 | 4/2012 |
| WO | WO2013/000071 A1 | 1/2013 |
| WO | WO2013/052807 A2 | 4/2013 |
| WO | WO2013/119907 A1 | 8/2013 |
| WO | WO2013/134678 A1 | 9/2013 |
| WO | WO2014/145902 A1 | 9/2014 |
| WO | WO2017/147140 A1 | 8/2017 |
| WO | WO2017/147537 A1 | 8/2017 |
| WO | WO2017/201371 A1 | 11/2017 |
| WO | WO2019/152737 A1 | 8/2019 |
| WO | WO2020/168269 A1 | 8/2020 |

OTHER PUBLICATIONS

Acumed; Acutrak Headless Compressioin Screw (product information); 12 pgs; © 2005; retrieved Sep. 25, 2014 from http://www.rcsed.ac.uk/fellows/Ivanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Eisner; New SI Joint Fusion System Cleared; Orthopedics This Week; Jun. 28, 2018; retrieved from the internet <https://ryortho.com/breaking/new-si-joint-fusion-system-cleared/> on Sep. 8, 2022; 5 pages.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Wise et al., Minimally invasive sacroiliac arthrodesis, outcomes of a new technique; J Spinal Disord Tech; vol. 21; No. 8; pp. 579-584; Dec. 2008.

Third Party Observation; PCT/US2021/062337; Aug. 29, 2022; 6 pages.

Stuart et al.; U.S. Appl. No. 18/309,686 entitled "Bone stabilizing implants and methods of placement across si joints," filed Apr. 28, 2023.

Mesiwala et al.; U.S. Appl. No. 18/632,102 entitled "Implants for spinal fixation or fusion," filed Apr. 10, 2024.

Mauldin et al.; U.S. Appl. No. 18/509,864 entitled "Systems, device, and methods for joint fusion," filed Nov. 15, 2023.

Sand et al.; U.S. Appl. No. 18/527,030 entitled "Systems and methods for decorticating the sacroiliac joint," filed Dec. 1, 2023.

Stuart et al.; U.S. Appl. No. 18/805,412 entitled "Pelvic stabilization implants, methods of use and manufacture," filed Aug. 14, 2024.

(56) References Cited

OTHER PUBLICATIONS

Reckling et al.; U.S. Appl. No. 18/809,229 entitled "Sacro-iliac joint stabilizing implants and methods of implantation," filed Aug. 19, 2024.
Mesiwala et al.; U.S. Appl. No. 18/810,211 entitled "Implants for spinal fixation and or fusion," filed Aug. 20, 2024.
Sand et al.; U.S. Appl. No. 18/951,349 entitled "Systems, devices, and methods for preparing bone to receive an implant," filed Nov. 18, 2024.
Sand et al.; U.S. Appl. No. 18/951,396 entitled "Sacroiliac joint stabilization, including implants, systems and methods of delivering implants," filed Nov. 18, 2024.
Mesiwala et al.; U.S. Appl. No. 18/716,090 entitled "Fusion cages and methods for sacro-iliac joint stabilization," filed Jun. 3, 2024.
Mauldin et al.; U.S. Appl. No. 18/733,547 entitled "Fenestrated implant," filed Jun. 4, 2024.
Stuart et al,; U.S. Appl. No. 18/780,141 entitled "Sacro-iliac joint stabilizing implants and methods of implantation," filed Jul. 22, 2024.

* cited by examiner (Anterior)

(Posterior)

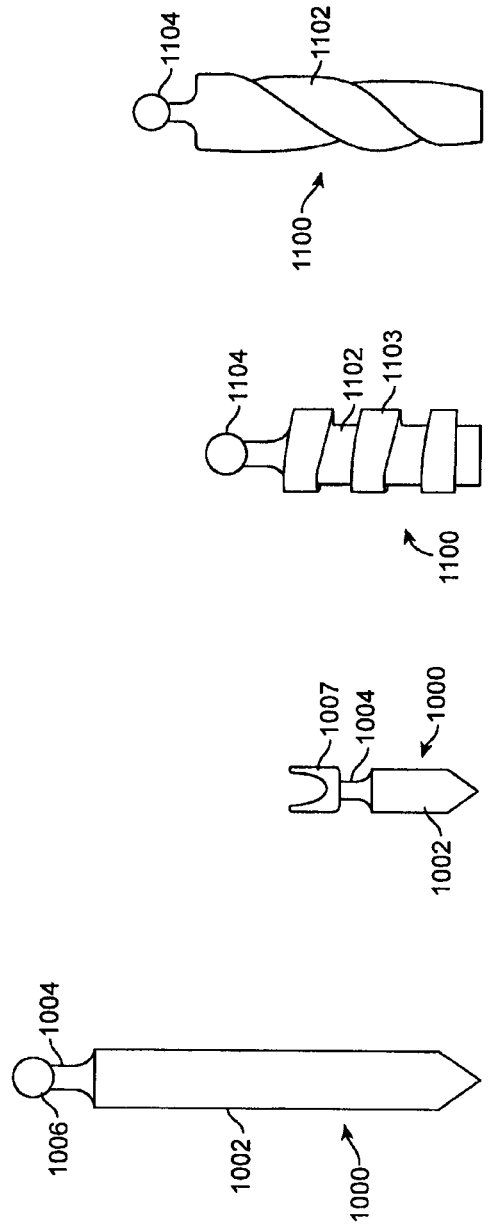

Translaminar
Lumbar Fusion
(Posterior Approach)

Lumbar Facet Fusion (Posterior Approach)

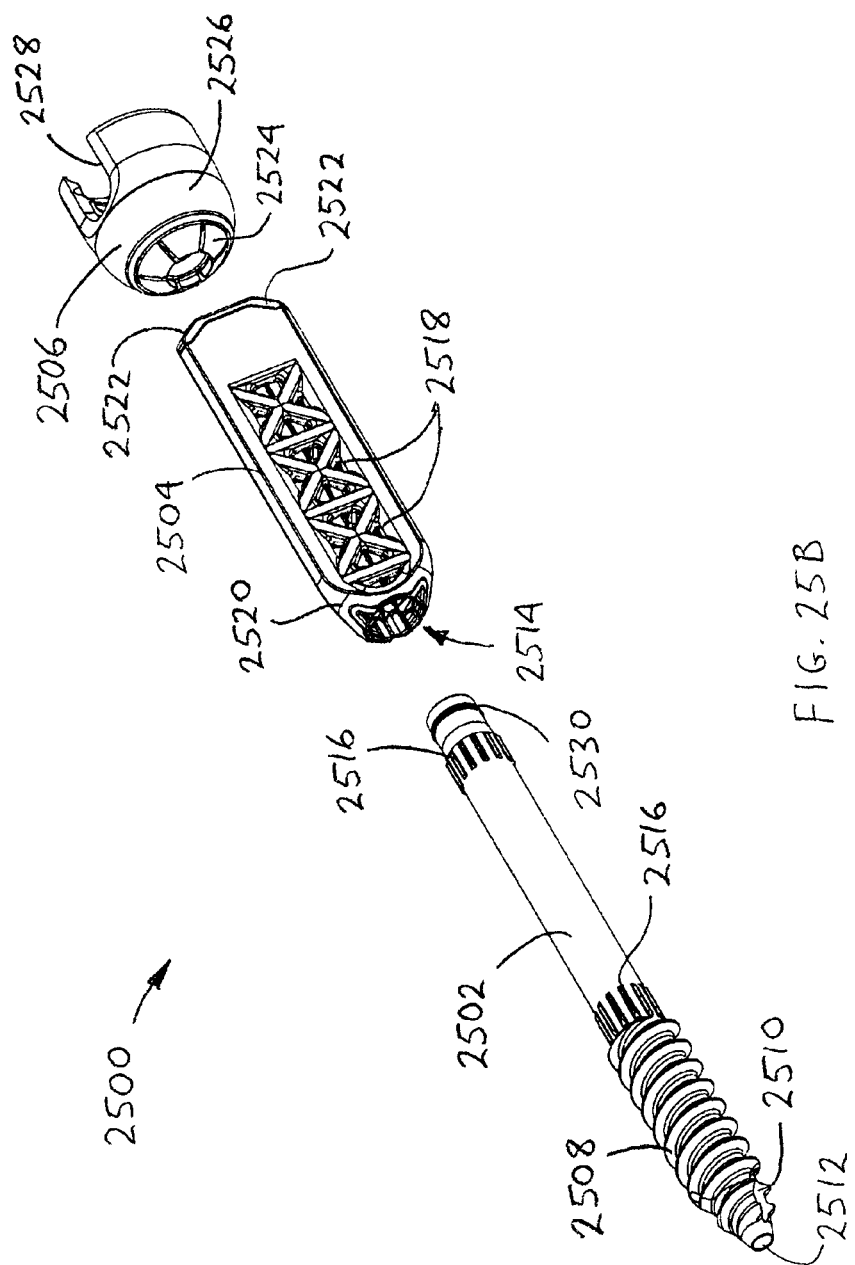

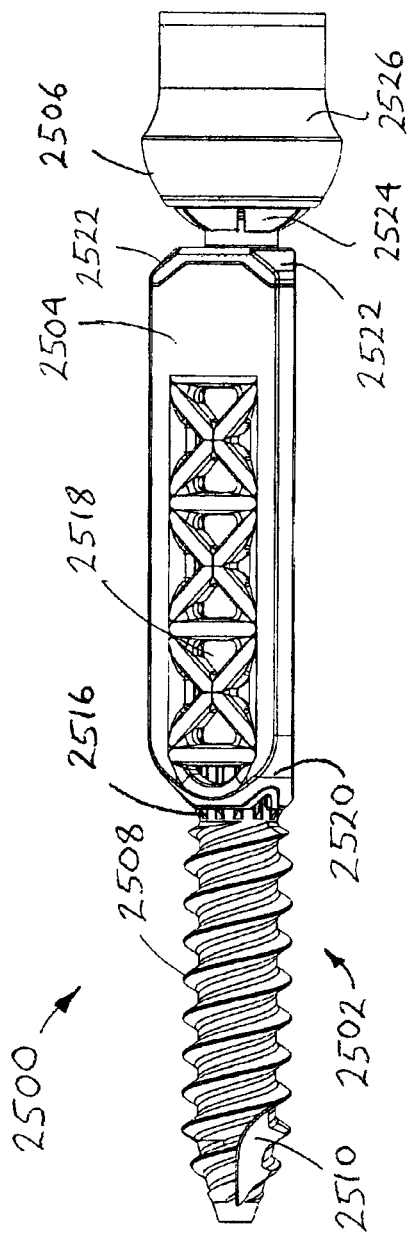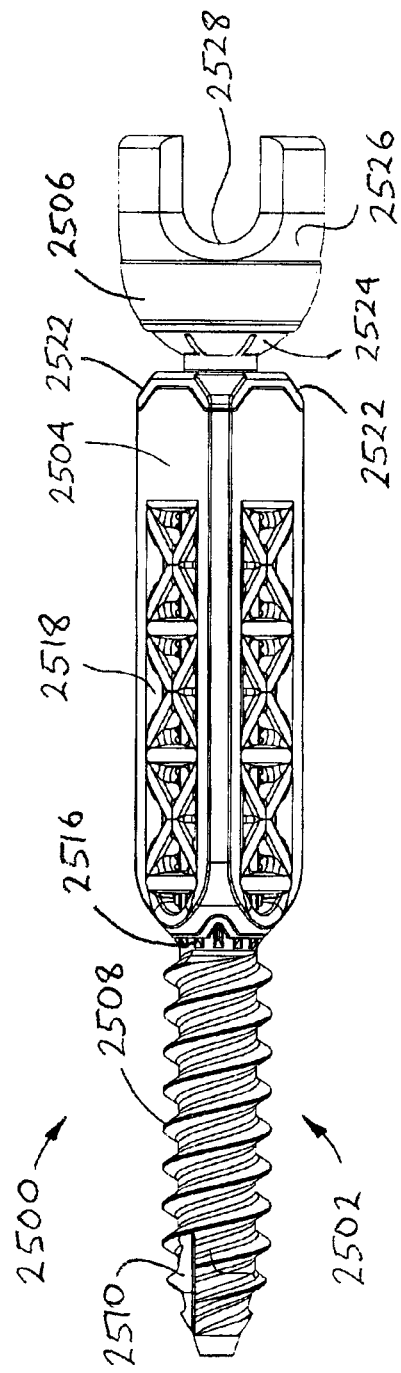
FIG. 25C
FIG. 25D

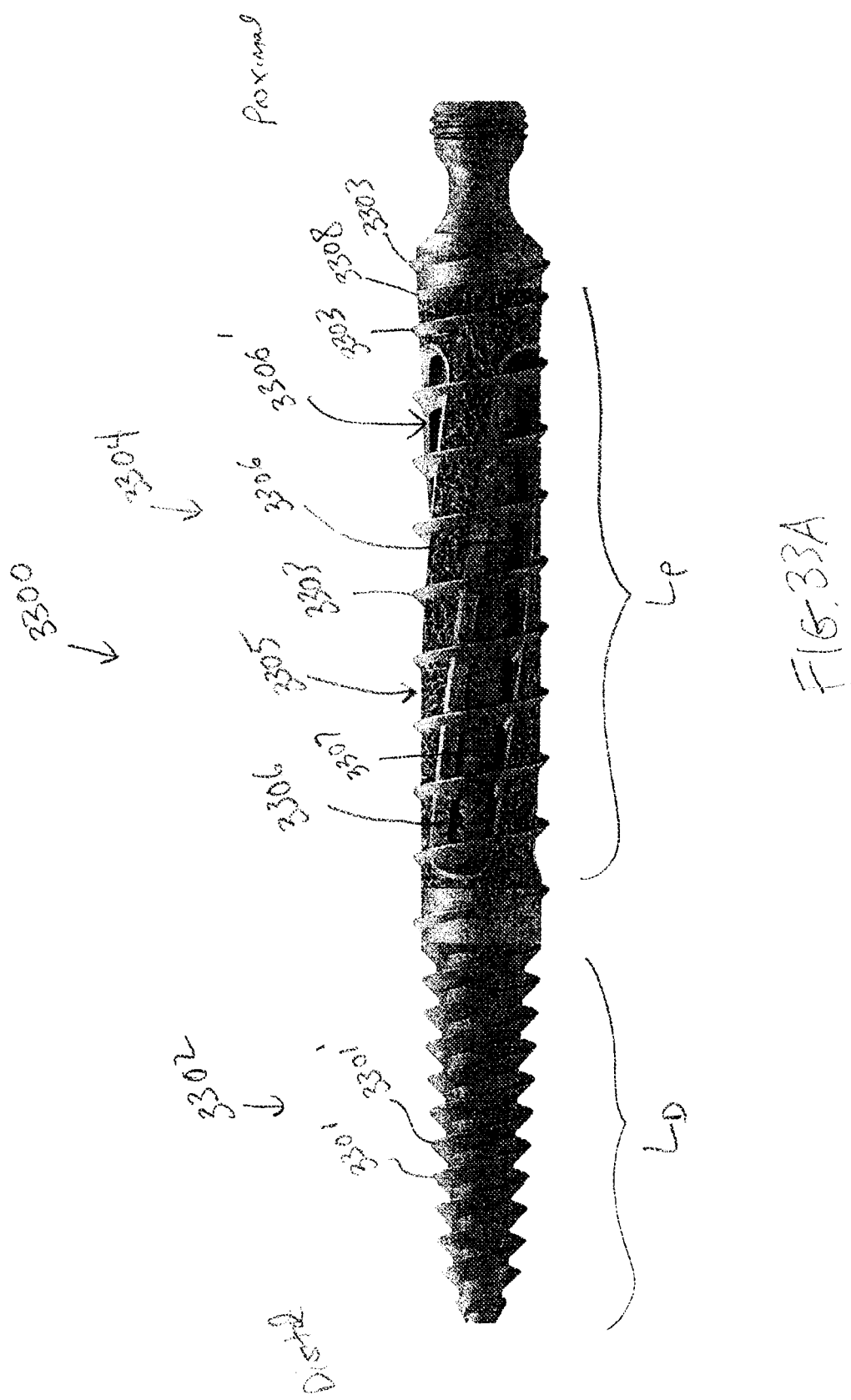

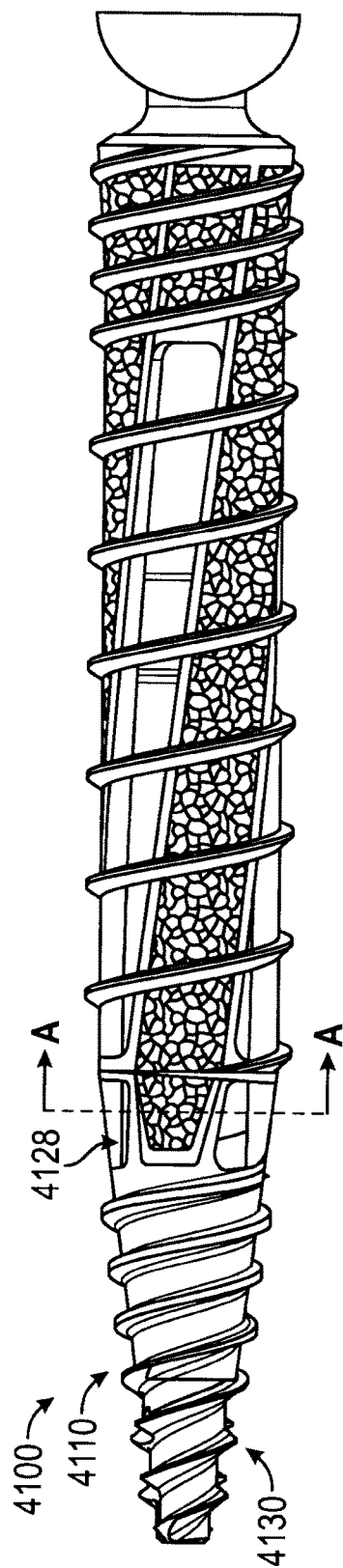
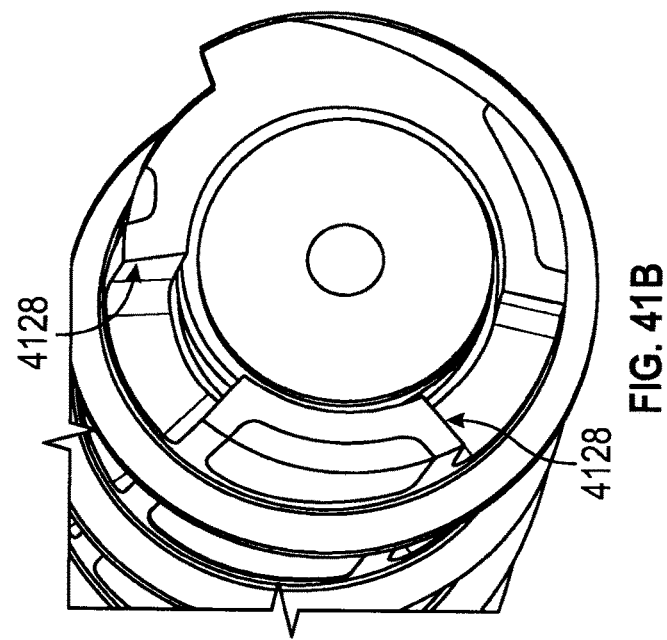
FIG. 41A
FIG. 41B

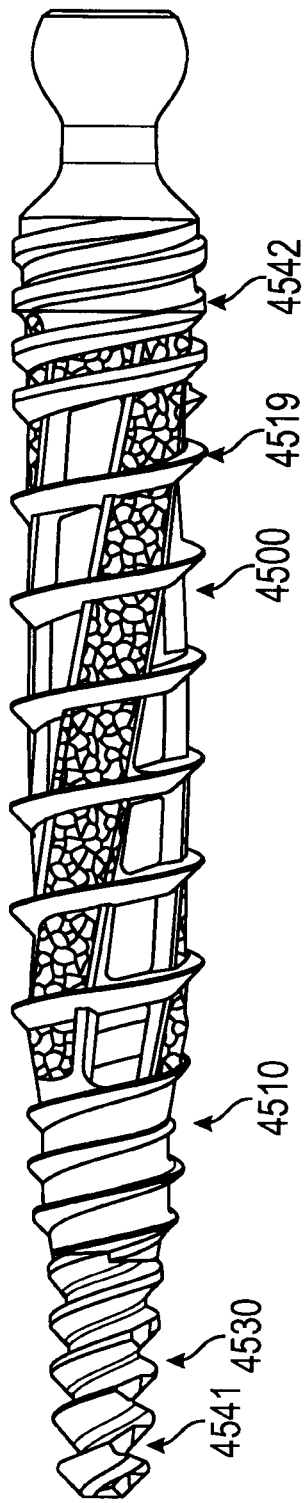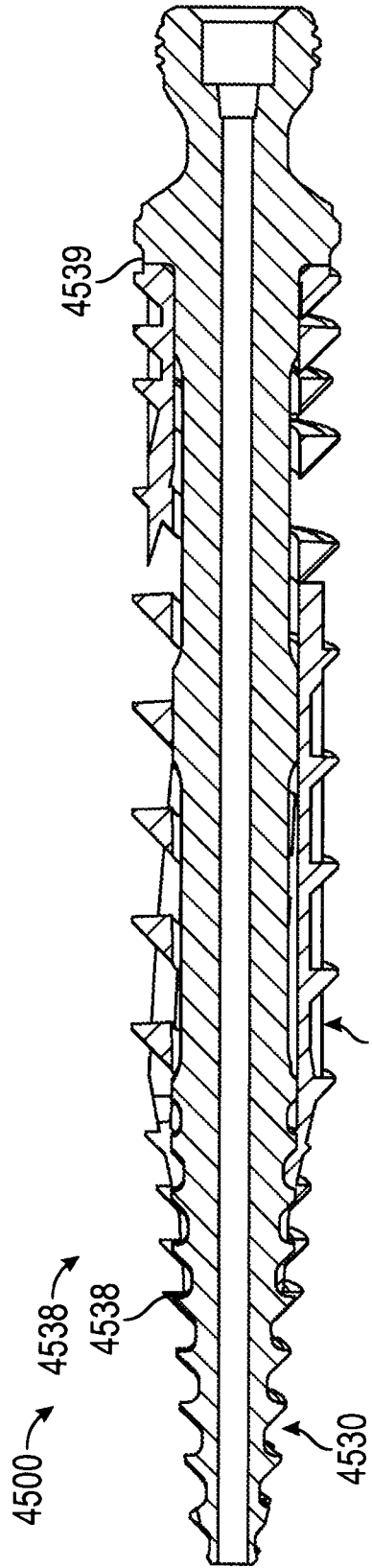
FIG. 45A
FIG. 45B

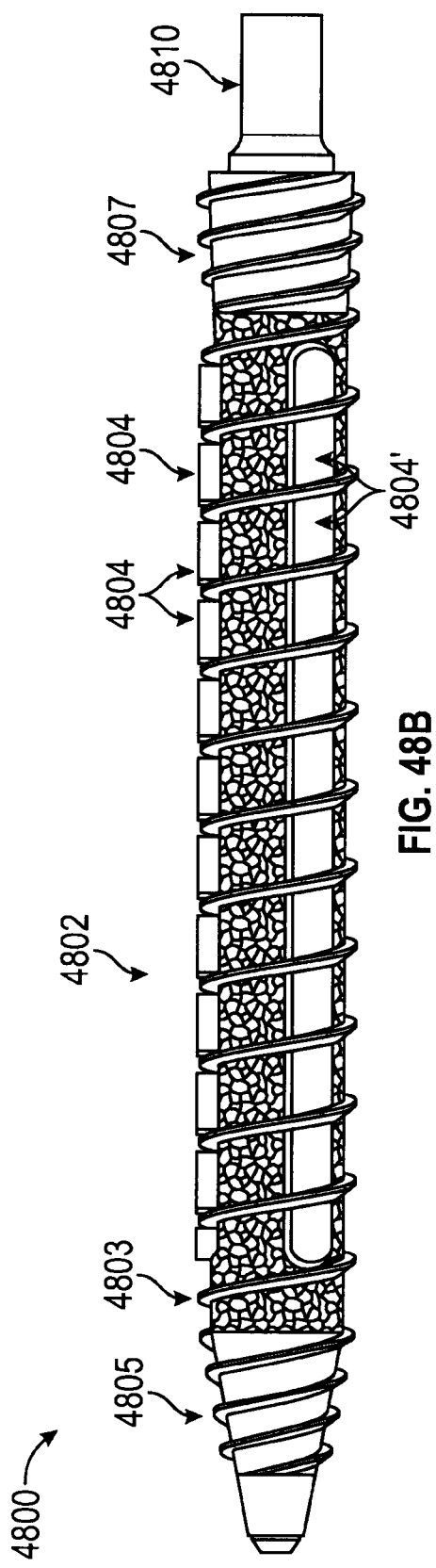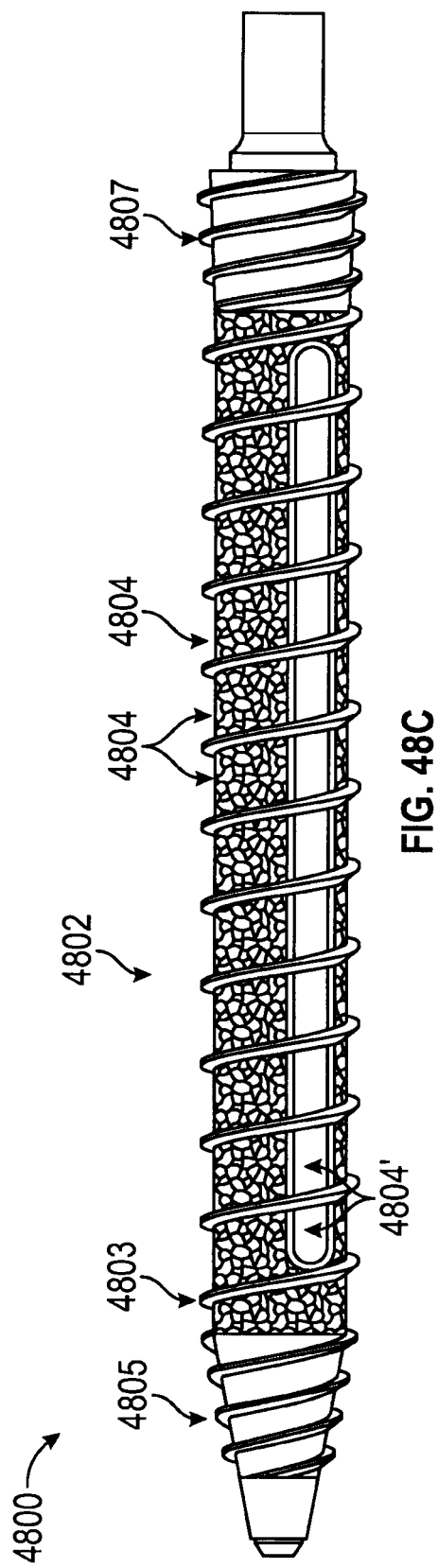
FIG. 48B
FIG. 48C

IMPLANTS FOR SPINAL FIXATION AND OR FUSION

CROSS REFERENCE TO RELATED APPLICATIONS

This application is a continuation of U.S. patent application Ser. No. 17/649,265, filed Jan. 28, 2022, which is a continuation of U.S. patent application Ser. No. 16/874,149, filed May 14, 2020, now U.S. Pat. No. 11,234,830, which is a continuation of International Application No. PCT/US2020/018402, filed Feb. 14, 2020, which claims the benefit to U.S. application Ser. No. 16/276,430, filed Feb. 14, 2019, now U.S. Pat. No. 11,369,419, U.S. Provisional Application No. 62/859,646, filed Jun. 10, 2019, and U.S. Provisional Application No. 62/933,250, filed Nov. 8, 2019; all of the disclosures of which are incorporated by reference herein for all purposes.

Incorporation by Reference

All publications and patent applications mentioned in this specification are herein incorporated by reference to the same extent as if each individual publication or patent application was specifically and individually indicated to be incorporated by reference. For example, this application incorporates by reference in their entireties U.S. Patent Publication No. 2011/0087294, U.S. Patent Publication No. 2011/0087296, U.S. Patent Publication No. 2011/0118785, and U.S. Patent Publication No. 2011/0125268.

FIELD

The present disclosure generally relates to bone implants. More specifically, the present disclosure relates to bone implants used for the stabilization, fixation and/or fusion of the sacroiliac joint and/or the spine.

BACKGROUND

Many types of hardware are available both for the fixation of bones that are fractured and for the fixation of bones that are to be fused (arthrodesed).

For example, the human hip girdle is made up of three large bones joined by three relatively immobile joints. One of the bones is called the sacrum and it lies at the bottom of the lumbar spine, where it connects with the L5 vertebra. The other two bones are commonly called "hip bones" and are technically referred to as the right ilium and-the left ilium. The sacrum connects with both hip bones at the sacroiliac joint (in shorthand, the SI-Joint).

The SI-Joint functions in the transmission of forces from the spine to the lower extremities, and vice-versa. The SI-Joint has been described as a pain generator for up to 22% of lower back pain.

To relieve pain generated from the SI-Joint, sacroiliac joint fusion is typically indicated as surgical treatment, e.g., for degenerative sacroiliitis, inflammatory sacroiliitis, iatrogenic instability of the sacroiliac joint, osteitis condensans ilii, or traumatic fracture dislocation of the pelvis. Currently, screws and screws with plates are used for sacroiliac fusion. At the same time the cartilage is generally removed from the "synovial joint" portion of the SI-Joint. This requires a large incision to approach the damaged, subluxed, dislocated, fractured, or degenerative joint.

Additionally, long constructs can be used to join, fuse and/or stabilize a plurality of vertebrae in the thoracic, lumbar, and sacral portions of the spine. These long constructs may include one or more rods. For example, to treat spinal disorders such as degenerative scoliosis, the L5 vertebra to the S1 vertebrae can be fused using a system of implants and rods as described herein.

SUMMARY OF THE DISCLOSURE

The disclosure herein generally relates to one or more of bone implants, their methods of use, or their methods of assembly. The implants herein may be used in one or both of the treatment of a SI-Joint, or as an anchoring component for a construct that joins, fuses and/or stabilizes vertebrae.

One aspect of the disclosure is an implant for use in at least one of bone fusion or stabilizing a plurality of bones. The implant includes a distal anchoring region and a growth region that is proximal to the distal anchoring region, the distal anchoring region having one or more distal surface features that adapt the distal anchoring region for anchoring into iliac bone, and the growth region includes one or more growth features that adapt the growth region to facilitate at least one of bony on-growth, in-growth, or through-growth.

The implant is optionally a composite implant. A composite implant may have an inner elongate member such as a shank and an outer elongate member such as a sleeve. An inner shank may have a distal end region with one or more threads sized and configured for anchoring into iliac bone. An outer sleeve can be sized and configured to be positioned over at least a portion of the inner shank. A sleeve may be positioned relative to an inner member to form a composite implant with an inner member interface feature and a sleeve interface feature interfacing each other so as to resist relative motion between the sleeve and the inner member in at least one direction.

A distal anchoring region can have one or more distal surface features that better adapt the distal anchoring region for anchoring into iliac bone than the growth region, and the growth region can have one or more growth features that better adapt the growth region to facilitate at least one of bony on-growth, in-growth, or through-growth than the anchoring region.

An inner member (e.g. an inner shank) may be more resistant to fatigue than an outer member (e.g. an outer sleeve).

The implants herein are optionally not composite implants.

One aspect of the disclosure herein includes a method of implanting an implant, optionally a composite implant, for use in at least one of fusing or stabilizing bony tissue. The method includes advancing the implant along a posterior sacral alar-iliac ("SAI") trajectory until a distal anchoring region is disposed in iliac bone and growth region is disposed across the SI Joint. The method can include coupling a tulip or other coupling member to the implant, and optionally coupling a construct member (e.g. rod), to the tulip.

One aspect of the disclosure is a method of assembling a composite bone implant for use in one or more of fusing or stabilizing bone. The method includes positioning an outer member (e.g. sleeve) such that the outer member is disposed over an inner member (e.g. inner shank). Forming the composite implant may include forming a composite implant such that an inner member (e.g. shank) interface feature and a sleeve interface feature interface each other so as to resist relative motion between the sleeve and the inner member in at least one direction. A composite implant may have a distal anchoring region and a growth region that is proximal to the distal anchoring region, the distal anchoring region optionally having one or more distal surface features that better adapt the distal anchoring region for anchoring into iliac bone than the growth region, and the growth region optionally having one or more growth features that better adapt the growth region to facilitate at least one of bony on-growth, in-growth, or through-growth than the anchoring region.

One aspect of the disclosure is an inner shank that can be used as part of a composite bone implant. The inner shank can include any of the features described or claimed herein.

One aspect of the disclosure is an outer sleeve that can be used as part of a composite bone implant. The outer sleeve can include any of the features described or claimed herein.

In some merely exemplary embodiments, an implant for use in fusing and or stabilizing a plurality of bones is provided with a shank portion, a body portion and a head portion. The shank portion has a proximal end and a distal end. The body portion is coupled to the shank portion and is configured to be placed through a first bone segment, across a bone joint or fracture and into a second bone segment. The body portion is configured to allow for bony on-growth, ingrowth and through-growth. The head portion is coupled to the proximal end of the shank portion and is configured to couple the shank portion to a stabilizing rod.

A body portions as used in this context may include any of the sleeves herein.

In some embodiments of the above implants, the distal end of the shank portion is provided with threads for securing the implant to the second bone segment. In some embodiments, the first bone segment is a sacrum and the second bone segment is an ilium. The body portion may be integral with the shank portion. The body portion may include at least one rectilinear face to prevent rotation. In some embodiments, the body portion has a cross-section transverse to a longitudinal axis that is triangular in shape to prevent rotation. The body portion may include at least one apex to prevent rotation. In some embodiments, the body portion includes a plurality of fenestrations that each communicate with a central lumen of the body portion. The shank portion may include at least one spline that mates with a slot within the body portion to prevent relative rotation between the shank portion and the body portion.

In some embodiments, an implant for use in fusing and or stabilizing a plurality of bones is provided with a shank portion, a body portion and a head portion. The shank portion has a proximal end and a distal end. The body portion is coupled to the shank portion and is configured to be placed into a first bone segment. The body portion is configured to allow for bony on-growth, ingrowth and through-growth. The head portion is coupled to the proximal end of the shank portion and is configured to couple the shank portion to a stabilizing rod.

In some embodiments, the first bone segment is a vertebra, a sacrum or an ilium. The distal end of the shank portion may be provided with threads for securing the implant to the second bone segment. In some embodiments, the body portion is integral with the shank portion. In some embodiments, the body portion includes at least one rectilinear face to prevent rotation. The body portion may have a cross-section transverse to a longitudinal axis that is triangular in shape to prevent rotation. In some embodiments, the body portion includes at least one apex to prevent rotation. The body portion may include a plurality of fenestrations that each communicate with a central lumen of the body portion. In some embodiments, the shank portion includes at least one spline that mates with a slot within the body portion to prevent relative rotation between the shank portion and the body portion. The distal end of the shank portion may be provided with a plurality of bristles to allow the shank portion to be distally inserted into a bone but inhibit proximal removal from the bone.

One aspect of the disclosure is an implant for use in at least one of fusing or stabilizing bony tissue, comprising: an elongate body sized and configured such that the elongate body can be implanted across a sacro-iliac ("SI") joint and extend into a sacrum and into an ilium (optionally to or beyond a tear-drop shaped region); a distal anchoring region of the elongate body having one or more distal surface features that are configured to anchor the distal anchoring region to iliac bone, and a proximal region of the elongate body disposed proximal to the distal region, the proximal region having one or more proximal surface features adapted to allow at least one of bony on-growth, in-growth, or through-growth.

One aspect of this disclosure is a bone stabilizing implant, comprising: an elongate implant body; and one or more deployable members, the one or more deployable members each having a non-deployed position and a deployed position relative to the elongate implant body. An elongate implant body can include one or more threads, optionally a plurality of regions having different number of leads. An elongate implant can include a plurality of rows of openings (optionally linear rows), each of the rows including a plurality of openings separated by a portion of the elongate implant body. A portion of the elongate implant body that separates the plurality of openings can include one or more threads. Any of the deployable members can include a plurality of protrusions extending from a spine, the protrusions extending further radially outward than the spine, and optionally the protrusions formed integrally with the spine. One or more deployable members can be positioned relative to the elongate implant body such that they are deployed upon actuation of an internal deployment member. An internal deployment member can comprise a plurality of radially protruding camming surfaces that when rotated cause the one or more deployable members to move radially outward. One or more threads on an elongate implant body can provide a mechanical radial stop to one or more deployable members, optionally preventing the opening(s) from bowing under load. Any of the openings may be tapered to limit play between an elongate implant body and one or more deployable members. An elongate implant body can have one or more lattice sections.

BRIEF DESCRIPTION OF THE DRAWINGS

FIGS. 5 to 7A and 7B are anatomic views showing, respectively, a pre-implanted perspective, implanted perspective, implanted anterior view, and implanted craniocaudal section view, the implantation of three implant structures for the fixation of the SI-Joint using a lateral approach through the ilium, the SI-Joint, and into the sacrum.

FIGS. 10A and 10B illustrate an embodiment of an implant structure with an integrated head portion.

FIGS. 11A and 11B illustrate embodiments of an implant structure suitable for pedicle screw salvage.

FIG. 25B is an exploded view showing the components of the bone implant of FIG. 25A.

FIG. 25C is a side view showing the bone implant of FIG. 25A.

FIG. 25D is a top plan view showing the bone implant of FIG. 25A.

FIGS. 32A and 32B illustrate imaging showing an exemplary SAI trajectory for implanting a SI Joint stabilization implant across the SI joint, with the arrow indicating the trajectory.

FIG. 33A illustrates an exemplary composite implant.

FIGS. 41A and 41B illustrate portions of an exemplary composite implant.

FIGS. 45A and 45B illustrate an exemplary composite implant.

FIGS. 48A, 48B, 48C, 48D, 48E, 48F, 48G and 48H illustrate an exemplary implant with one or more deployable members.

DETAILED DESCRIPTION

Figure 1:
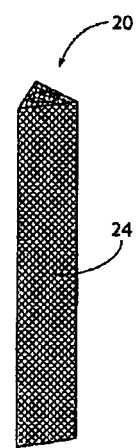
FIG. 1 illustrates an embodiment of an implant structure.
Figure 3:
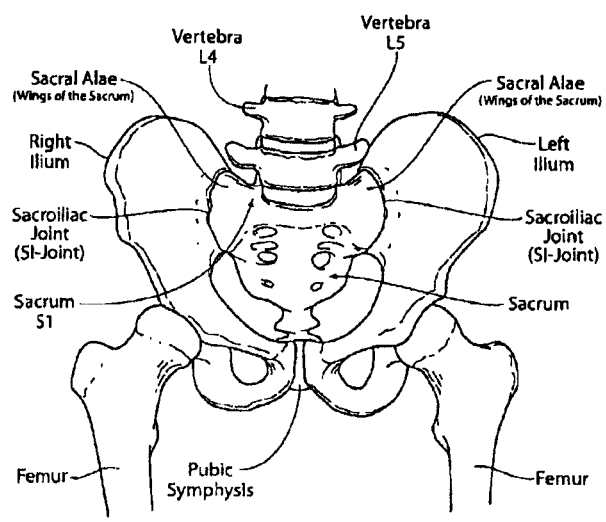
FIGS. 3 and 4 are, respectively, anterior and posterior anatomic views of the human hip girdle comprising the sacrum and the hip bones (the right ilium, and the left ilium), the sacrum being connected with both hip bones at the sacroiliac joint (in shorthand, the SI-Joint).
Figure 4:
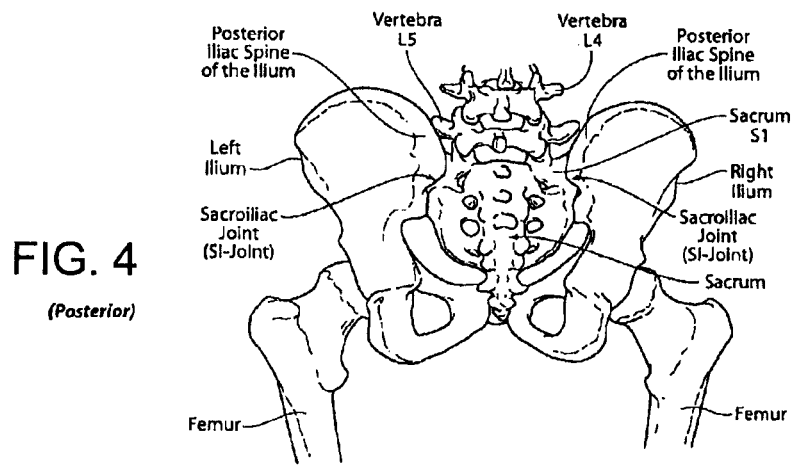

Elongated, stem-like implant structures 20 like that shown in FIG. 1 make possible the fixation of the SI-Joint (shown in anterior and posterior views, respectively, in FIGS. 3 and 4) in a minimally invasive manner. These implant structures 20 can be effectively implanted through the use a lateral surgical approach. The procedure is desirably aided by conventional lateral, inlet, and outlet visualization techniques, e.g., using X-ray image intensifiers such as C-arms or fluoroscopes to produce a live image feed, which is displayed on a TV screen.

In one embodiment of a lateral approach (see FIGS. 5, 6, and 7A/B), one or more implant structures 20 are introduced laterally through the ilium, the SI-Joint, and into the sacrum. This path and resulting placement of the implant structures 20 are best shown in FIGS. 6 and 7A/B. In the illustrated embodiment, three implant structures 20 are placed in this manner. Also in the illustrated embodiment, the implant structures 20 are rectilinear in cross section and triangular in this case, but it should be appreciated that implant structures 20 of other rectilinear cross sections can be used.

Before undertaking a lateral implantation procedure, the physician identifies the SI-Joint segments that are to be fixated or fused (arthrodesed) using, e.g., the Fortin finger test, thigh thrust, FABER, Gaenslen's, compression, distraction, and diagnostic SI-Joint injection.

Figure 2A:
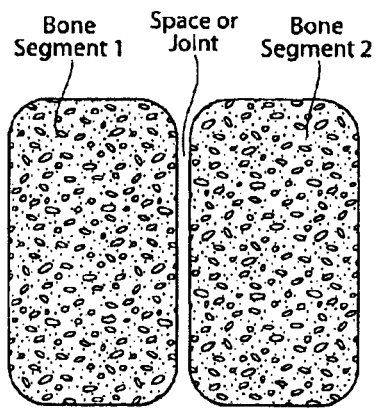
FIGS. 2A-2D are side section views of the formation of a broached bore in bone according to one embodiment of the invention.
Figure 2B:
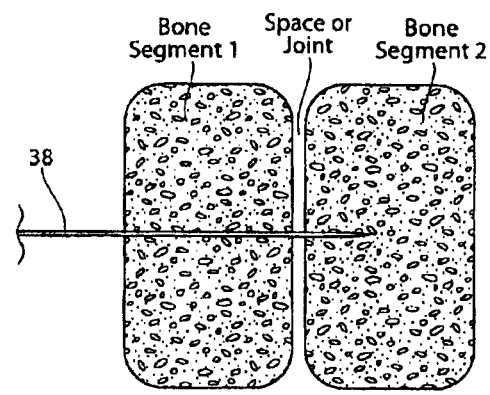

Aided by lateral, inlet, and outlet C-arm views, and with the patient lying in a prone position, the physician aligns the greater sciatic notches and then the alae (using lateral visualization) to provide a true lateral position. A 3 cm incision is made starting aligned with the posterior cortex of the sacral canal, followed by blunt tissue separation to the ilium. From the lateral view, the guide pin 38 (with sleeve (not shown)) (e.g., a Steinmann Pin) is started resting on the ilium at a position inferior to the sacrum end plate and just anterior to the sacral canal. In the outlet view, the guide pin 38 should be parallel to the sacrum end plate and in the inlet view the guide pin 38 should be at a shallow angle anterior (e.g., 15 degrees to 20 degrees off the floor, as FIG. 7B shows). In a lateral view, the guide pin 38 should be posterior to the sacrum anterior wall. In the outlet view, the guide pin 38 should be superior to the first sacral foramen and lateral of mid-line. This corresponds generally to the sequence shown diagrammatically in FIGS. 2A and 2B. A soft tissue protector (not shown) is desirably slipped over the guide pin 38 and firmly against the ilium before removing the guide pin sleeve (not shown).

Figure 2C:
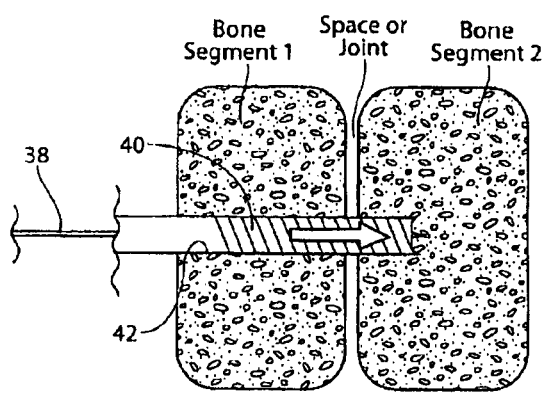

Over the guide pin 38 (and through the soft tissue protector), the pilot bore 42 is drilled in the manner previously described, as is diagrammatically shown in FIG. 2C. The pilot bore 42 extends through the ilium, through the SI-Joint, and into the S1. The drill bit 40 is removed.

Figure 2D:
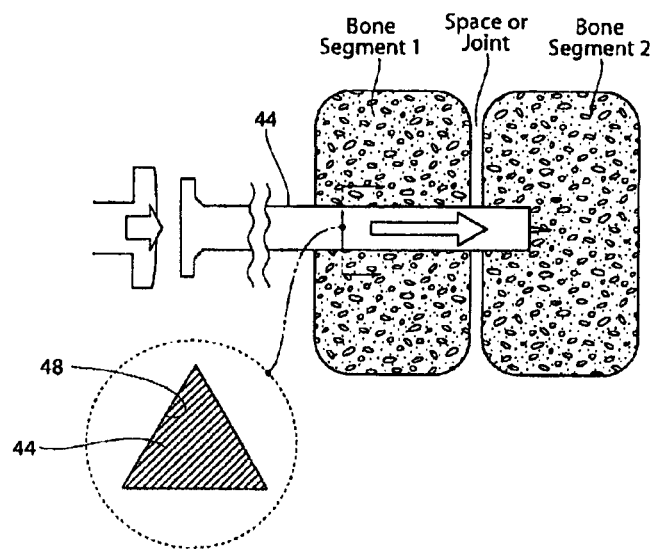

The shaped broach 44 is tapped into the pilot bore 42 over the guide pin 38 (and through the soft tissue protector) to create a broached bore 48 with the desired profile for the implant structure 20, which, in the illustrated embodiment, is triangular. This generally corresponds to the sequence shown diagrammatically in FIG. 2D. The triangular profile of the broached bore 48 is also shown in FIG. 5.

Figure 2E:
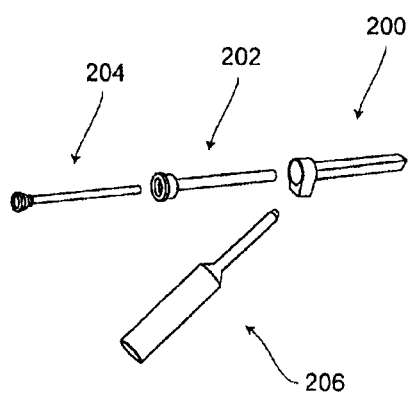
FIGS. 2E and 2F illustrate the assembly of a soft tissue protector system for placement over a guide wire.
Figure 2F:
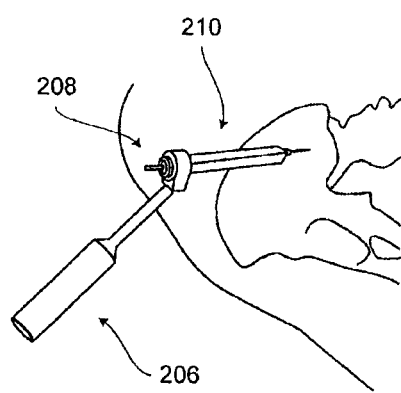

FIGS. 2E and 2F illustrate an embodiment of the assembly of a soft tissue protector or dilator or delivery sleeve 200 with a drill sleeve 202, a guide pin sleeve 204 and a handle 206. In some embodiments, the drill sleeve 202 and guide pin sleeve 204 can be inserted within the soft tissue protector 200 to form a soft tissue protector assembly 210 that can slide over the guide pin 208 until bony contact is achieved. The soft tissue protector 200 can be any one of the soft tissue protectors or dilators or delivery sleeves disclosed herein. In some embodiments, an expandable dilator or delivery sleeve 200 as disclosed herein can be used in place of a conventional soft tissue dilator. In the case of the expandable dilator, in some embodiments, the expandable dilator can be slid over the guide pin and then expanded before the drill sleeve 202 and/or guide pin sleeve 204 are inserted within the expandable dilator. In other embodiments, insertion of the drill sleeve 202 and/or guide pin sleeve 204 within the expandable dilator can be used to expand the expandable dilator.

In some embodiments, a dilator can be used to open a channel though the tissue prior to sliding the soft tissue protector assembly 210 over the guide pin. The dilator(s) can be placed over the guide pin, using for example a plurality of sequentially larger dilators or using an expandable dilator. After the channel has been formed through the tissue, the dilator(s) can be removed and the soft tissue protector assembly can be slid over the guide pin. In some embodiments, the expandable dilator can serve as a soft tissue protector after being expanded. For example, after expansion the drill sleeve and guide pin sleeve can be inserted into the expandable dilator.

Figure 5:
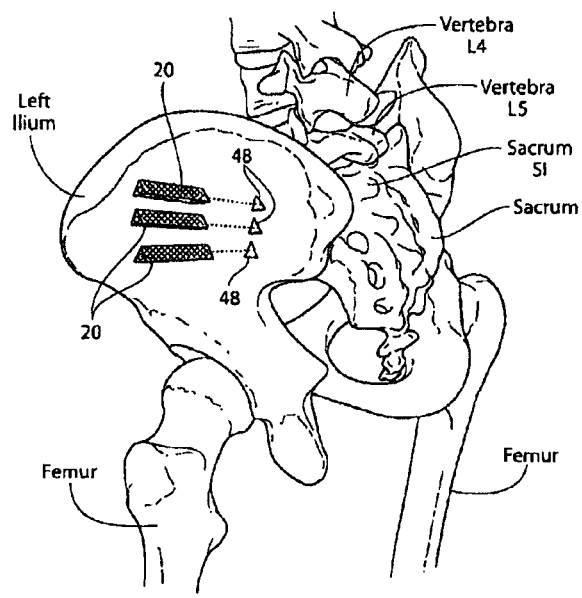
Figure 6:
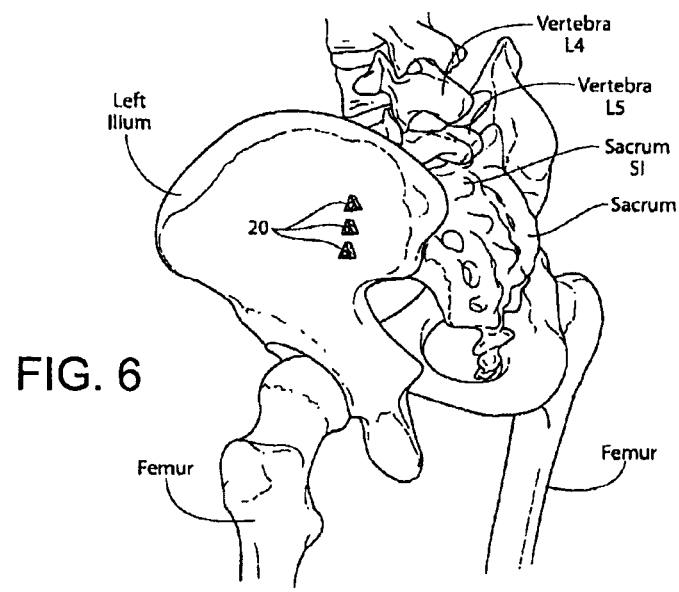
Figure 7A:
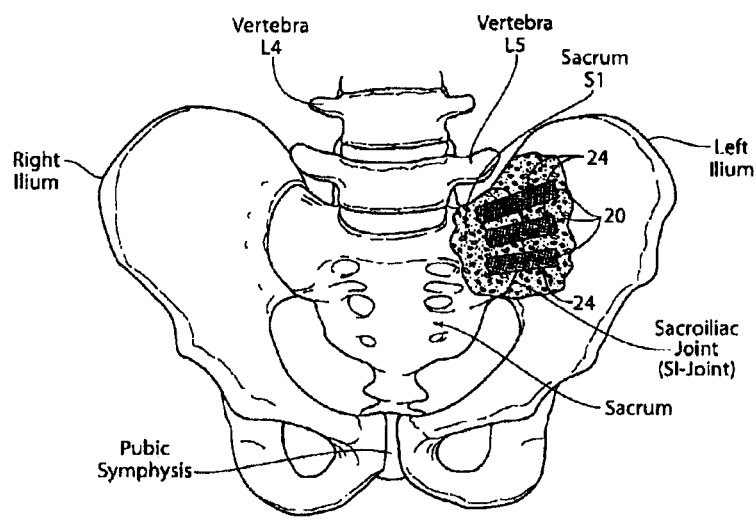
Figure 7B:
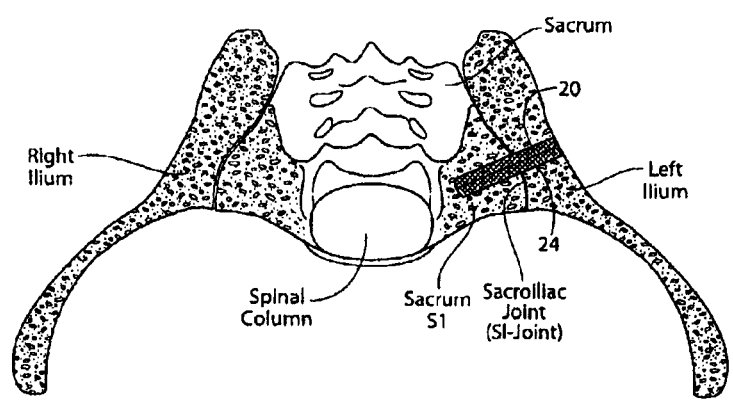

As shown in FIGS. 5 and 6, a triangular implant structure 20 can be now tapped through the soft tissue protector over the guide pin 38 through the ilium, across the SI-Joint, and into the sacrum, until the proximal end of the implant structure 20 is flush against the lateral wall of the ilium (see also FIGS. 7A and 7B). The guide pin 38 and soft tissue protector are withdrawn, leaving the implant structure 20 residing in the broached passageway, flush with the lateral wall of the ilium (see FIG. 7A and 7B). In the illustrated embodiment, two additional implant structures 20 are implanted in this manner, as FIG. 6 best shows. In other embodiments, the proximal ends of the implant structures 20 are left proud of the lateral wall of the ilium, such that they extend 1, 2, 3 or 4 mm outside of the ilium. This ensures that the implants 20 engage the hard cortical portion of the ilium rather than just the softer cancellous portion, through which they might migrate if there was no structural support from hard cortical bone. The hard cortical bone can also bear the loads or forces typically exerted on the bone by the implant 20.

The implant structures 20 are sized according to the local anatomy. For the SI-Joint, representative implant structures 20 can range in size, depending upon the local anatomy, from about 35 mm to about 60 mm in length, and about a 7 mm inscribed diameter (i.e. a triangle having a height of about 10.5 mm and a base of about 12 mm). The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone using, for example, plain film x-ray, fluoroscopic x-ray, or MRI or CT scanning.

Using a lateral approach, one or more implant structures 20 can be individually inserted in a minimally invasive fashion across the SI-Joint, as has been described. Conventional tissue access tools, obturators, cannulas, and/or drills can be used for this purpose. Alternatively, the novel tissue access tools described above and in co-pending U.S. Application No. 61/609,043, titled "TISSUE DILATOR AND PROTECTOR" and filed Mar. 9, 2012, which is hereby incorporated by reference in its entirety, can also be used. No joint preparation, removal of cartilage, or scraping are required before formation of the insertion path or insertion of the implant structures 20, so a minimally invasive insertion path sized approximately at or about the maximum outer diameter of the implant structures 20 can be formed.

The implant structures 20 can obviate the need for autologous bone graft material, additional pedicle screws and/or rods, hollow modular anchorage screws, cannulated compression screws, threaded cages within the joint, or fracture fixation screws. Still, in the physician's discretion, bone graft material and other fixation instrumentation can be used in combination with the implant structures 20.

In a representative procedure, one to six, or perhaps up to eight, implant structures 20 can be used, depending on the size of the patient and the size of the implant structures 20. After installation, the patient would be advised to prevent or reduce loading of the SI-Joint while fusion occurs. This could be about a six to twelve week period or more, depending on the health of the patient and his or her adherence to post-op protocol.

The implant structures 20 make possible surgical techniques that are less invasive than traditional open surgery with no extensive soft tissue stripping. The lateral approach to the SI-Joint provides a straightforward surgical approach that complements the minimally invasive surgical techniques. The profile and design of the implant structures 20 minimize or reduce rotation and micromotion. Rigid implant structures 20 made from titanium provide immediate post-op SI-Joint stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded SI-Joint.

To improve the stability and weight bearing capacity of the implant, the implant can be inserted across three or more cortical walls. For example, after insertion the implant can traverse two cortical walls of the ilium and at least one cortical wall of the sacrum. The cortical bone is much denser and stronger than cancellous bone and can better withstand the large stresses found in the SI-Joint. By crossing three or more cortical walls, the implant can spread the load across more load bearing structures, thereby reducing the amount of load borne by each structure. In addition, movement of the implant within the bone after implantation is reduced by providing structural support in three locations around the implant versus two locations.

In some embodiments, the implant structure can function like a pedicle screw to allow fixation and/or fusion of bone such as the spine and/or SI-Joint. For example, long constructs can be used to join, fuse and/or stabilize a plurality of vertebrae in the thoracic, lumbar, and sacral portions of the spine. For example, to treat spinal disorders such as degenerative scoliosis, the L5 vertebra to the S1 vertebrae can be fused using a system of implants and rods as described herein. As illustrated in FIGS. 8A-18E, the implant structure can include a stem portion and a head portion. The stem portion can be formed similarly to the SI-Joint implants described herein and in co-pending U.S. Patent Application Publication 2013/0296953, filed May 6, 2013, titled "Fenestrated Implant" and U.S. Pat. No. 8,202, 305 titled "Systems and Method for the Fixation or Fusion of Bone." A tulip or saddle structure can be attached to the head portion, and a rod can be inserted into and fixed to a plurality of tulip structures attached to implanted implant structures, thereby fusing and/or stabilizing the spine and/or other bones. In some embodiments, the stem portion, head portion, and tulip or saddle structure can all be cannulated and have a lumen that extends longitudinally through the assembled structure such that the assembled structure can be disposed over a guidewire or guide pin.

Figure 8C:
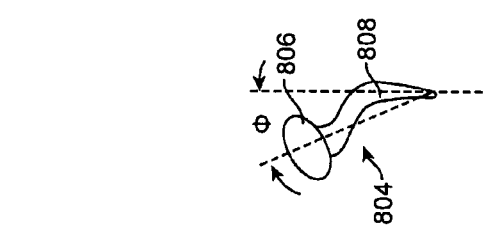
FIGS. 8A to 8C illustrate embodiments of an implant structure with a head portion joined using a Morse taper.
Figure 8B:
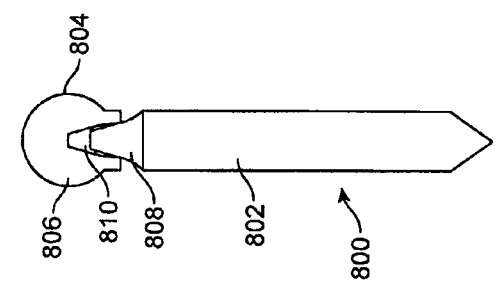
Figure 8A:
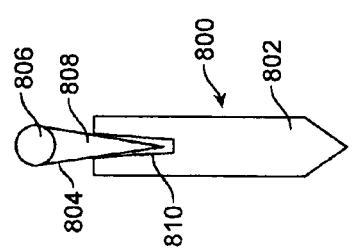

In some embodiments, as illustrated in FIGS. 8A-8C, the head portion 804 can be separate from the stem portion 802. For example, FIGS. 8A-8C illustrate embodiments of the implant structure 800 with a machine taper such as a Morse Taper. In some embodiments as illustrated in FIG. 8A, the head portion 804 can have a ball portion 806 and a tapered shank 808. The tapered shank 808 can fit into a corresponding tapering cavity 810 in the stem portion 802 to form a taper lock that is held together by friction. The length of the tapered shank 808 can be varied, making the distance between the ball portion 806 and proximal end of the stem portion 802 variable.

In some embodiments as illustrated in FIG. 8B, the head portion 804 can have a tapering cavity 810 while the stem portion 802 can have a tapered shank 808 extending from the proximal end of the stem portion 802. The length of the tapered shank 808 can be varied so that the distance between the head portion 804 and stem portion 802 can be adjusted as desired. In some embodiments, the tapered shank 808 of the stem portion 802 can be angled or curved with respect to the longitudinal axis of the stem portion 802. A curved tapered shank 808 can be useful as described below for the embodiment shown in FIG. 8C.

In some embodiments as illustrated in FIG. 8C, the head portion 804 can have a ball portion 806 and a tapered shank 808 that is curved or angled such that the distal portion of the tapered shank 808 is offset or angled with respect to the ball portion 806 and proximal portion of the tapered shank 808. A curved tapered shank 808 can be useful when a suitable implantation location in one or more bones is not aligned with the other implantation locations. In order for the implant structures 800 to line up with the stabilizing rod, a curved tapered shank 808 can be used so that the head portions 806 all line up with the stabilizing rod even if the implantation locations do not line up.

Figure 9:
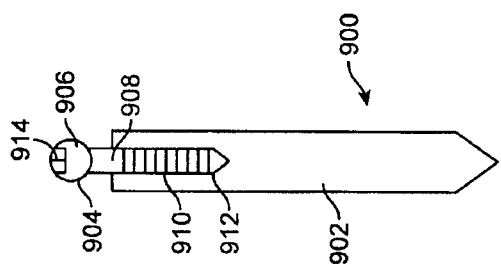
FIG. 9 illustrates an embodiment of an implant structure with a head portion joined using a screw type attachment.

FIG. 9 illustrates another embodiment of an implant structure 900 with a stem portion 902 and a head portion 904. The head portion 904 can have a ball portion 906 and a shank 908. The shank 908 can have threads 910, like a screw, that can be screwed into a cavity 912 with complementary internal threads. The ball portion 904 can have a screw drive 914 that facilitates turning of the head portion

904. The screw drive 914 can be a slot, socket (square, hex, star, etc.), or other typical screw drive 914 mechanism.

FIGS. 10A and 10B illustrate embodiments of integrated implant structures 1000 having a stem portion 1002 and a head portion 1004 that is integral with the stem portion 1002. As shown in FIGS. 10A and 10B, the head portion 1004 is integral or fixed to the stem portion 1002, and therefore the head portion 1004 has a fixed length relative to the stem portion 1002. As shown in FIG. 10A, the head portion 1004 can have a ball portion 1006 that can be attached to a tulip portion that is described in further detail below in, for example, FIGS. 13A and 18A-18C. Alternatively, as shown in FIG. 10B, the head portion 1004 can have a tulip portion 1007 integrated directly with the stem portion 1002. Having an integrated implant structure 1000 can be useful when it is known in advance that an implant structure 1000 will be used in, for example, a fixation or stabilization procedure that requires the use of an implant structure with a head portion 1004. The integrated implant 1000 can reduce procedure time by not requiring the attachment of the head portion 1004 onto the stem portion 1002. In addition, because the head portion 1004 is integral with the stem portion 1002, the integrated implant 1000 may have a greater structural integrity or strength than an implant assembled from separate pieces.

In some embodiments that may be particularly suited for pedicle screw salvage as illustrated in FIGS. 11A and 11B, the implant structure 1100 can have a stem portion 1102 with ledges or fenestrations 1003 that promote bone ingrowth. Examples of fenestrations that can be incorporated into the implant structure 1100 are described in co-pending U.S. Patent Application Publication 2013/0296953, filed May 6, 2013, titled "Fenestrated Implant." In some embodiments, the outer surface and/or structure of the stem portion 1102 can be twisted. In some embodiments, the stem portion 1102 may have a round cross-section to better match the cavity within the bone after the old pedicle screw has been removed. In some embodiments, the stem portion 1102 can be tapered. The diameter, shape and profile of the stem portion 1102 can match the bone cavity. In some embodiments, the stem portion 1102 can be oval, round, square, triangular, or rectilinear. In some embodiments, the head portion 1104 can be attached to the stem portion 1102 as described above. For example, the head portion 1104 can be attached to the stem portion 1102 using a Morse taper or screw attachment, or the head portion 1104 can be integral with the stem portion. Pedicle screw salvage can be performed when an implant, such as a pedicle screw, becomes loose within the bone due to windshield wipering or butterflying effects caused by stresses exerted to the bone by the implant. The loose implant can be removed and then replaced by one of the implants described herein.

Figure 12:
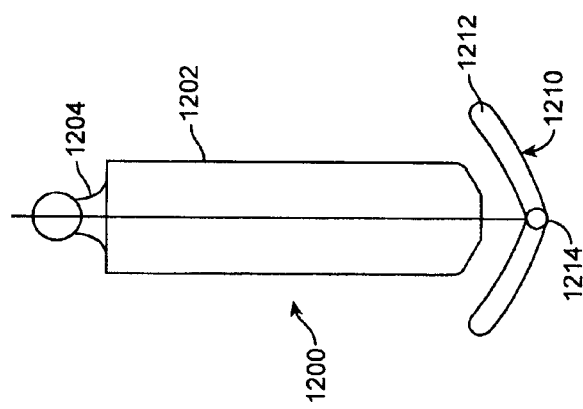
FIG. 12 illustrates an embodiment of an implant structure with an anchor.

FIG. 12 illustrates an implant structure 1200 with a stem portion 1202, a head portion 1204 attached to the proximal end of the stem portion 1202, and an anchor 1210 located distally the distal end of the stem portion 1202. The anchor 1210 can be folded into a collapsed configuration during insertion of the implant structure 1200 into bone, and then unfolded and/or expanded into an expanded configuration after insertion. In some embodiments, the anchor 1210 can have one or more arm portions 1212 that are foldable and/or expandable. In some embodiments, the anchor 1210 can be mechanically actuated from the collapsed configuration to the expanded configuration. In some embodiments, the arm portions 1212 can be joined at a hinge or a hub 1214. In some embodiments, the arm portions 12 can be expanded like the frame of an umbrella. In other embodiments, the anchor 1210 can be self-expanding and can be made of a shape memory material such as a nickel titanium alloy. In some embodiments, the anchor 1210 can be restrained by a sheath or other restraining element when in the collapsed configuration. In some embodiments, the anchor 1210 can be attached to and/or extend from the distal end of the stem portion 1202. The anchor 1210 can reduce or prevent implant structure 1200 migration after implantation.

Figure 13B:
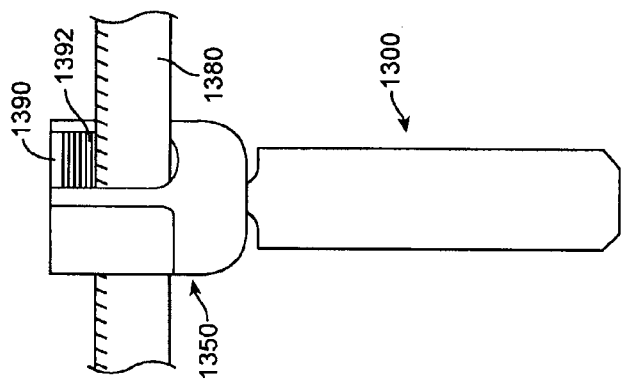
FIGS. 13A and 13B illustrate the attachment of a tulip structure to an implant structure and the securing of a rod to the tulip structure.
Figure 13A:
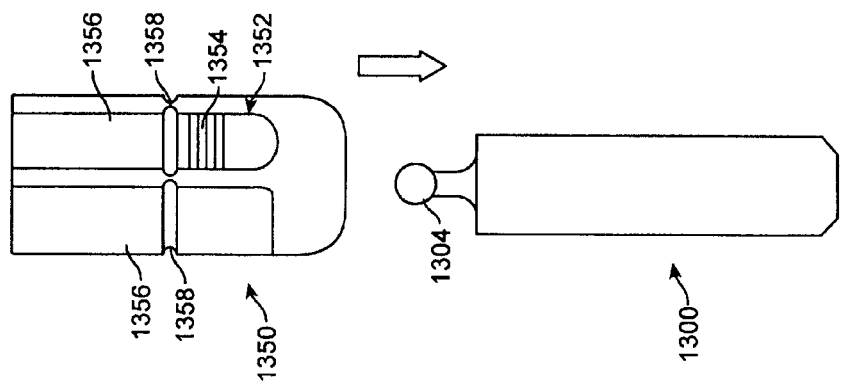

FIGS. 13A and 13B illustrate an implant structure 1300 and a corresponding tulip or saddle structure 1350 that can be attached to the head portion 1304 of the implant structure 1300. The tulip structure 1350 can have a slot 1352 for receiving a rod 1380 that can be used to stabilize the spine. In some embodiments, the tulip structure 1350 can have internal threading 1354 on the two wall portions 1356 that form the slot 1352. In some embodiments, a locking screw 1390 can be used to lock and secure the rod 1380 in place within the tulip structure 1350. The locking screw 1390 can have threading 1392 that correspond to the internal threading 1354 on the two wall portions 1356. To lock and secure the rod in place, the locking screw can simply be screwed in place over the rod 1380. The locking screw 1390 can have a screw drive similar to screw drive 914 described above with respect to FIG. 9. In other embodiments, other fastening mechanisms can be used in place of the locking screw 1390 to hold the rod in place. In some embodiments, the top portions of the wall portions 1356 can be snapped off along a break line 1358. In some embodiments, the break line 1358 can be formed by scoring or thinning the wall portions 1356 along the break line 1358. In some embodiments, the tulip structure 1350 does not have any break lines 1358 or excess wall portions 1356 that can be broken off and can instead have wall portions 1356 that are sized to receive the rod 1380 and locking screw 1390 without having excess material extending past the locking screw 1390.

Figure 14:
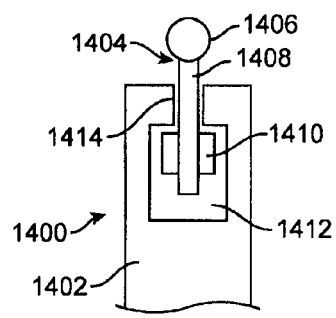
FIGS. 14 and 15 illustrate alternative embodiments of head portions with expandable attachment features.

FIG. 14 illustrates another embodiment of an implant structure 1400 having a stem portion 1402 with a cavity 1412 for receiving an expandable attachment 1410 on the shank 1408 of the head portion 1404. The expandable attachment 1410 on the shank 1408 can have a collapsed configuration and an expanded configuration. The entrance to the cavity 1412 can be a narrowed opening 1414 with a diameter less than the diameter of the cavity 1412. The shank 1408 can be inserted through the narrowed opening 1414 and into the cavity 1412 with the expandable attachment 1410 in the collapsed configuration. Once in the cavity 1412, the expandable attachment 1410 can expand into the expanded configuration, thereby securing the head portion 1404 to the stem portion 1402. The head portion 1404 can have a ball portion 1406 for connected to a tulip structure.

Figure 15:
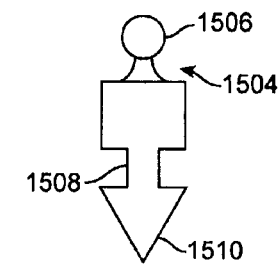

FIG. 15 illustrates another embodiment of a head portion 1504 that can be secured into a cavity 1412 in a stem portion 1402 similar to that illustrated in FIG. 14. The head portion 1504 can have a ball portion 1506 and a shank 1508 with narrowed or undercut portion 1508 and a tapered distal portion 1510. The tapered distal portion 1510 has an end that is narrow enough to be inserted into the narrowed opening 1414. As the tapered distal portion 1510 is further inserted through the narrowed opening 1414, the tapered distal portion 1510 forces the narrowed opening to open wider until the narrowed opening snaps into the undercut portion 1508 of the shank 1508, which in combination with the tapered distal portion 1510 in the cavity, functions to secure the head portion 1504 to the stem portion 1402.

Figure 16:
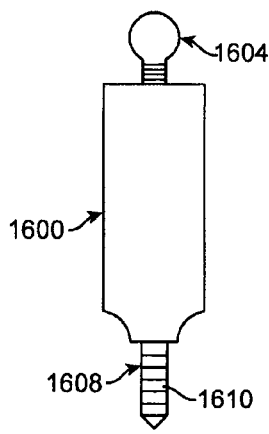
FIG. 16 illustrates an embodiment of an implant structure with a screw-like head portion that extends completely through the stem portion of the implant structure.

FIG. 16 illustrates another embodiment of a head portion 1604 than can be screwed into an implant structure 1600 in a similar manner as described in connection with FIG. 9, except that in this embodiment, the shank 1608 can have a length that allows the shank 1608 to extend completely through the implant structure 1600. Similarly to the embodiment described in FIG. 9, the shank 1608 can be threaded 1610 and a screw drive on the head portion 1604 can be used to turn the screw like shank 1608. In some embodiments, the threads 1610 on the proximal portion of the shank 1608 can be machine threads for engaging the corresponding threads in the implant structure 1600. The threads 1610 on the distal portion of the shank 1608 can be deeper than the machine threads, which allow the threads to better engage cancellous bone. In some embodiments, the pitch of the threads 1610 can be constant along the length of the shank 1608. In other embodiments, the pitch of the threads 1610 can vary between the different thread types.

Figure 17:
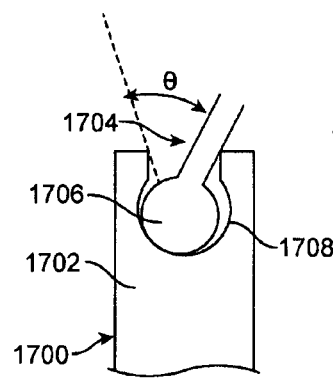
FIG. 17 illustrates an embodiment of the attachment of the head portion to the stem portion of the implant structure using a ball and socket joint.
Figure 18A:
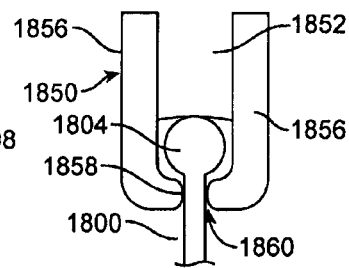
FIGS. 18A to 18E illustrate the head portion of the implant structure in connection with a tulip structure.
Figure 18B:
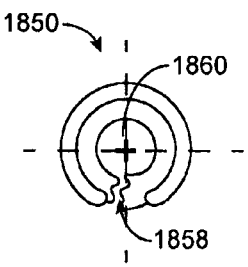
Figure 18C:
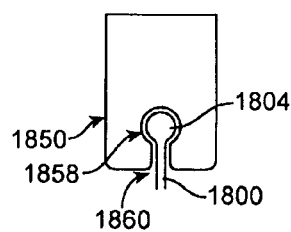
Figure 18D:
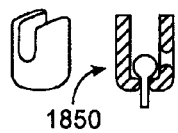
Figure 18E:
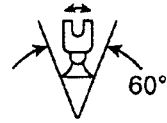

FIG. 17 illustrates another embodiment of the attachment of the stem portion 1702 of an implant structure 1700 to a head portion 1704. In this embodiment, the stem portion 1702 has a socket 1708 for receiving a corresponding ball 1706 on the distal end of the head portion 1704. The ball 1706 can reside in the socket 1708 to form a ball and socket joint that permits the head portion 1704 to be rotated through a predetermined angle of rotation. In some embodiments, the angle of rotation can be about 60 degrees or less. In other embodiments, the angle of rotation can be between about 30 to 90 degrees or less.

FIGS. 18A-18E illustrate embodiments of a snap-on tulip or saddle structure 1850. In some embodiments, the tulip structure 1850 can have a slot 1852 for receiving a rod that can be used to stabilize the spine or other bones. In some embodiments, the tulip structure 1850 can have internal threading on the two wall portions 1856 that form the slot 1852. In some embodiments, the wall portions 1856 can have extended tabs that can be snapped off and removed. In some embodiments, the tulip structure 1850 can have a head portion receiving slot 1858 shaped to receive the head portion 1804 attached to the implant structure 1800. The head portion receiving slot 1858 can be located on the distal end of the tulip structure 1850 and provides access to the internal cavity of the tulip structure 1850. The distal end of the tulip structure can have an opening 1860 that allows a portion of the implant structure 1800 to extend through. The diameter or size of the opening 1860 is less than the diameter or size of the head portion 1804, which allows the tulip structure 1850 to receive and then retain the head portion within the cavity of the tulip structure 1850. A stabilizing rod can then be fixed in place within the slot 1852 of the tulip structure 1850, thereby securing the head portion 1804 to the tulip structure 1850.

In some embodiments, the head portion receiving slot 1858 runs up both a portion of one of the side walls and the along the bottom portion to the opening 1860. In some embodiments, the upper portion of the head portion receiving slot 1858 can be circular in shape to accommodate the ball portion of the head portion 1804. The circular portion of the head portion receiving slot 1858 can be located a sufficient distance from the bottom portion of the tulip structure 1850 such that after the ball portion of the head portion 1804 passes into the cavity of the tulip structure 1850, the ball portion drops down against the bottom portion which prevents the ball portion from inadvertently sliding out of the tulip structure 1850. In order for the ball portion of the head portion 1804 to be removed from the tulip structure 1850, the ball portion must be raised from the bottom of the tulip structure 1850 until the ball portion is aligned with the circular portion of the head portion receiving slot 1858, and then the head portion 1804 can be removed from the tulip structure. In some embodiments, the portion of the head portion receiving slot 1858 on the bottom part of the tulip structure can be a straight slot. In other embodiments, the portion of the head portion receiving slot 1858 on the bottom part of the tulip structure can be a curved slot.

The shape and structure of the tulip structure 1850 cavity and opening 1860 allows the tulip structure 1850 to have about a 60 degree angle of movement and rotation after being attached to the head portion 1804. Such a tulip structure 1850 and head portion 1804 can be referred to as poly-axial, meaning the tulip structure 1850 can freely move within a conical area. In other embodiments, the angle of movement and rotation can be between about 30 to 90 degrees or less. Having a substantial angle of movement and rotation allows the implant structure 1800 to be inserted in a wider variety of angles while still allowing the tulip structure 1850 to be aligned with the rod for fixation.

Any of the implants described herein can be used in a variety of surgical procedures, such as stabilization, fixation or fusion of the sacroiliac joint and/or the spine, including vertebra and facet joints. In addition, surgical procedures using a posterior or a posterolateral approach will be particularly suitable for use with the implant structures described herein since the tulip structure of the implant will be aligned with the other implants along the spine after implantation. As described herein, these implant structures can be connected together using a rod that can be secured to each tulip structure. For simplicity, the following procedures will be illustrated and described using a general implant structure 20, but it is understood that any of the implant structures described herein can be used in place of the general implant structure 20.

Figure 19A:
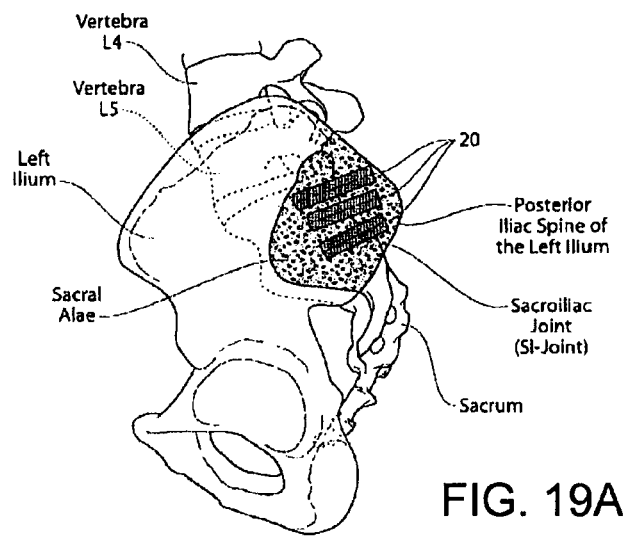
FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.
Figure 19B:
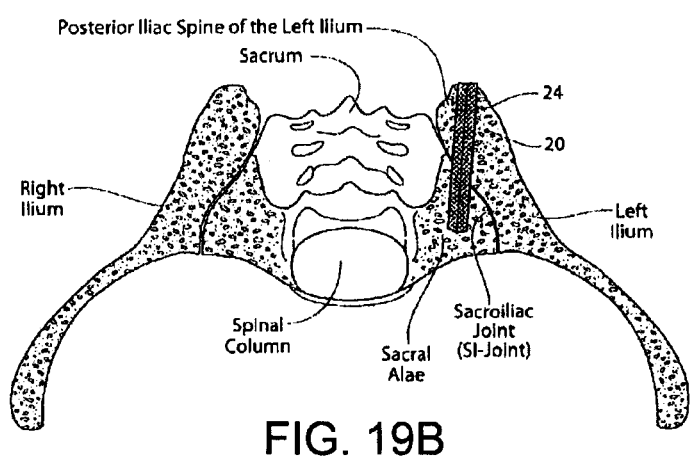

For example, FIGS. 19A and 19B illustrate a lateral view and an axial view of an embodiment of the implant structure crossing the SI-Joint using a posterolateral approach entering from the posterior iliac spine of the ilium, angling through the SI-Joint, and terminating in the sacral alae.

The posterolateral approach involves less soft tissue disruption that the lateral approach, because there is less soft tissue overlying the entry point of the posterior iliac spine of the ilium. Introduction of the implant structure 20 from this region therefore makes possible a smaller, more mobile incision. Further, the implant structure 20 passes through more bone along the posterolateral route than in a strictly lateral route, thereby involving more surface area of the SI-Joint and resulting in more fusion and better fixation of the SI-Joint. Employing the posterolateral approach also makes it possible to bypass all nerve roots, including the L5 nerve root.

The set-up for a posterolateral approach is generally the same as for a lateral approach. It desirably involves the identification of the SI-Joint segments that are to be fixated or fused (arthrodesed) using, e.g., the Faber Test, or CT-guided injection, or X-ray/MRI of SI-Joint. It is desirable performed with the patient lying in a prone position (on their stomach) and is aided by lateral and anterior-posterior (A-P) c-arms. The same surgical tools are used to form the pilot bore 42 over a guide pin 38, except the path of the pilot bore 42 now starts from the posterior iliac spine of the ilium, angles through the SI-Joint, and terminates in the sacral alae. The pilot bore 42 is shaped into the desired profile using a broach, as before described, and the implant structure 20 is inserted into the broached bore 48. The implant structure 20 is tapped through the soft tissue protector over the guide pin 38 from the posterior iliac spine of the ilium, angling through the SI-Joint, and terminating in the sacral alae, until the proximal end of the implant structure 20 is flush against the posterior iliac spine of the ilium. Because of the anatomic morphology of the bone along the posterolateral route, it may be advisable to introduce implant structures of difference sizes, with the most superior being the longest in length, and the others being smaller in length.

Figure 20A:
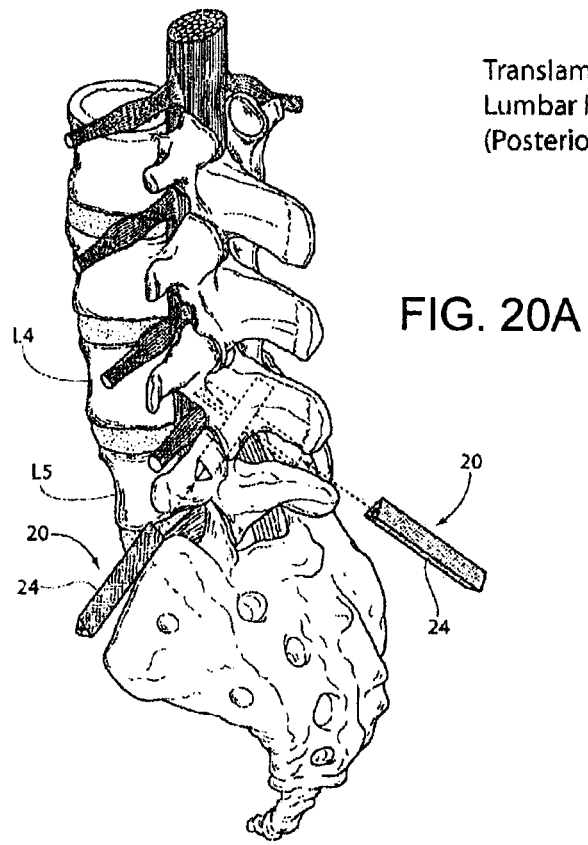
FIG. 20A is an anatomic posterior perspective view, exploded prior to implantation, of a representative configuration of an assembly of one or more implant structures, sized and configured to achieve translaminar lumbar fusion in a non-invasive manner and without removal of the intervertebral disc.
Figure 20B:
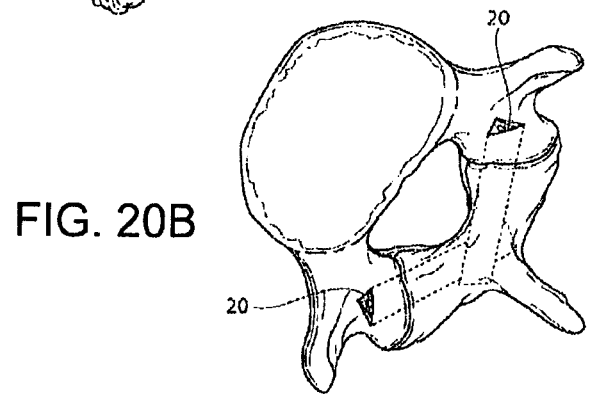
FIG. 20B is an anatomic inferior transverse plane view showing the assembly shown in FIG. 20A after implantation.

FIG. 20A shows, in an exploded view prior to implantation, a representative configuration of an assembly of one or more implant structures 20 sized and configured to achieve translaminar lumbar fusion in a non-invasive manner and without removal of the intervertebral disc. FIG. 20B shows the assembly after implantation, respectively, in an inferior transverse plane view.

As can be seen in the representative embodiment illustrated in FIGS. 20A and 20B, the assembly comprises two implant structures 20. The first implant structure 20 extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20 extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20 cross each other within the medial lamina of vertebra L4.

The first and second implant structures 20 are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A posterior procedure for implanting the assembly of implant structures 20 shown in FIGS. 20A and 20B comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to establish a desired implantation path through bone for the first (e.g., left side) implant structure 20, which, in FIGS. 20A and 20B, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 20A and 20B, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20 as for the left, and, after withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5. Of course, translaminar lumbar fusion between L5 and S1 can be achieved using first and second implant structures in the same manner.

Figure 21A:
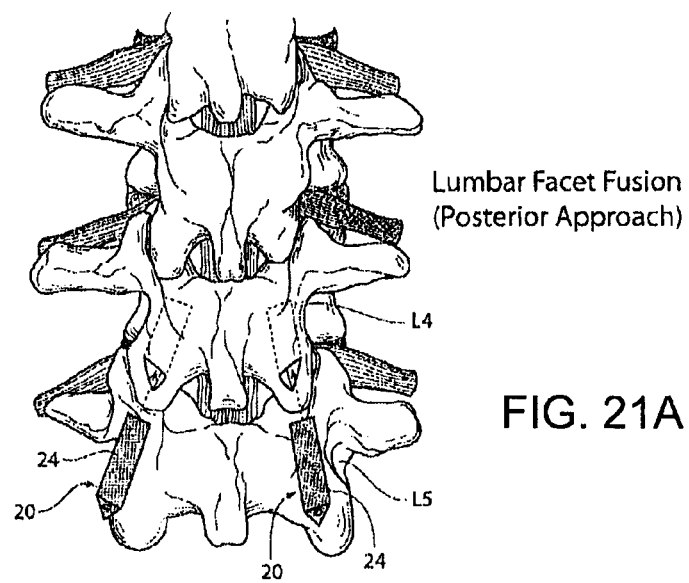
FIG. 21A is an anatomic posterior perspective view, exploded prior to implantation, of a representative configuration of an assembly of one or more implant structures, sized and configured to achieve lumbar facet fusion, in a non-invasive manner.
Figure 21B:
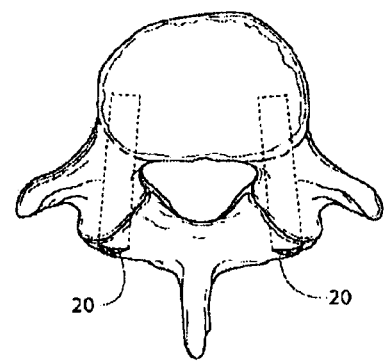
FIG. 21B is an anatomic inferior transverse plane view showing the assembly shown in FIG. 21A after implantation.
Figure 21C:
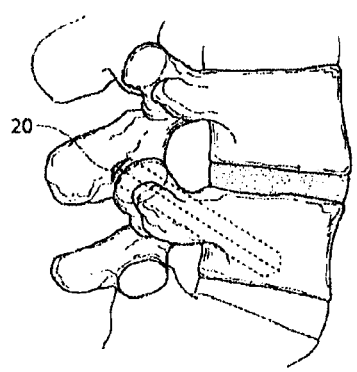
FIG. 21C is an anatomic lateral view showing the assembly shown in FIG. 21A after implantation.

FIG. 21A shows, in an exploded view prior to implantation, a representative configuration of an assembly of one or more implant structures 20 sized and configured to lumbar facet fusion, in a non-invasive manner and without removal of the intervertebral disc. FIGS. 21B and 21C show the assembly after implantation, respectively, in an inferior transverse plane view and a lateral view.

As can be seen in the representative embodiment illustrated in FIGS. 21A to 21C, the assembly comprises two implant structures 20. The first implant structure 20 extends from the left inferior articular process of vertebra L4, through the adjoining facet capsule into the left superior articular process of vertebra L5 and into the pedicle of vertebra L5. The second implant structure 20 extends from the right inferior articular process of vertebra L5, through the adjoining facet capsule into the right superior articular process of vertebra L5 and into the pedicle of vertebra L5. In this arrangement, the first and second implant structures 20 extend in parallel directions on the left and right pedicles of vertebra L5. The first and second implant structures 20 are sized and configured according to the local anatomy. The selection of lumbar facet fusion (posterior approach) is indicated when the facet joints are coronally angled. Removal of the intervertebral disc is not necessary, unless the condition of the disc warrants its removal.

A posterior procedure for implanting the assembly of implant structures 20 shown in FIGS. 21A to 21C comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 21A to 21C, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; and (viii) using a guide pin to establish a desired implantation path through bone for the second (e.g., right side) implant structure 20, which, in FIGS. 21A to 21C, traverses through the right inferior articular process of vertebra L4, through the adjoining facet capsule into the right superior articular process of vertebra L5 and into the pedicle of vertebra L5. The physician repeats the remainder of the above-described procedure sequentially for the right implant structure 20 as for the left and, withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5.

Of course, transfacet lumbar fusion between L5 and S1 can be achieved using first and second implant structures in the same manner.

Figure 22A:
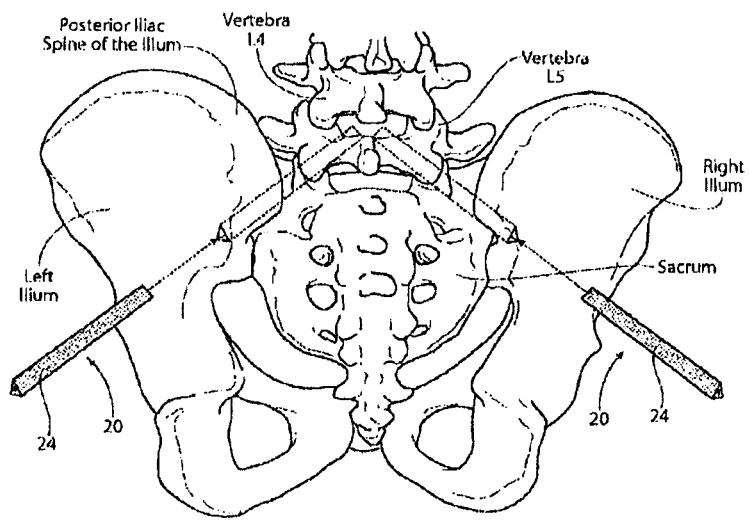
FIG. 22A is an anatomic posterior view showing, in an exploded view prior to implantation, another representative configuration of an assembly of one or more implant structures sized and configured to achieve fusion between lumbar vertebra L5 and sacral vertebra S1, in a non-invasive manner and without removal of the intervertebral disc, using a posterolateral approach entering from the posterior iliac spine of the ilium, angling through the SI-Joint, and terminating in the lumbar vertebra L5.
Figure 22B:
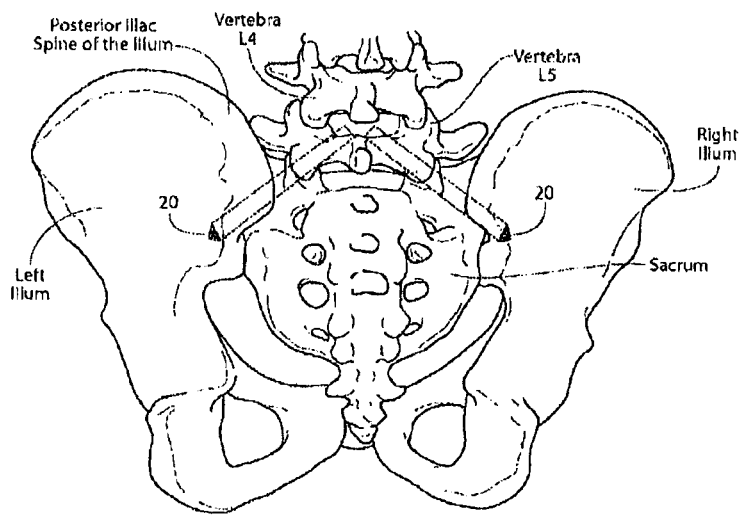
FIG. 22B is an anatomic posterior view showing the assembly shown in FIG. 22A after implantation.

FIG. 22A shows, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc. FIGS. 22B and 22C show the assembly after implantation.

As FIGS. 22A and 22B show, the one or more implant structures are introduced in a posterolateral approach entering from the posterior iliac spine of the ilium, angling through the SI-Joint into and through the sacral vertebra S1, and terminating in the lumbar vertebra L5. This path and resulting placement of the implant structures 20 are also shown in FIG. 22C. In the illustrated embodiment, two implant structures 20 are placed in this manner, but there can be more or fewer implant structures 20. Also in the illustrated embodiment, the implant structures 20 are triangular in cross section, but it should be appreciated that implant structures 20 of other cross sections as previously described can be used.

The posterolateral approach involves less soft tissue disruption than the lateral approach, because there is less soft tissue overlying the entry point of the posterior iliac spine of the ilium. Introduction of the implant structure 20 from this region therefore makes possible a smaller, more mobile incision.

The set-up for a posterolateral approach is generally the same as for a lateral approach. It desirably involves the identification of the lumbar region that is to be fixated or fused (arthrodesed) using, e.g., the Faber Test, or CT-guided injection, or X-ray/MRI of the L5-S1 level. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20 structure is inserted. The guide pin is withdrawn, and the procedure is repeated for the left implant structure 20, or vice versa. The incision site(s) are closed.

The assembly as described makes possible the achievement of trans-iliac lumbar fusion using a posterolateral approach in a non-invasive manner, with minimal incision, and without necessarily removing the intervertebral disc between L5 and S1.

Figure 23A:
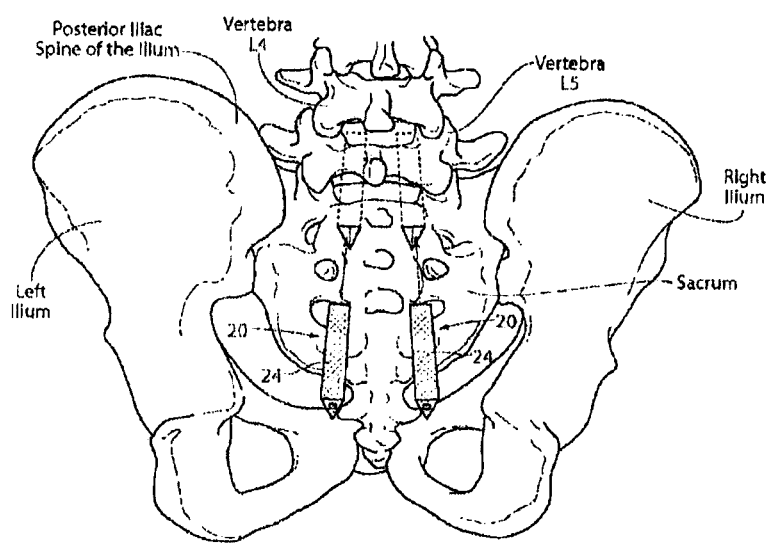
FIG. 23A is an anatomic anterior perspective view showing, in an exploded view prior to implantation, a representative configuration of an assembly of one or more implant structures, sized and configured to stabilize a spondylolisthesis at the L5/S1 articulation.
Figure 23B:
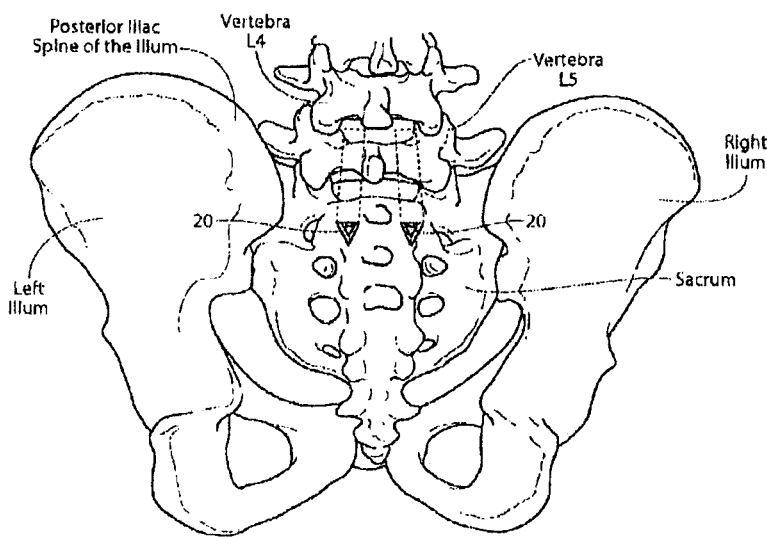
FIG. 23B is an anatomic anterior perspective view showing the assembly shown in FIG. 23A after implantation.
Figure 23C:
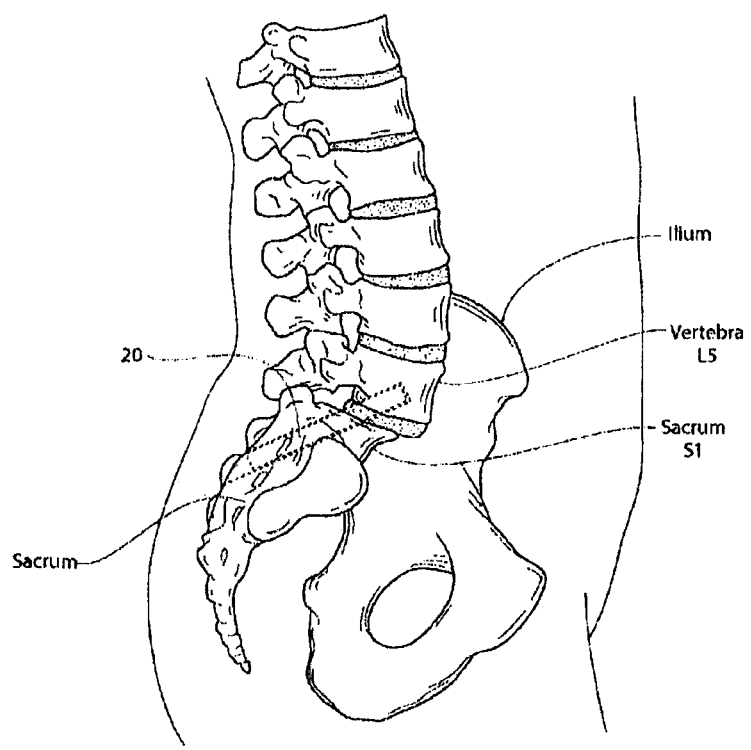
FIG. 23C is an anatomic lateral view showing the assembly shown in FIG. 23B.

FIG. 23A shows, in an exploded view prior to implantation, a representative configuration of an assembly of one or more implant structures 20 sized and configured to stabilize the spondylolisthesis at the L5/S1 articulation. FIGS. 23B and 23C show the assembly after implantation.

As shown, the implant structure 20 extends from a posterolateral region of the sacral vertebra S1, across the intervertebral disc into an opposite anterolateral region of the lumbar vertebra L5. The implant structure 20 extends in an angled path (e.g., about 20 degrees to about 40 degrees off horizontal) through the sacral vertebra S1 in a superior direction, through the adjoining intervertebral disc, and terminates in the lumbar vertebra L5.

A physician can employ a posterior approach for implanting the implant structure 20 shown in FIGS. 23A, 23B, and 23C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20, and withdrawing the guide pin. The incision site is then closed. As previously described, more than one implant structure 20 can be placed in the same manner to stabilize a spondylolisthesis.

The physician can, if desired, combine stabilization of the spondylolisthesis, as shown in FIG. 23A/B/C, with a reduction, realigning L5 and S-1. The physician can also, if desired, combine stabilization of the spondylolisthesis, as shown in FIG. 23A/B/C (with or without reduction of the spondylolisthesis), with a lumbar facet fusion, as shown in FIGS. 21A to 21C. The physician can also, if desired, combine stabilization of the spondylolisthesis, as shown in FIG. 23A/B/C, with a decompression, e.g., by the posterior removal of the spinous process and laminae bilaterally.

Figure 24:
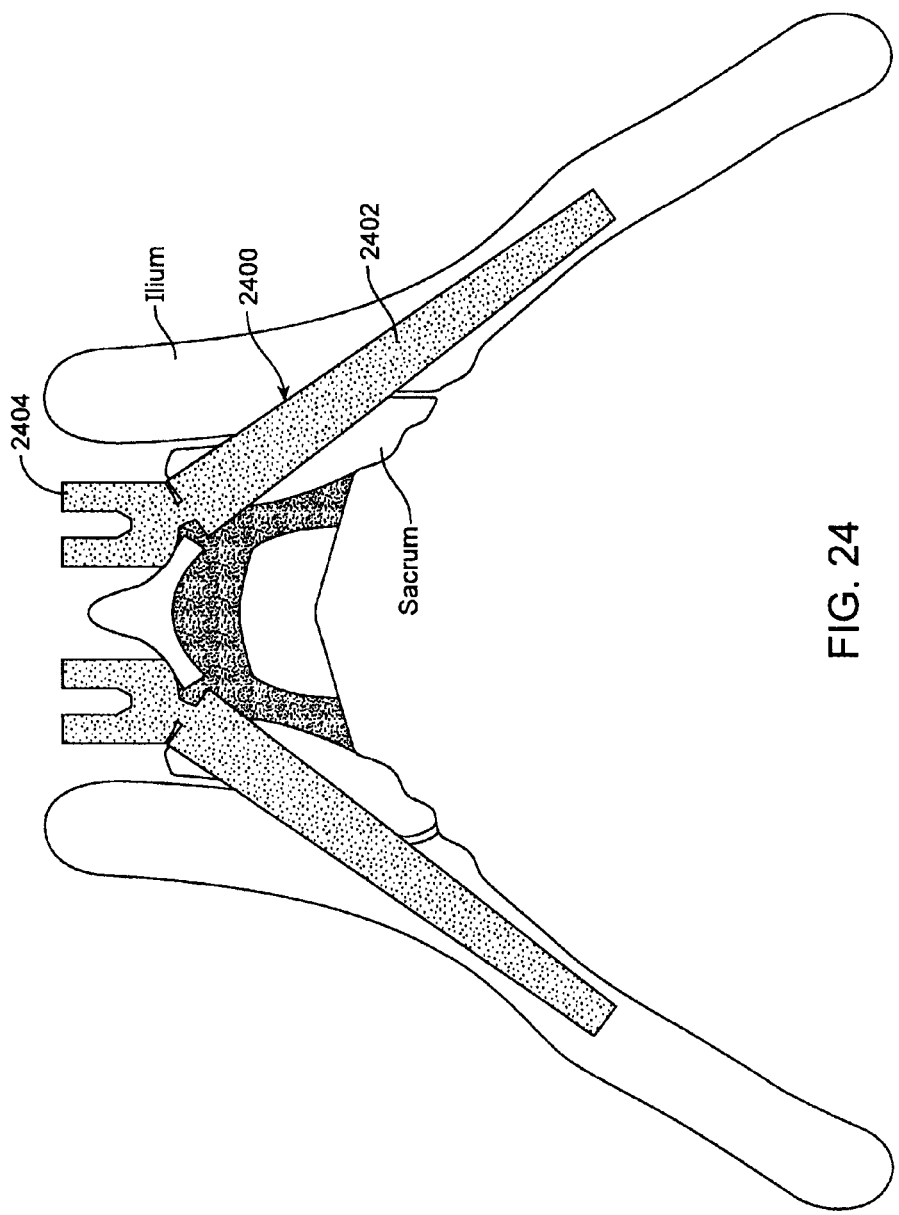
FIG. 24 is an axial view illustrating an implant inserted through a posteromedial approach.

In addition, in some embodiments as shown in FIG. 24, a posteromedial approach can be used to insert the implant 2400. For example, the implant 2400 can be inserted through the posterolateral sacrum, across the alae, through the SI-joint, and into the ilium where the implant may terminate. As illustrated, the implant 2400 can have a stem portion 2402 that is inserted into the bone and a tulip portion 2404 (which may be a separate component coupled to the implant in any of the examples herein) that remains outside the bone. In some particular implementations, a particular posteromedial approach may be used which is known as an S2 alar-iliac (S2AI) approach. The entry point for the S2AI approach is located at the midpoint between the S1 and S2 foramen and 2 mm medial to the lateral sacral crest. The guidewire and or implant should be placed across the sacro-iliac joint above the superior rim of the sciatic notch.

Any of the implants herein, including any of the composite implants herein, may be implanted based on the general illustration in FIG. 24.

In some implementations, just one implant is placed across each SI-joint using an S2AI trajectory, as depicted in FIG. 24. In other implementations, an implant can be added above and or below each S2AI implant using a lateral approach through the ilium, the SI-Joint, and into the sacrum, such as depicted in FIGS. 6A-7B.

It should be noted that, according to aspects of the present disclosure, a tulip, saddle structure, poly-axial joint, fastening mechanism or other coupling device (such as shown in FIGS. 13A and 13B) can be coupled to the proximal end of any number of bone anchors. For example, a coupling device may be attached to the proximal end of any of the implants previously shown in this disclosure, such as those shown in FIGS. 1 and 8A-18E, to allow the implant to couple with a spinal rod or construct, such as rod 1380 shown in FIG. 13B. In a similar manner, a coupling device may be located on the proximal end of the implant shown in FIGS. 1-2 or the implant shown in FIGS. 31-34 of U.S. Pat. No. 8,734,462. In some embodiments, a coupling device may be attached to the proximal end of any of the implants shown in FIGS. 1B-2B, 9A-9B and 10A-10B of U.S. Patent Application Publication 2013/0245763. In some embodiments, a coupling device may be attached to the proximal end of any of the implants shown in FIGS. 47-49 of U.S. Patent Application Publication 2017/0007409. In some embodiments, a coupling device may be attached to the proximal end of the implant shown in FIG. 12 of U.S. Pat. No. 9,662,157. In some embodiments, a coupling device may be attached to the proximal end of any of the implants shown in FIGS. 7A-9B of U.S. Patent Application Publication 2016/0081810. In some embodiments, a coupling device may be attached to the proximal end of any of the implants shown in FIGS. 11-27 of U.S. Patent Application 62/649,466. In some embodiments, the proximal ends of two or more implants may be joined together with a bridging structure that includes a coupling device for attaching to a spinal rod. In some embodiments, an implant can resemble a staple with two or more prongs for inserting into bone, the implant having a coupling device located on its proximal end.

Figure 25A:
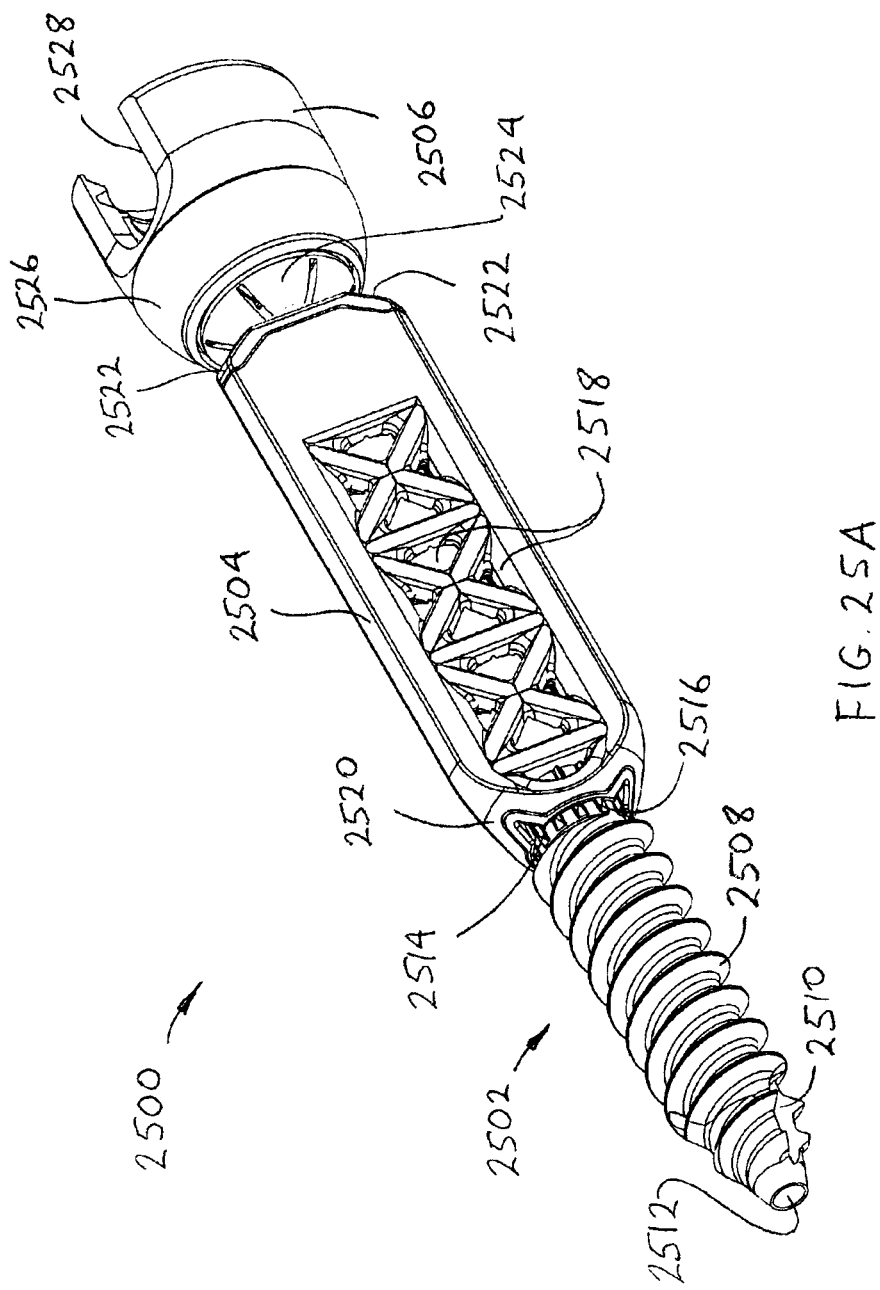
FIG. 25A is a perspective view showing an exemplary embodiment of a bone implant having a tulip or coupling device provided at its proximal end.
Figure 25E:
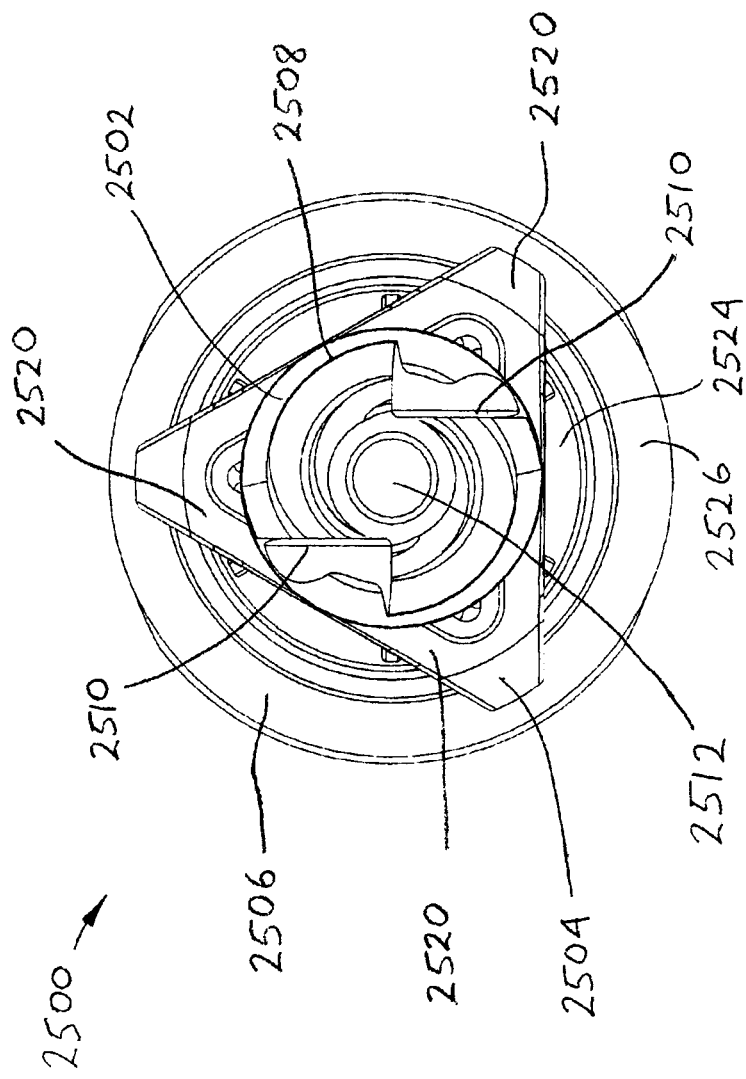
FIG. 25E is a distal end view showing the bone implant of FIG. 25A.

FIGS. 25A-25G show another exemplary embodiment of a bone implant having a tulip or coupling device provided at its proximal end (which can be a separate component secured to the implant in a separate tulip coupling step). As best seen in FIG. 25B, implant 2500 includes a shank portion 2502, a body portion 2504 (which may be referred to herein as a sleeve) and a head portion 2506. Any of the head portions herein may be referred to generally as a tulip, may be a separate component than the implant, and can be secured to the implant after the implant has been implanted in place. In this embodiment, the distal end of shank portion 2502 includes threads 2508 for threading the shank portion 2502 into a bone segment. Threads 2508 may include one or more self-tapping cutouts 2510, as best seen in FIG. 25E. The proximal end of shank portion 2502 may be provided with a hexagonal recess (not shown) or other suitable feature to mate with a driver to screw the shank portion 2502 into the bone segment. A central lumen 2512 may be provided along the longitudinal axis of shank portion 2502 to allow it to be placed over a guidewire or guide pin when being implanted.

In this embodiment, body portion 2504 is provided with a central lumen 2514 configured to slide over the proximal end of shank portion 2502. Radially outward extending splines 2516 may be provided at one or more locations on shank portion 2502, as best seen in FIG. 25B, to mate with corresponding grooves along the inner surface of central lumen 2514. Splines 2516 and/or other non-rotating features may be provided on shank portion 2502 and body portion 2504 to prevent the two parts from rotating relative to one another. Splines 2516 and or their corresponding grooves may be tapered to create a tight fit when body portion 2504 is tapped into place over shank portion 2502. Splines may be omitted in the middle of shank portion 2502 as shown to reduce stress concentrations and thereby increase fatigue properties of the implant. In other embodiments (not shown), these non-rotation features may be omitted to permit body portion 2504 to rotate relative to shank portion 2502.

In this embodiment, body portion 2504 has a triangular cross-section to prevent it from rotating relative to surrounding bone. When body portion 2504 is placed across a joint or fracture between two bone segments as previously described, body portion 2504 inhibits the two bone segments from rotating or translating relative to one another. In other embodiments (not shown), the body portion may have a square, rectangular, oval or other cross-sectional shape with at least one rectilinear face and/or at least one apex to similarly prevent rotation. When body portion 2504 is prevented from rotating relative to the surrounding bone by virtue of its non-rotationally shaped cross-section, and when splines 2516 prevent shank portion 2502 from rotating relative to body portion 2504, shank portion 2502 is prevented from rotating relative to the surrounding bone. This arrangement prevents shank portion 2502 from undesirably backing out or migrating further into the bone.

Body portion 2504 may be provided with fenestrations 2518 to allow for bony on-growth, in-growth and through-growth. In this exemplary embodiment, a repeating pattern of spars and cross-struts creates a plurality of triangularly shaped fenestrations on each face of body portion 2504. Each of the fenestrations 2518 opens into the central lumen 2514 of body portion 2504. In some embodiments, body portion 2504 is fabricated using an additive manufacturing process such as 3D printing. Further information on designing and manufacturing fenestrated implants is provided in the applicant's U.S. Pat. No. 9,662,157, filed Sep. 18, 2015, and titled "Matrix Implant." The distal end of body portion 2504 may also be provided with tapered and rounded leading edges 2520 as shown to facilitate inserting body portion 2504 into one or more bone segments. Trailing edges 2522 having a lesser degree of taper may be provided on the proximal end of body portion 2504 as shown to facilitate removal of body portion 2504 from the bone, if desired. Having less taper on trailing edges 2522 permits better engagement between the proximal end and surrounding cortical bone surfaces.

Head portion 2506 may be provided with a coupler 2524 and a main body 2526 as shown in FIGS. 25A-25E, and a nut (not shown). The nut has external threads that mate with internal threads located in the proximal recess of main body 2526 to tighten a spinal rod (not shown) against the bottom of channels 2528 in main body 2526. As shown in FIG. 25B, the proximal end of shank portion 2502 may be provided with a circumferential rib or barb 2530 for securing head portion 2506 to shank portion 2502 in a snap-fit manner. In some embodiments, main body 2526 is configured to pivot in a poly-axial or spherical manner relative to coupler 2524 and shank portion 2502. In some embodiments, main body 2526 is configured to spin about its main axis relative to coupler 2524 and shank portion 2502. In some embodiments, main body 2526 is configured to immovable relative to coupler 2524 and/or shank portion 2502.

Figure 25F:
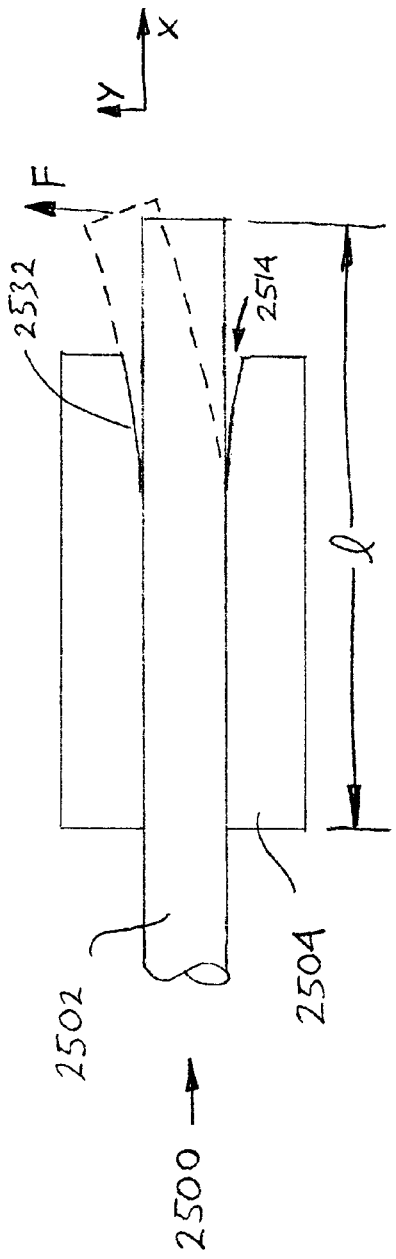
FIG. 25F is a side sectional view schematically showing a portion of the bone implant of FIG. 25A.
Figure 25G:
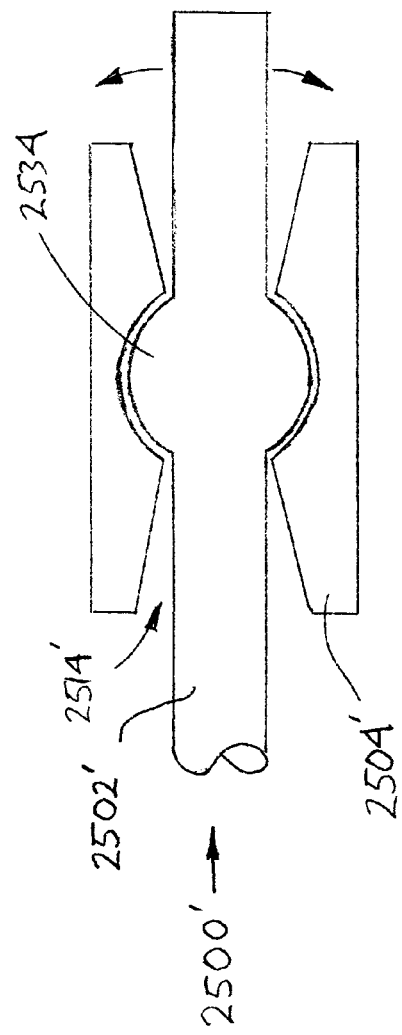
FIG. 25G is a side sectional view schematically showing a variation of a portion of the bone implant of FIG. 25A.

Referring to FIGS. 25F and 25G, central lumen 2514 of body portion 2504 and/or shank portion 2502 may be configured to reduce stress concentrations on shank portion 2502 to help ensure it does not fail in use after it has been implanted. In some prior art implants, repetitive heavy load cycles on the proximal end of shank portion 2502 from a spinal rod connected to the head portion can cause the shank portion to break apart. A typical point of failure is where the shank portion 2502 exits the proximal end of the body portion 2504. According to aspects of the present disclosure, stress concentrations may be reduced in this area to permit greater load cycling without implant failure.

In some embodiments, as shown in FIG. 25F, the proximal end of central lumen 2514 of body portion 2504 may be provided with a curved contour 2532 as shown to more evenly distribute forces between shank portion 2502 and body portion 2504, thereby reducing stress concentrations. In FIG. 25F, the proximal end of shank portion 2502 is depicted in an unloaded state with solid lines and in a deflected state with dashed lines. The degree of deflection is exaggerated in FIG. 25F for ease of understanding. Curved contour 2532 may be provided on just one side of central lumen 2514 in the direction of maximum force, on opposite sides of central lumen 2514, or around the entire circumference of central lumen 2514. In some embodiments, curved contour 2532 may mirror the natural bending profile of shank portion 2502. In particular, the contour may be defined by the following beam deflection formulas:

$$y = (F \cdot x^2)/(6 \cdot E \cdot I) \, (x - 3 \cdot 1)$$

$$I = (D^4 - d^4)\pi/64$$

where
x=distance in horizontal direction in FIG. 25F
y=distance in vertical direction in FIG. 25F
F=force applied to proximal end of shank portion 2502

E=modulus of elasticity of shank portion 2502

I=moment of inertia of shank portion 2502 l=length between where shank portion 2502 is fully supported and the point of force application D=outside diameter of shank portion 2502 d=inside diameter of shank portion 2502

In some embodiments, as shown in FIG. 25G, shank portion 2502' may be provided with a spherical portion 2534 and body portion 2504' may be provided with a mating spherical socket. Body portion 2504' may also be provided with a central lumen 2514' that tapers outwardly towards both its proximal and distal ends, as shown. With this arrangement, shank portion 2502' may pivot within body portion 2504' when a force is applied to its proximal end. The tapered portions may be provided on just one side of central lumen 2514' in the direction of maximum force, on opposite sides of central lumen 2514', or around the entire circumference of central lumen 2514'. When shank portion 2502' reaches the end of its pivoting travel, it is supported by a large surface area of body portion 2504' at both the proximal and distal ends, and may also be supported at spherical portion 2534. These large areas of support greatly reduce the stress concentrations found in prior art implants, and allow the implant to withstand greater forces and/or a larger number of loading cycles without failure. In the embodiments of FIGS. 25F and 25G, the outer surface of shank portion 2502/2502' and/or the inner surface of body portion 2504/2504' may be highly polished to further reduce stress concentrations. In some embodiments the surfaces may have a roughness Ra of between 0.01 and 0.04 microns.

Implant 2500/2500' may be installed in bone, such as across a bone joint or fracture, in a manner similar to that previously described relative to FIGS. 2A-2F and FIG. 24 (i.e. in an S2AI trajectory). In particular, the bone may be prepared by inserting a guide pin into bone segments, spinning a cannulated drill over the guide pin to drill a pilot hole in the bone, and tapping a cannulated broach over the guide pin to create a bore shaped to receive body portion 2504. In some embodiments, any or all of these steps may be omitted. Shank portion 2502 may then be threaded into the pilot hole using a tool attached to the proximal end of shank portion 2502, as previously described. Body portion 2504 may then be tapped into the bone over the proximal end of shank portion 2502. As body portion 2504 engages the splines 2516 located on the proximal end of shank portion 2502, a small rotational adjustment (no more than 15 degrees, for example), may be needed to rotationally align body portion 2504 with the shaped bore. This adjustment may be made manually, or in some circumstances may occur automatically as the tapered and rounded leading edges 2520 of body portion 2504 engage the shaped bore opening in the bone and automatically rotate the implant as needed while body portion 2504 is being tapped into place. Once body portion 2504 is in place, head portion 2506 may be snapped into place on the proximal end of shank portion 2502. Head portion 2506 may include proximally extending tabs as previously described that may be snapped off at this time. When other portions of a spinal construct (not shown) are also in place, a rod may be placed into channels 2528 and secured in place with a nut, as previously described.

In embodiments having a separate head portion that is assembled to a shank portion during implantation as described above, a variety of different head portions can be provided in a kit without having to provide the entire implant for each head type. For example, head portions can be provided that couple to a 5.0, 5.5, 6.0, or 6.35 mm diameter rod. Shank portions and body portions may also be provided in various lengths, widths and or shapes. With this modular approach, a specific head type may be assembled to a specific shank portion and body portion to create a greater number of combinations without having to stock a separate implant for each combination.

In some embodiments, shank portion 2502 can be installed in the bone, and then a broach can be inserted over the proximal end of installed shank portion 2502 to create a shaped bore. After the broach is removed, body portion 2504 may then be installed over shank portion 2502. In some embodiments, the body portion may include an integrated broach such that the body portion can be installed without first preparing a shaped bore in the bone. In some embodiments, body portion 2504 can be installed in the bone first, and then shank portion 2502 can be installed into the bone through body portion 2504, with or without head portion 2506 attached to shank portion 2502 as it is being installed.

According to aspects of the present disclosure, the arrangement of the current embodiment allows for one portion of an implant to be screwed into place, another portion to be tapped into place, and the two portions locked together to take advantage of the anti-rotational aspects of the tapped in portion. In embodiments without splines or other locking features, the various portions can be implanted separately as previously described, or the assembled implant can be installed as a single unit with the body portion rotating in a shaped bore in the bone as the shank portion is screwed into place. In other embodiments having releasable locking features (not shown), the assembled implant can be installed as a single unit with the locking feature released, allowing the shank portion to rotate relative to the body portion. After the implant is installed, the locking feature can be engaged to prevent rotation.

FIGS. 26A-26E show another exemplary embodiment of a bone implant having a tulip or coupling device provided at its proximal end. Implant 2600 includes a shank portion 2602, a body portion 2604 and a head portion 2606. Shank portion 2602 and body portion 2604 may be separate components as with previously described implant 2500, or they may be integrally formed as a single component. In this embodiment, the distal end of shank portion 2602 includes bristles 2608 for securing the shank portion 2602 into a bone segment. Bristles 2608 may be angled proximally and may be flexible, thereby providing little resistance when being introduced distally into a bore within a bone, but locking against the bone and preventing proximal withdrawal from the bone. In some embodiments, bristles 2608 are arranged at a 45 degree angle relative to the longitudinal axis of the implant 2600. Bristles 2608 may be integrally formed with shank portion 2602, such as with an additive manufacturing process. Alternatively, bristles 2608 may be separate elements of the same or different material from shank portion 2602 and inserted into holes formed in shank portion 2602. In some embodiments, head portion 2606 serves to contact the outer surface of the bone to prevent implant 2600 from migrating further into the bone. In other embodiments (not shown), another element that is larger in size than the implant bore in the bone may be located on or adjacent to the proximal end of body portion 2604 to prevent implant 2600 from migrating further into the bone while allowing head portion 2606 to maintain a full range of motion relative to shank portion 2602. In other embodiments (not shown), bristles 2608 may be replaced with or augmented by rigid barbed elements. Further details relating to the fabrication and use of bristles and barbs with orthopedic implants may be found in U.S. Pat. No. 5,716,358 to Ochoa et al.

The proximal end of body portion 2604 may be provided with a flat surface (not shown) to allow shank portion 2602 and body portion 2604 to be tapped into place together into the bone segment(s). Alternatively, internal threads (not shown) may be provided to allow a slap-hammer or other insertion instrument to be temporarily attached to the proximal end of body portion 2604 to aid in inserting implant 2600. A central lumen 2612 may be provided along the longitudinal axis of shank portion 2602 and body portion 2604 to allow them to be placed over a guidewire or guide pin when being implanted.

In this embodiment, body portion 2604 has a triangular cross-section to prevent it from rotating relative to surrounding bone. When body portion 2604 is placed across a joint or fracture between two bone segments as previously described, body portion 2604 inhibits the two bone segments from rotating relative to one another. In other embodiments (not shown), the body portion may have a square, rectangular, oval or other cross-sectional shape with at least one rectilinear face and/or at least one apex to similarly prevent rotation.

Body portion 2604 may be provided with fenestrations 2618 to allow for bony on-growth, in-growth and through-growth. In this exemplary embodiment, a repeating pattern of alternating triangularly shaped fenestrations may be provided on each face of body portion 2604. Each of the fenestrations 2618 opens into a central lumen of body portion 2604. In some embodiments, body portion 2604 is fabricated using an additive manufacturing process such as 3D printing. Further information on designing and manufacturing fenestrated implants is provided in the applicant's U.S. Pat. No. 9,662,157, filed Sep. 18, 2015, and titled "Matrix Implant." The distal end of body portion 2604 may also be provided with tapered leading edges 2620 as shown to facilitate inserting body portion 2604 into one or more bone segments. Trailing edges 2622 having a lesser degree of taper may be provided on the proximal end of body portion 2604 as shown to facilitate removal of body portion 2604 from the bone, if desired. Having less taper on trailing edges 2622 permits better engagement between the proximal end and surrounding cortical bone surfaces.

Figure 26A:
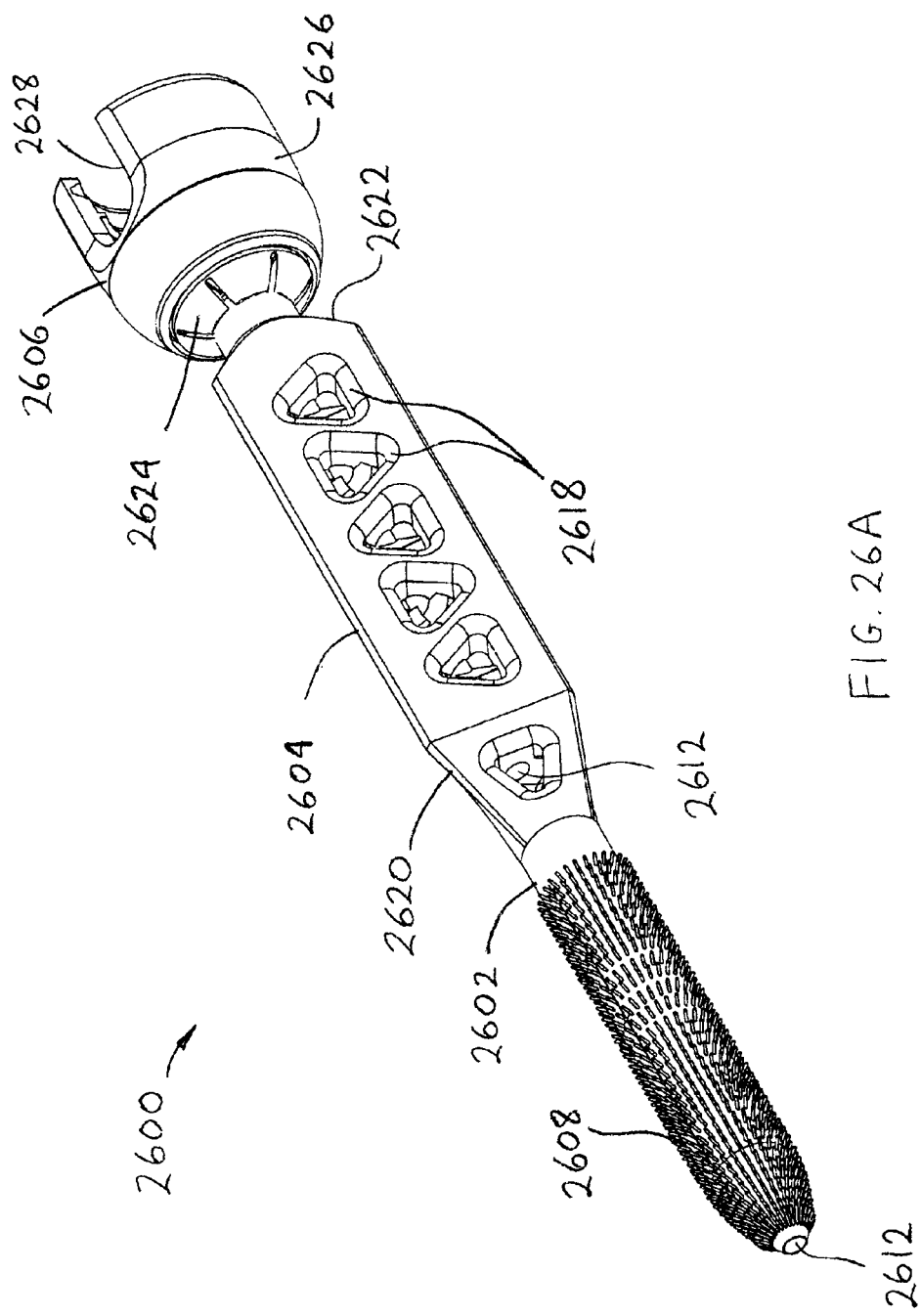
FIG. 26A is a perspective view showing an exemplary embodiment of a bone implant having a tulip or coupling device provided at its proximal end.
Figure 26B:
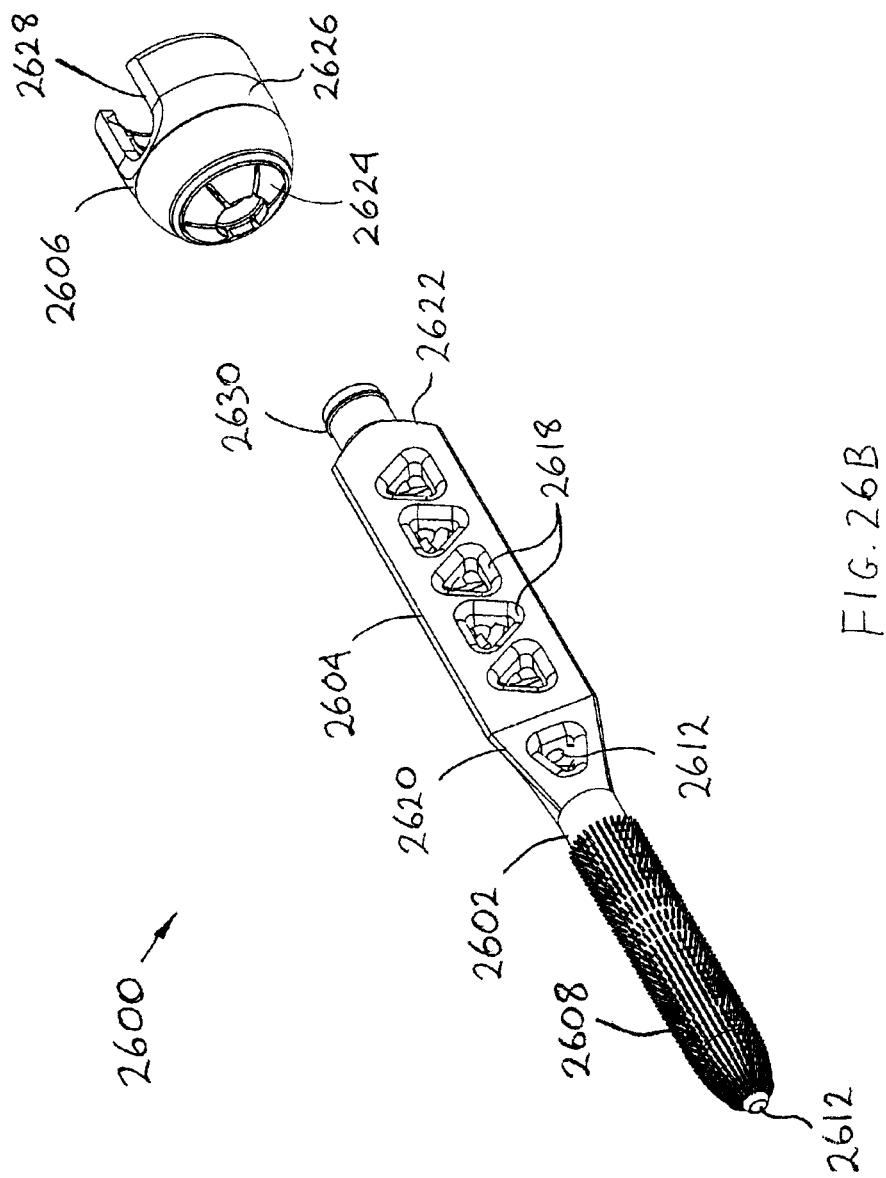
FIG. 26B is an exploded view showing the components of the bone implant of FIG. 26A.
Figure 26C:
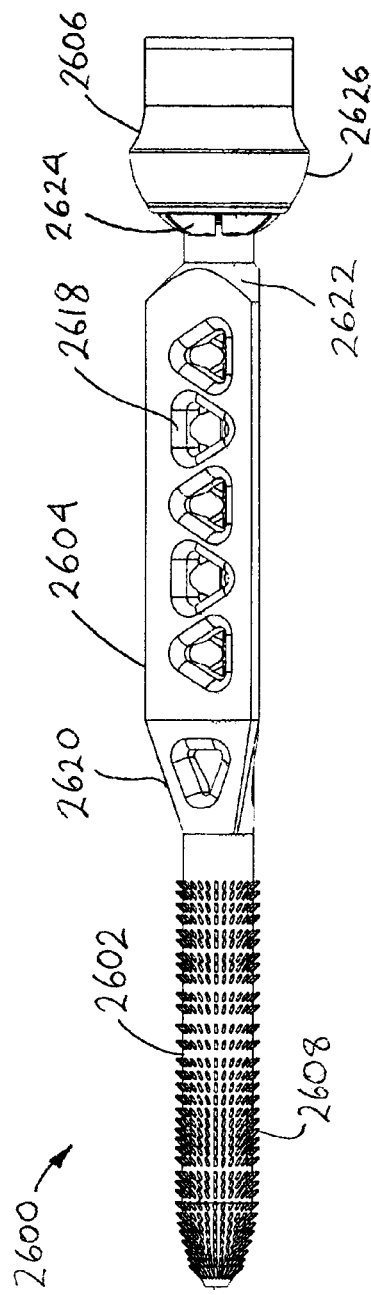
FIG. 26C is a side view showing the bone implant of FIG. 26A.
Figure 26D:
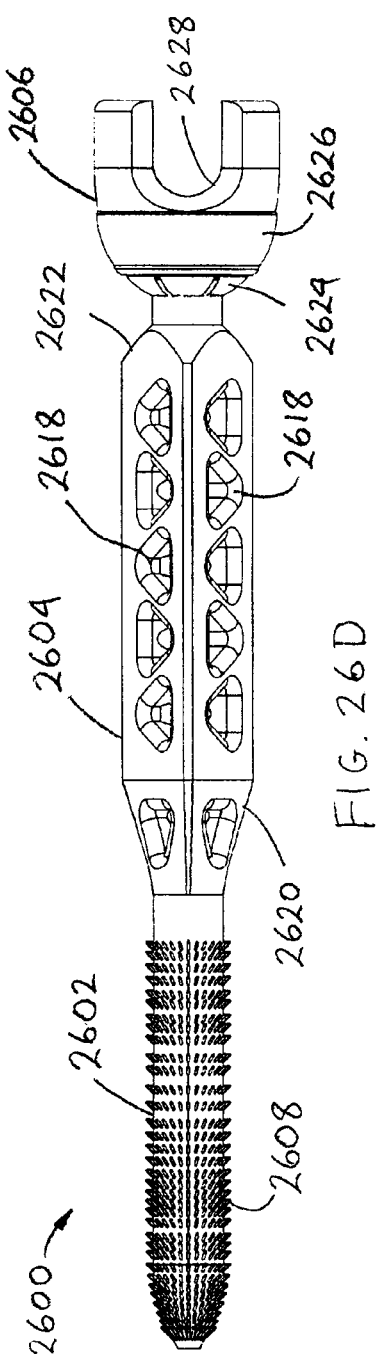
FIG. 26D is a top plan view showing the bone implant of FIG. 26A.
Figure 26E:
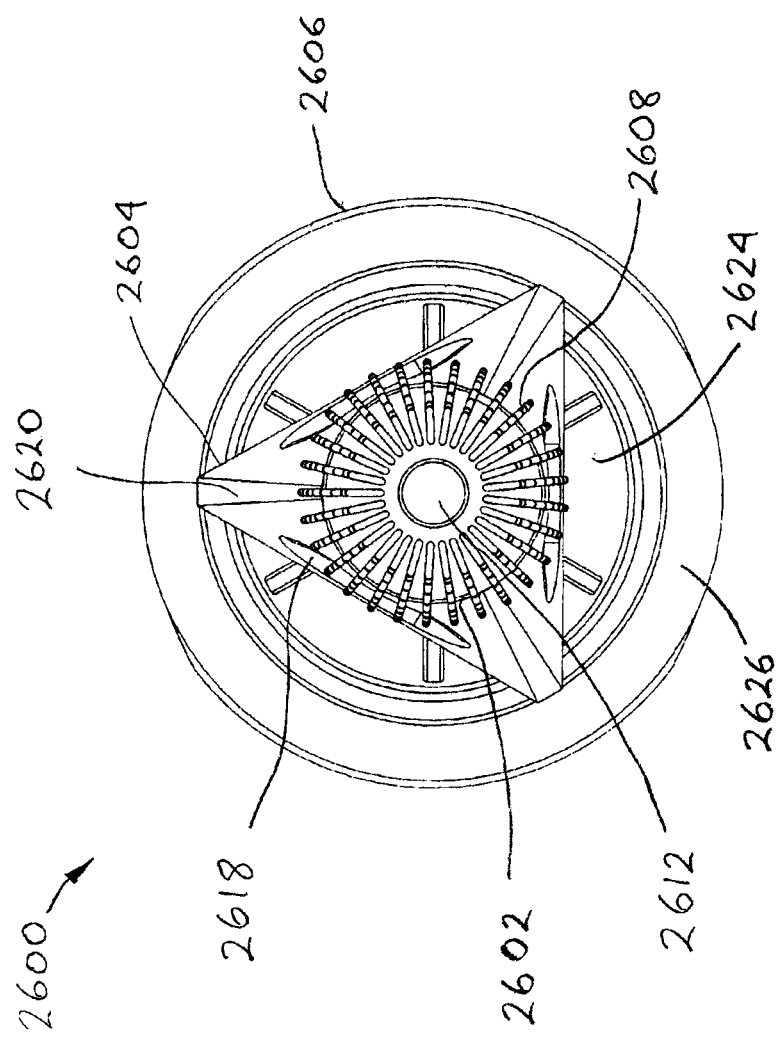
FIG. 26E is a distal end view showing the bone implant of FIG. 26A.

Head portion 2606 may be provided with a coupler 2624 and a main body 2626 as shown in FIGS. 26A-26E, and a nut (not shown). The nut has external threads that mate with internal threads located in the proximal recess of main body 2626 to tighten a spinal rod (not shown) against the bottom of channels 2628 in main body 2626. As shown in FIG. 26B, the proximal end of body portion 2604 may be provided with a circumferential rib or barb 2630 for securing head portion 2606 to body portion 2604 in a snap-fit manner. In some embodiments, main body 2626 is configured to pivot in a poly-axial or spherical manner relative to coupler 2624 and shank portion 2602. In some embodiments, main body 2626 is configured to spin about its main axis relative to coupler 2624 and shank portion 2602. In some embodiments, main body 2626 is configured to immovable relative to coupler 2624 and/or body portion 2604.

Implant 2600 may be installed in bone, such as across a bone joint or fracture, in a manner similar to that previously described relative to FIGS. 2A-2F. In particular, the bone may be prepared by inserting a guide pin into bone segments, spinning a cannulated drill bit over the guide pin to drill a pilot hole in the bone, and tapping a cannulated broach over the guide pin to create a bore shaped to receive body portion 2604. In some embodiments, any or all of these steps may be omitted. Shank portion 2602 and body portion 2604 may then be tapped into the pilot hole and shaped bore, with or without a tool attached to the proximal end of body portion 2604, as previously described. Once shank portion 2602 and body portion 2604 are in place, head portion 2606 may be snapped into place on the proximal end of body portion 2604. In some implementations, shank portion 2602 and body portion 2604 may be tapped into place with head portion 2606 already installed on the proximal end of body portion 2604. Head portion 2606 may include proximally extending tabs as previously described that may be snapped off at this time. When other portions of a spinal construct (not shown) are also in place, a rod may be placed into channels 2628 and secured in place with a nut, as previously described.

Figure 27A:
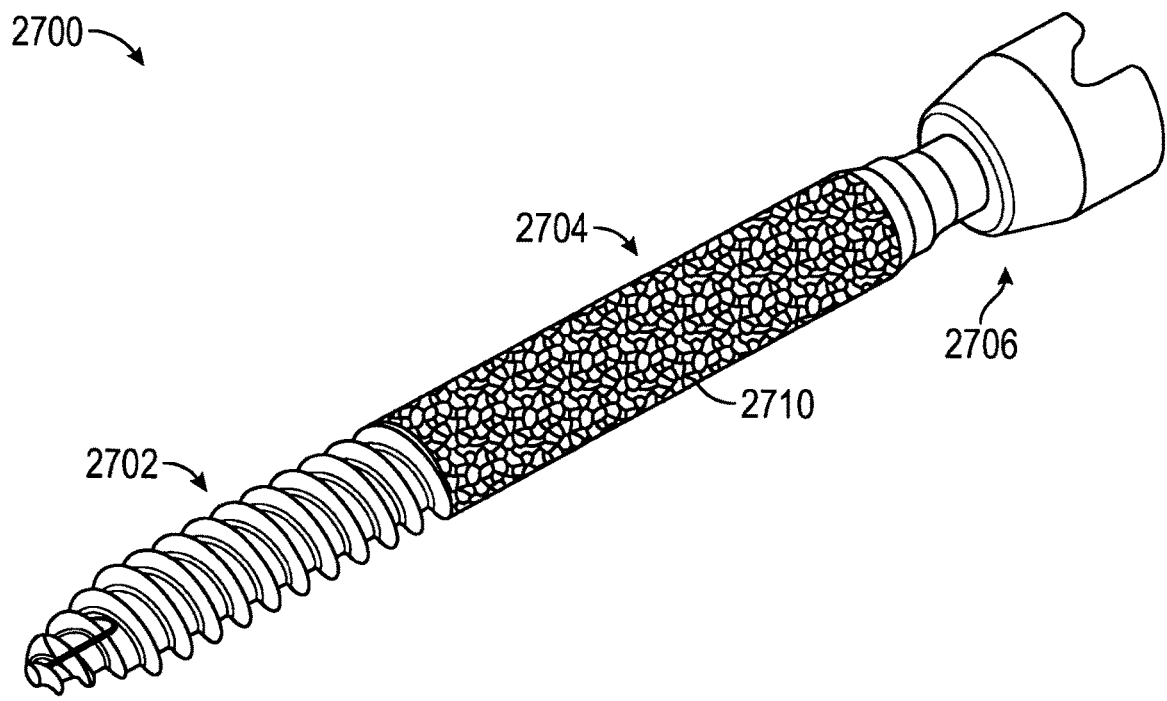
FIG. 27A is a perspective view showing an exemplary embodiment of a bone implant having a tulip or coupling device provided at its proximal end.
Figure 27B:
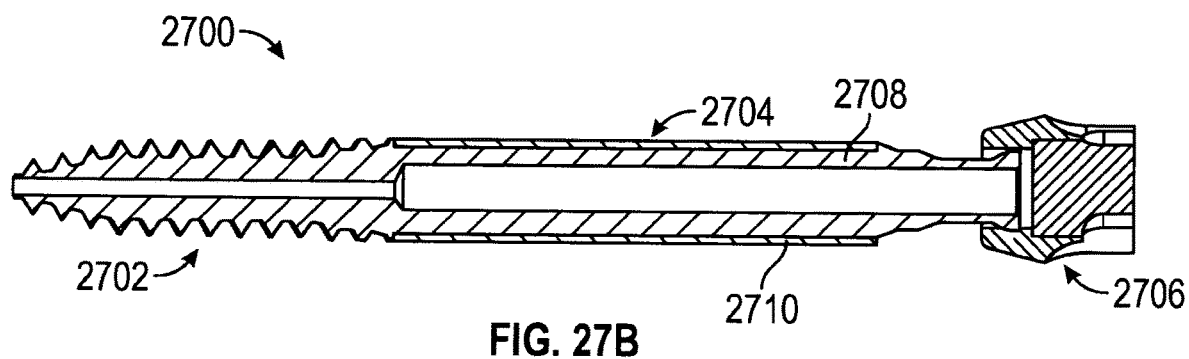
FIG. 27B is a side sectional view showing the bone implant of FIG. 27A.

FIGS. 27A and 27B show another exemplary embodiment of a bone implant having a tulip or coupling device provided at its proximal end. Implant 2700 is a form of sacral alar iliac (SAI) screw and includes a threaded shank portion 2702, a body portion 2704 and a head portion 2706. Threaded shank portion 2702 and head portion 2706 of implant 2700 are similar to those of implant 2500 previously described in reference to FIGS. 25A-25G.

Body portion 2704 includes a porous exterior surface that is configured to reside across a bone joint and/or a proximal bone segment when implanted. In this embodiment, body portion 2704 includes a radially inward portion 2708 that is solid and a radially outward portion 2710 that is a porous bony in-growth region, as shown in FIG. 27B. Radially outward portion 2710 may be formed from a porous plasma spray coating with an irregular surface, which supports stable bone fixation/fusion. This implant structure and the surgical approaches disclosed herein make possible the placement of larger fusion surface areas designed to maximize post-surgical weight bearing capacity and provide a biomechanically rigorous implant designed specifically to stabilize the heavily loaded SI-Joint. In other embodiments, the entire shank portion and body portions can be porous.

Implant 2700 can be made of a variety of materials. For example, the implant can be made of a metal or metal alloy, such as titanium or steel, or a nonmetallic material such as ceramic or polymer. In some embodiments, the implant material can have a certain lattice microstructure formed from microparticles. For example, the lattice microstructure can result in a rough or smooth surface texture, depending on the surface finishing techniques used, such as polishing or application of a metal plasma spray. A 3-D printing process may be used to fabricate some or all of implant 2700, which allows the porosity of the implant or printed portions to be controlled. For example, the implant can have a volume porosity between about 30 and 70 percent, with an average pore size between 100 and 1000 microns. The pores can be largely interconnected, largely unconnected, or a mix of interconnected and unconnected pores. In some embodiments, the pores can be located throughout the material of the implant, including the inner and outer implant surfaces. For example, the fusion of the microparticles that form the implant can result in a porous, semi-porous, or nonporous structure, depending on the degree of fusion between the microparticles. In other embodiments, the pores can be located in a porous coating that can be applied onto the implant. For example, a porous coating can be applied using a titanium plasma spray process, or another metal plasma spray process. The coating can be applied to the outer surfaces of the implant, the interior surfaces of the implant, or both the outer and interior surfaces of the implant. For example, the coating could be preferentially applied to the outer surface of a matrixed implant to provide bony ingrowth and on-growth, and not applied to the inner portion of the implant to maximize bony through-growth within the implant. Also, the coating can be applied preferentially from proximal to distal, or vice versa. The thickness of a porous coating can be between about 500 and 1,500 microns. In addition or alternatively to the porous metal coating, a hydroxyapatite coating can also be applied to the implant. In some embodiments, the porosity can be varied along the length of the implant. In some embodiments, the thickness of the coating can be varied along the length of the implant. In some embodiments, the thickness of the coating applied to the outer surface can be different than the thickness of the inner coating. For example, the outer coating may be greater than the inner coating in some embodiments. In other embodiments, the thickness of the inner and outer coatings can be the same.

Figure 28A:
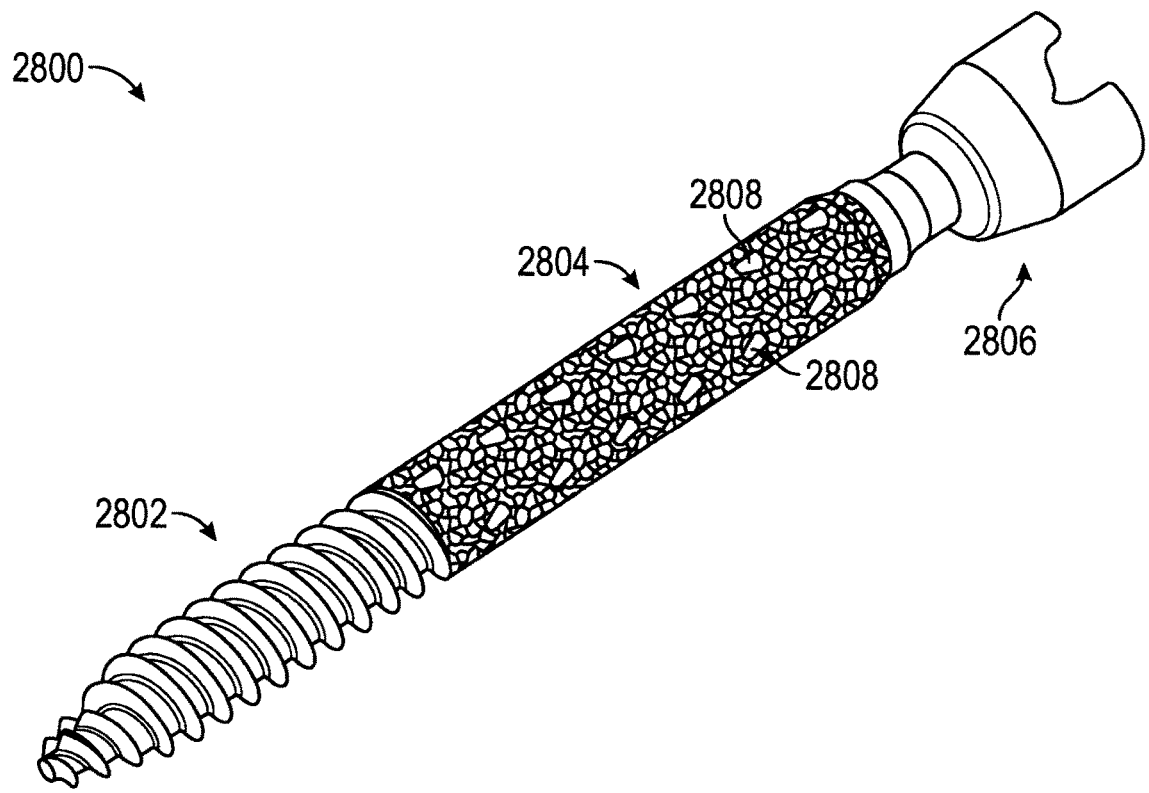
FIG. 28A is a perspective view showing an exemplary embodiment of a bone implant having a tulip or coupling device provided at its proximal end.
Figure 28B:
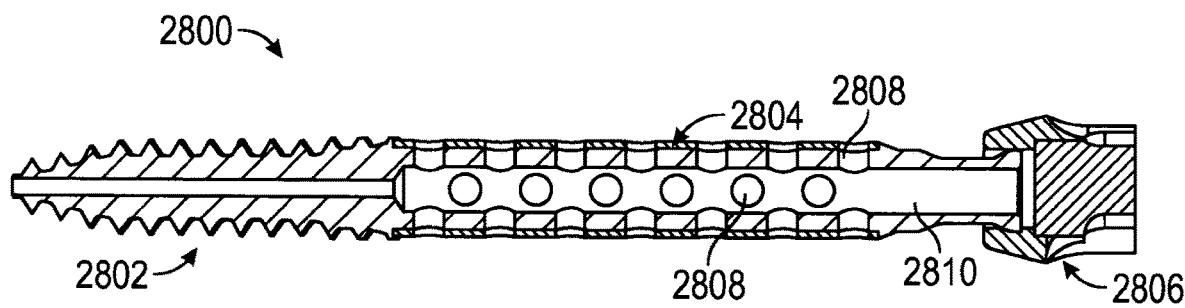
FIG. 28B is a side sectional view showing the bone implant of FIG. 28A.

FIGS. 28A and 28B show another exemplary embodiment of a bone implant having a tulip or coupling device provided at its proximal end. Implant 2800 is a form of sacral alar iliac (SAI) screw and includes a threaded shank portion 2802, a body portion 2804 and a head portion 2806. Threaded shank portion 2802 and head portion 2806 of implant 2800 are similar to those of implant 2500 previously described in reference to FIGS. 25A-25G.

Body portion 2804 includes a porous exterior surface that is configured to reside across a bone joint and/or a proximal bone segment when implanted, and may be similar to body portion 2704 previously described in reference to FIGS. 27A and 27B. In this embodiment, body portion 2804 includes fenestrations 2808 that communicate between the exterior surface and a central lumen 2810. Fenestrations 2808 may be circular in shape as shown, or may be formed in other shapes. Fenestrations 2808 may be configured to promote bony on-growth, ingrowth and/or through-growth for faster implant and/or bone joint fusion.

Figure 29A:
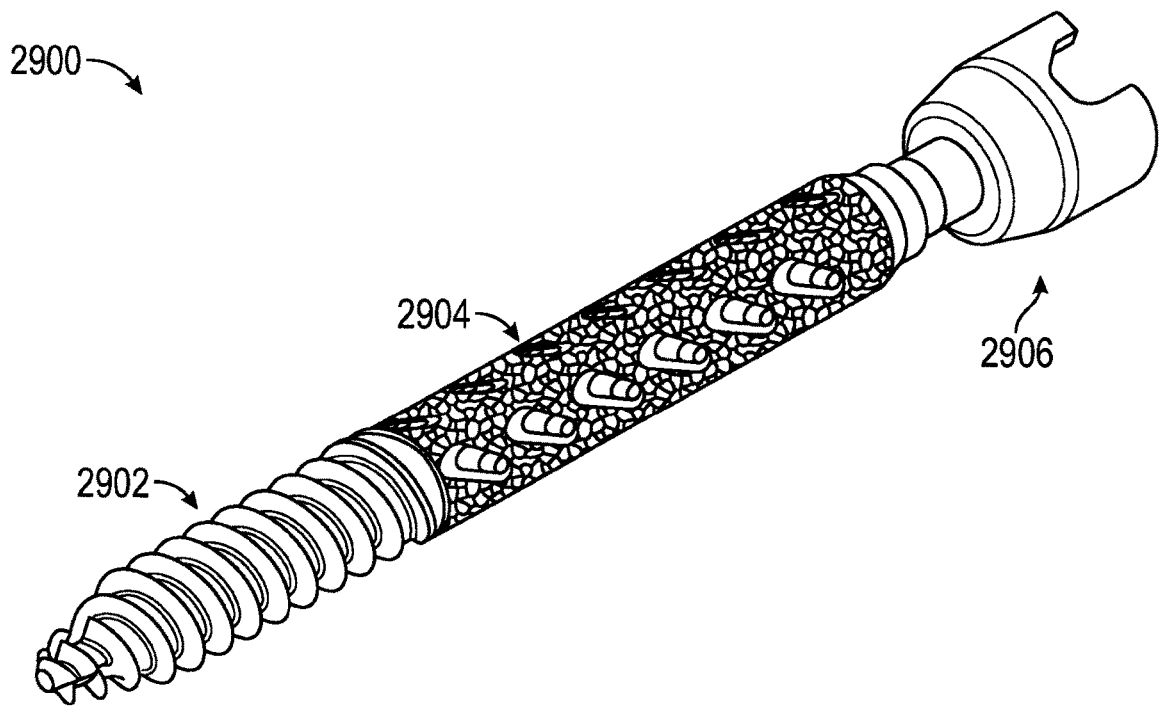
FIG. 29A is a perspective view showing an exemplary embodiment of a bone implant having a tulip or coupling device provided at its proximal end.
Figure 29B:
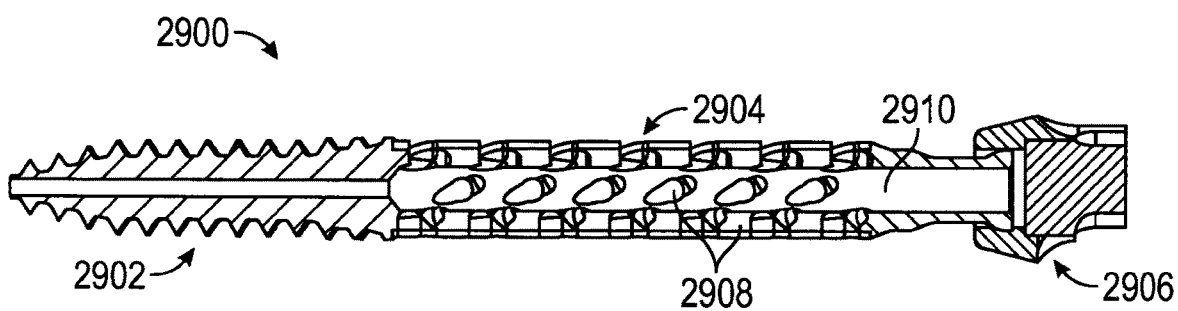
FIG. 29B is a side sectional view showing the bone implant of FIG. 29A.

FIGS. 29A and 29B show another exemplary embodiment of a bone implant having a tulip or coupling device provided at its proximal end. Implant 2900 is a form of sacral alar iliac (SAI) screw and includes a threaded shank portion 2902, a body portion 2904 and a head portion 2906. Threaded shank portion 2902 and head portion 2906 of implant 2900 are similar to those of implant 2500 previously described in reference to FIGS. 25A-25G.

Body portion 2904 includes a porous exterior surface that is configured to reside across a bone joint and/or a proximal bone segment when implanted, and may be similar to body portion 2704 previously described in reference to FIGS. 27A and 27B. In this embodiment, body portion 2904 includes fenestrations 2908 that communicate between the exterior surface and a central lumen 2910. Fenestrations 2908 may be oblong and set at an angle, as shown. In this exemplary embodiment, fenestrations 2908 are all aligned in the same direction as the threads located on the shank portion 2902, but form a more acute angle with the longitudinal axis of implant 2900. Additionally, fenestrations 2908 may be provided with sharp cutting edges, such as along their proximal and/or trailing edges. These cutting edges can scrape bone material from the surrounding bone as implant 2900 is being screwed into place and channel the bone material towards central lumen 2910 to create a self-grafting SAI screw. This bone material may then promote faster bone growth in and/or around implant 2900. Fenestrations 2908 themselves may also promote bony on-growth, ingrowth and/or through-growth for faster implant and/or bone joint fusion.

Figure 30A:
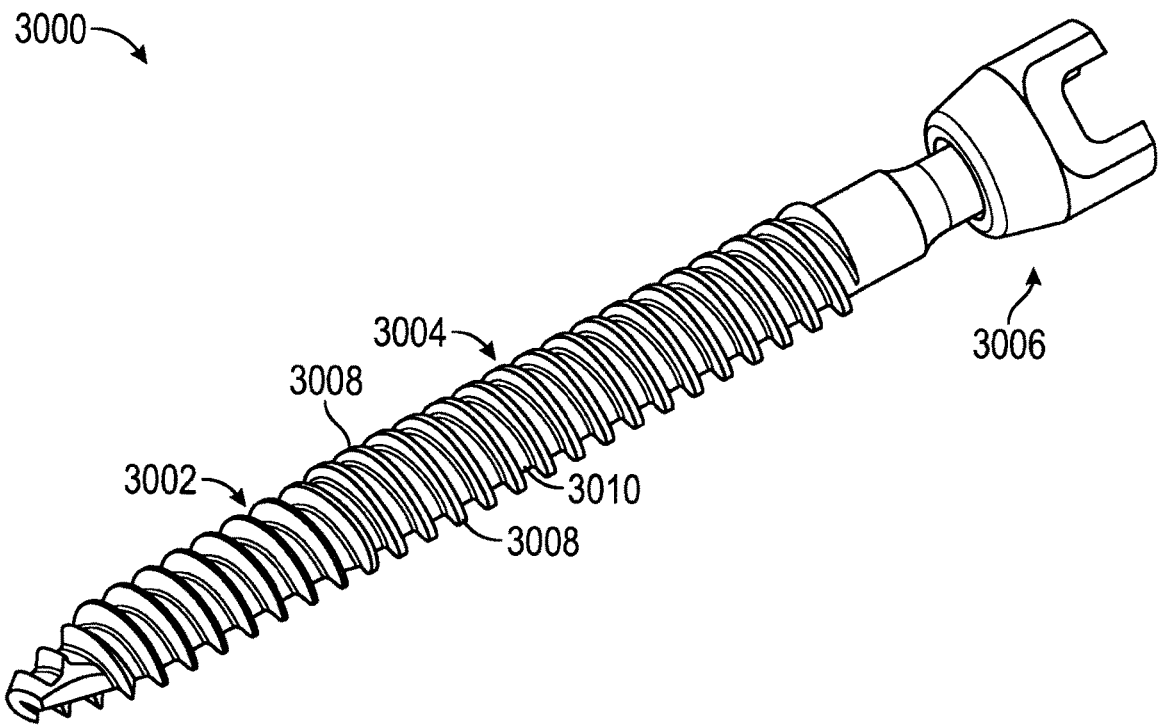
FIG. 30A is a perspective view showing an exemplary embodiment of a bone implant having a tulip or coupling device provided at its proximal end.
Figure 30B:
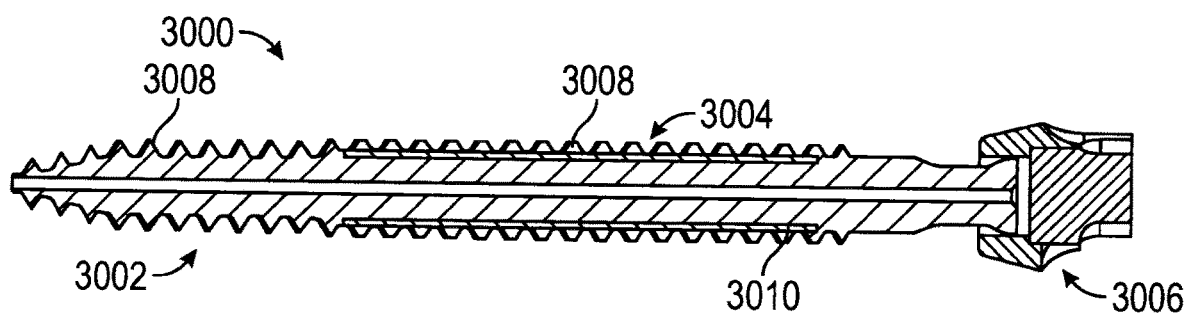
FIG. 30B is a side sectional view showing the bone implant of FIG. 30A.

FIGS. 30A and 30B show another exemplary embodiment of a bone implant having a tulip or coupling device provided at its proximal end. Implant 3000 is a form of sacral alar iliac (SAI) screw and includes a threaded shank portion 3002, a body portion 3004 and a head portion 3006. Threaded shank portion 3002 and head portion 3006 of implant 3000 are similar to those of implant 2500 previously described in reference to FIGS. 25A-25G.

Body portion 3004 includes a porous exterior surface that is configured to reside across a bone joint and/or a proximal bone segment when implanted, and may be similar to body portion 2704 previously described in reference to FIGS. 27A and 27B. In this embodiment, a single set of threads 3008 extends continuously across shank portion 3002 and body portion 3004. On the body portion 3004, the minor diameter or roots of threads 3008 may be filled with or formed by a porous material 3010. The major diameter or crests of threads 3008 may be formed on top of a sleeve of porous material 3010, as shown in FIG. 30B. Alternatively, the major diameter or crests of threads 3008 may be formed integrally with the minor diameter or roots, and the porous material 3010 can simply reside within the roots (not shown.) Porous material 3010 may then promote on-growth to body portion 3004 and in-growth to threads 3008.

Figure 31:
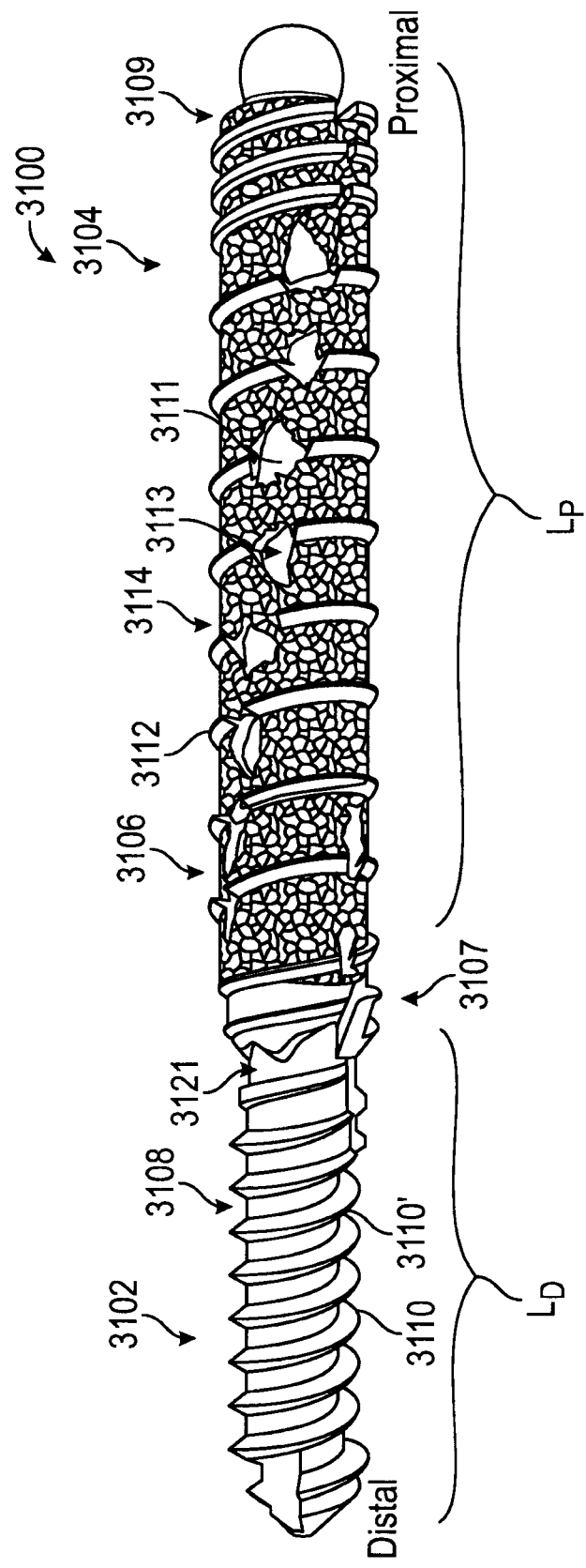
FIG. 31 is an example of a composite implant.

FIG. 31 illustrates another exemplary implant for use in at least one of fusing or stabilizing bony tissue, sized and configured such that when the elongate body is implanted via a posterior sacral alar-iliac ("SAI") trajectory (e.g. S2AI) with a bony entry point between a S1 and a S2 foramen, a distal region of the elongate body extends distal to a sacroiliac ("SI") joint and within the outer surfaces of an ilium, and a proximal region of the elongate body is disposed across the SI joint. The implant includes a distal anchoring region having one or more distal surface features adapted to anchor the distal anchoring region relative to iliac bone. The implant also includes a proximal region disposed proximal to the distal region, the proximal region having one or more proximal surface features adapted that facilitate at least one of bony on-growth, in-growth, or through-growth. The implant in FIG. 31 is an example of a composite implant, or an implant that is comprised of two or more components.

The embodiment in FIG. 31 is similar to some regards to the embodiments in FIGS. 25A-30B herein. Any suitable feature described with respect to the embodiments in FIGS. 25A-30B can be included in the embodiments that follow, and visa-versa, unless indicated to the contrary. Implant 3100 includes distal region 3102 configured for anchoring into bone, such as relatively denser cortical bone, and proximal region 3104, which is adapted to facilitate at least one of bony on-growth, in-growth, or through-growth. Distal region 3102 includes at least one thread 3110, and proximal region 3104 includes at least one thread 3112.

As in the embodiments above, proximal region 3104 is adapted to facilitate at least one of bony on-growth, in-growth, or through-growth. In this example, the adaption includes a porous surface 3114, which is formed in between one or more threads. The thread 3112 in the central region of the proximal region is discontinuous, but has an overall helical configuration. The proximal region 3104 includes a plurality of fenestrations 3113 (which are larger than the pores 3114), a subset of which together are disposed in at least a partial helical configuration, as shown in the figure. In this embodiment multiple subsets of the plurality of fenestrations 3113 are each disposed in a partial helical configuration. At least some of the fenestrations are disposed at the location of the thread discontinuities, as shown in the figure.

Implant 3100 includes inner elongate body 3108 and outer elongate body 3106. Inner and outer elongate bodies are adapted to stably interface with one another to resist relative motion in at least one direction. Inner elongate body 3108 includes the thread 3110 on the distal region 3102 of the implant. Outer elongate body 3106 includes the thread 3112 on the proximal region 3104 of the implant. Inner elongate body 3108 has a proximal region 3111 that is non-threaded, which optionally may include a thread that interfaces with an optional internal thread on outer body 3106. Outer body includes a distal region 3107 that includes a dual-lead thread, a central region with a single lead thread, and a proximal dual-thread region 3109. One of the threads from distal region 3107 does not continue into the central region with the single thread. Outer body 3106 also includes relatively large fenestrations 3113, as well as relatively smaller pores 3114 that are in between the threads. Outer elongate body 3106 has a larger outer diameter than inner elongate member 3108. Outer elongate body 3106 can have an inner diameter radially spaced from the outer diameter of the inner elongate body 3108, thereby creating a volume of space radially between the inner and outer elongate bodies 3106 and 3108.

In this exemplary embodiment the inner and outer bodies each have one or more features that allow them to be engaged such that relative movement between the two is resisted in at least one direction, optionally resisting rotation. Outer body 3106 includes one or more surface feature 3121 disposed at a distal end region of the outer body 3106 sized and configured to interface with a protruding feature (optionally linear) on inner elongate body 3108, the interface of which prevents rotation between the outer and inner elongate bodies. In this embodiment rotation is prevented at the distal end of the outer elongate body due to the interfacing features. A wide variety of features can be incorporated onto the inner and outer elongate bodies to provide this functionality, such as that shown and described with reference to FIG. 25B herein.

When implants herein are implanted in a SAI trajectory (e.g. S2AI) for positioning across an SI joint (details of which are described elsewhere herein), a portion of the implant that has one or more surface features specifically adapted to facilitate at least one of bony on-growth, in-growth, or through-growth should be positioned at the location of the SI joint. FIGS. 32A and 32B illustrate imaging showing an SAI trajectory for implanting an SI joint stabilization implant across a SI joint, with the arrow indicating the trajectory. "Joint length" is a distance from the entry point in the sacrum to the subject's SI joint. "Overall length" is a distance from the entry point in the sacrum to the outer boundary of the subject's iliac cortex. Additionally, a distal portion of the implant that will be positioned distal to the SI joint preferably has one or more surface features (e.g., threaded region(s)) that adapt the distal region to effectively anchor in the relatively more dense iliac cortical bone. An important consideration for implantable devices that are implanted across an SI in an SAI trajectory is designing and configuring different regions of the implant based on the tissue that will be adjacent to the region(s) when implanted.

With respect to FIG. 31, for example, implant 3100 includes pores 3114 that span a length so that when implanted in an S2AI trajectory across an SI joint, the pores 3114 will be disposed at the location of the SI joint and will facilitate at least one of bony on-growth, in-growth, or through-growth. It is noted that the pores may also extend into distal region 3102. In this embodiment the single lead thread in the proximal region 3104 allows more space for the pores to be created in the proximal region 3104 of the implant, in this instance in at least some of the regions between the thread(s). Additionally, distal region 3102, which will be implanted distal to the SI joint in the relatively more dense iliac cortical bone, has one or more surfaces features (e.g. thread(s)) that adapt the distal region 3102 to effectively and better anchor into the denser bone. In this example, distal region 3102 includes a dual lead thread (which may be more than dual), causing it to provide better anchoring that the single lead thread in the central region of proximal region 3104. It is noted that the thread in the central region of proximal region 3104 could have a smaller pitch, and still be adapted to facilitate in growth (e.g. with pores). It is thus understood that one or more characteristics (e.g. pitch) of surface features may be the same in both the proximal and distal regions. In this embodiment the pitch is the same, but the distal region has a multiple (dual in this case) lead thread. In the embodiment in FIG. 31, one or more surface features in the proximal and distal regions have different characteristics.

Figure 33B:
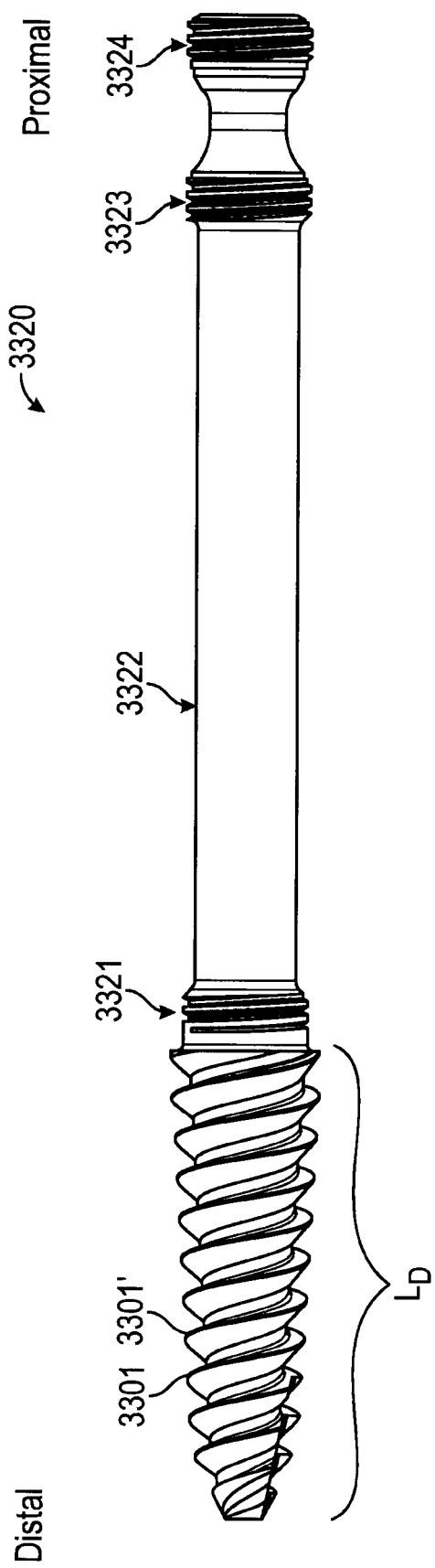
FIG. 33B illustrates an exemplary elongate inner member.
Figure 33C:
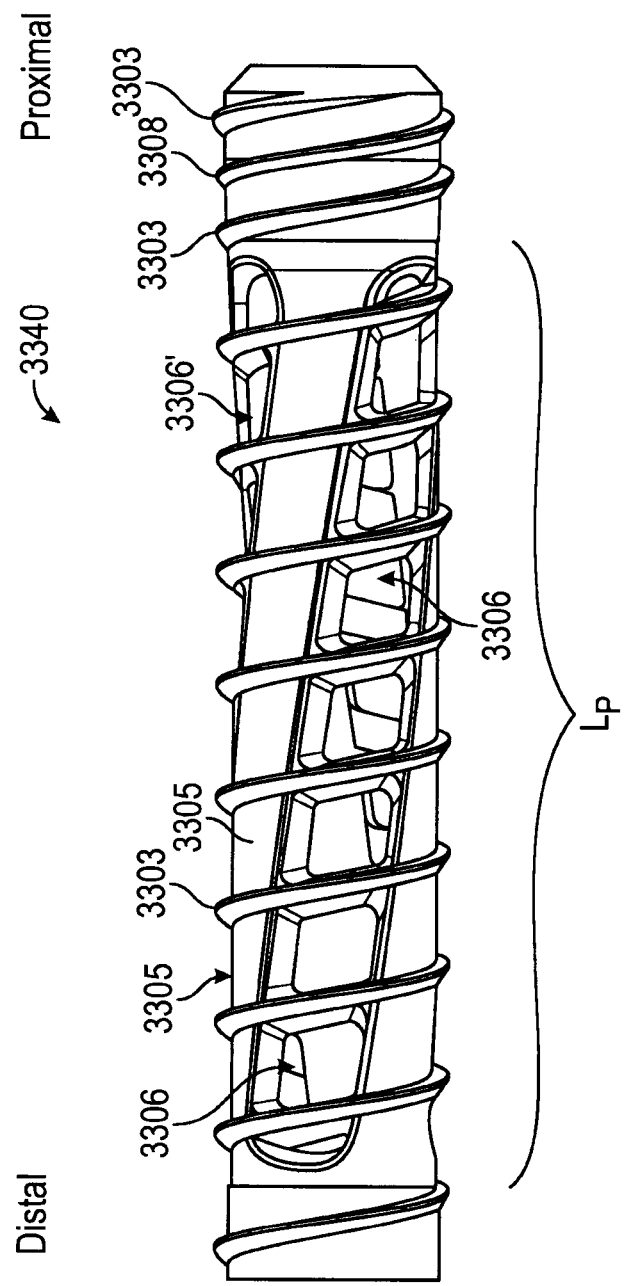
FIG. 33C illustrates an exemplary outer member.

FIGS. 33A-33C illustrate an exemplary embodiment of a composite implant that can be sized and configured for implantation across an SI joint via a SAI trajectory (e.g. S2AI). While implant 3300 is described as being a composite implant composed of a plurality of pieces that are assembled prior to implantation (in this embodiment, two parts), implant 3300 can be modified to be a single, integral unit, that is manufactured from a single component. Implant 3300 includes ingrowth region 3304, which is similar to other implant "proximal regions" herein. Implant 3300 also includes anchoring region 3302, which is similar to other "distal regions" herein. Implant 3300 is similar to implant 3100 in FIG. 31. Any description of implant 3100 may be incorporated into implant 3300, and visa-versa, unless indicated herein to the contrary. Distal anchoring region 3302 includes double lead threads 3301 and 3301', and distal region 3302 is tapered in the distal direction. Proximal ingrowth region 3304 includes a plurality of larger fenestration 3306, subsets of which have a partial helical formation, as shown. In this embodiment, thread 3303 is continuous (unlike thread 3112) with fenestrations 3306 being disposed between the thread. Proximal region 3304 also includes pores 3305, also disposed between thread 3303. In variations, thread 3303 could have one or more discontinuities (like thread 3112), but could also have sections that make complete turns (at least 360 degrees) in between discontinuities in the thread.

Implant ingrowth region 3304 includes a plurality of fenestrations 3306 and smaller pores 3305, both of which extend through an outer surface and an inner surface of the proximal region, creating a passageway from an inner implant volume (but not the "innermost" volume in this embodiment) to a location outside the implant. Fenestrations 3306 and pores 3305 help adapt the proximal anchoring region to facilitate in-growth.

In this embodiment, implant 3300 includes inner component 3320 (e.g., a screw or screw-like component) and outer component 3340 (e.g., an outer sleeve), which are adapted to be secured relative to one another prior to the implant being fully implanted (e.g. secured prior to any part of the implant being implanted, or secured at some point during the procedure), and which are not integrally formed from the same component. The inner component is an example of an inner shank, and the outer component is an example of a sleeve. Inner component 3320 and outer component 3340 are shown individually, not secured together, in FIGS. 33B and FIG. 33C, respectively. In this embodiment, when the inner and outer components are secured together, they interface such that relative motion between the two is restricted in at least one direction (e.g. rotational and/or axial). Inner component can have outer component interface 3321 shown in FIG.

33B, which in this embodiment is a threaded region that can mate with an inner thread on outer component 3340, and when interfaced the distal end of the outer component 3340 is secured to the inner component 3320. The proximal end of outer component can also be secured to the inner component, such as with a threaded connection (e.g. that can include proximal threaded region 3323 on the inner component). In this embodiment inner component includes a non-threaded region 3322, which may be a shaft, such as a smooth shaft. The non-threaded region can be the internal surface of an inner volume disposed between the inner component and the outer component. Non-threaded region 3322 can have any number of surface features meant to facilitate ingrowth, such as a roughened or other similar non-smooth surface. In this embodiment, it is the inner component 3320 that includes the distal anchoring region 3302 of implant 3300, which in this embodiment includes the threads 3301 and 3301'.

FIG. 33C illustrates outer component 3340, which in this embodiment is an outer sleeve that is sized and configured to be advanced over the inner component 3320, the both of which are adapted to be secured relative to one another to resist relative motion therebetween in at least one direction. Outer component 3340 has an internal bore extending therethrough, wherein fenestrations 3306 are created through the inner component 3340, creating communication between the internal bore and the outside of the implant. At the proximal end region of the outer component 3340, there is a second thread 3308, creating a dual thread region at the proximal end region. Thread 3303 extends to the end of the thread region, and in this exemplary embodiment has a constant pitch along its length, but in other embodiment the pitch can vary to some extent. While not shown in FIG. 33C, pores 3305 can be in the outer component between the threads, as in the embodiment in FIG. 31. Optional porous regions 3305 are labeled (only two are labeled) but the pores are not shown in FIG. 33 for clarity. A plurality of individual fenestrations 3306 together extend in a partial helical configuration, even though the fenestrations are considered individual fenestrations. In this embodiment there are three regions of fenestrations that each extend in a partial helical configuration, as shown in the figures. The fenestrations 3306 do not extend into the dual-threaded region at the proximal end of the outer component 3340, nor do they extend all the way to the distal end of the outer component. Any number of the fenestrations 3306 can be tapered (larger outer dimension), as shown. The optional fenestrations can facilitate at least one of bony on-growth, in-growth, or through-growth, as can the optional fenestrations.

The plurality of sets of fenestrations 3306 in this embodiment are configured and oriented so that a physician can see passing through the outer component from one side to the other using radiographic imaging to monitor bony ingrowth and fusion over time.

An exemplary advantage of having a composite implant with two (or more) pieces is that a first (e.g. inner shank) component that is more resistant to fatigue can be manufactured using some common techniques, which may include some common screw manufacturing techniques. The first component (e.g. inner component) may be made from a material that is relatively more resistant to fatigue, such as, for example without limitation, titanium or stainless steel. For example, inner component 3320 shown in FIG. 33B may be made from a relatively more fatigue resistant material, such as titanium, which provides strength to the implant 3300. Additionally, distal anchoring region 3302 can be manufactured using, for example, common screw manufacturing techniques. By selecting a material for the inner component that is stronger and imparts strength to the implant, the second component, such as outer component 3340 (e.g., outer sleeve) shown in FIG. 33C, need not be as fatigue resistant. This provides more options for choosing a design and/or material for the second component, which allows for more design options for the second component, and can thus make easier the process of imparting additional functionality to the implant using design features of the second component. For example, outer component 3340 (e.g., a sleeve) may be designed with certain functionality (e.g., porous and/or roughened surfaces) that causes it to be less fatigue resistant, and optionally much less fatigue resistant, than the inner component. The outer component (e.g., 3340) may be made from a wide variety of materials, such as titanium alloy, polymers, or ceramics. In this embodiment, the outer component, which will be referred to as an outer sleeve, provides several features to the implant. By having an axially extending central bore with an inner diameter greater than the outer diameter of the inner component, the implant has an empty volume between the inner and outer component that helps facilitate the ingrowth of tissue therebetween, which helps stabilize the implant after implantation. The volume of space can also be used to deliver one or more agents into the subject after the implant is positioned in the subject. Additionally, the outer sleeve includes aperture and/or fenestration that can also facilitate the ingrowth of tissue into the volume. The outer sleeve also includes one or more threads, which help anchor the implant at the location of the thread(s), which is this embodiment includes the location of the SI joint.

Any of the composite implants in this disclosure may thus benefit from the exemplary advantages of composite implants set forth herein.

As set forth herein, the implants in FIGS. 25-47 may be implanted across an SI joint and can be advanced using a SAI trajectory (e.g. S2AI), such as is generally shown in FIG. 24 herein. As set forth herein, the different regions of the implant can be configured to provide one or more functions, which may depend on the type of tissue that will be adjacent to the particular region during or after implantation. For example, the SAI implants will preferably have a region, such as proximal region 3304 that when implanted and extends across the SI joint, facilitates at least one of bony on-growth, in-growth, or through-growth. As can be seen from FIGS. 32A and 32B, the proximal region should have a length such that when implanted, will extend across the SI joint. In some embodiments the proximal ingrowth region (e.g., region 3304) has a distal end that extends at least as far as 20 mm from the proximal end of the implant. In this context, the proximal end does not necessarily extend all the way to the proximal end of the implant. The proximal region merely has a distal end that is at least 20 mm away the proximal end of the implant. In some embodiments the distal end is from 20 mm-100 mm from the proximal end of the implant, optionally from 30 mm-75 mm, optionally from 30 mm to 60 mm. In this context, "proximal region" generally refers to a region of the implant that has at least one structural difference than a distal anchoring region that is closer to the implant distal end than the proximal growth region. In the exemplary embodiment in FIGS. 33A-33C, one of the structural differences between the proximal region and the distal region is that proximal region has a threaded region with a lower percentage (of its length) of dual-lead or multi-lead threads. Additional differences in this embodiment include fenestrations and pores present in the proximal anchoring region. The exemplary lengths of the proximal growth regions in this embodiment can be incorporated into other SAI implants herein, such as those in FIGS. 25-30. Any of the lengths of the proximal regions ("proximal region" in these contexts may also refer to "proximal growth regions") in this context can also be a length of the shank or shaft region 3322 of the inner component.

Other types of implants that may appear to have similar structure and dimensions many not necessary provide the advantages set forth herein. For example, the relative lengths of different sections of the those other implants, in combination with the overall length of those implants, may not necessary be sized to provide the benefits herein when implanted according to methods set herein. For example, other types of implants may not have a distal anchoring section that is sized (including length) and configured for ilium bone anchoring, and a proximal section that is sized (including length) to be positioned across a SI joint when the distal anchoring region is disposed in the ilium, the proximal region adapted to facilitate tissue growth.

The distal anchoring regions (e.g. region 3302 in FIG. 33A) in this context refers generally to a distal region of the implant that does not extend all the way to the proximal end of the implant, and which has one or more structural differences than a more-proximally disposed region, wherein the distal region has one or more structural features that better adapt the distal region for anchoring to tissue than the more proximally disposed region. For example, the distal region 3302 has a higher percentage of dual-lead or multi-lead threads and can be made of stronger material or as a stronger structure than proximal region 3304, adapting it for better anchoring than a more proximally disposed region. The distal region may or may not extend all the way to the distal end of the implant. In the embodiment in FIGS. 33A-C, for example, the distal region is considered to extend all the way to the distal end of the implant. The distal end of the distal anchoring region extends at least as far distally as 40 mm from the proximal end of the implant. Extending at least this far distally adapts the distal region of the implant to better anchor into more dense cortical iliac bone, which will be adjacent the distal region when the implant is implanted in an SAI trajectory. The distal end of the distal region may be from 40 mm to 120 mm away from the proximal end of the implant, optionally from 40 mm to 100 mm, optionally from 40 mm to 80 mm. The distal end of the implant should not breach through the iliac bone and extend out of the iliac bone.

In some embodiments the length of the distal region is from 10 mm to 80 mm, such as from 10 mm to 60 mm, such as from 10 mm to 50 mm, such as from 10 mm to 40 mm, such as from 10 mm to 40 mm, such as 15 mm to 35 mm, such as 20 mm to 30 mm.

The proximal region may be longer than the distal region, such as in the embodiments in FIG. 25-33, but in other embodiments the distal region may have the length as the proximal region. And as set forth above, the "proximal growth region" (e.g. 3304 in FIG. 33A) may not extend as far proximally as in the embodiments in FIG. 25-33 (but the implant may still be adapted to adequately facilitate ingrowth, including at the joint), so the proximal growth region could in some alternative embodiments be the same length or even shorter than the distal anchoring region.

In some embodiments the proximal growth region is longer than the distal anchoring region, and in some embodiments is 1-3 times the length of the distal anchoring region, such as 1.1 times-2.9 times the length of the distal anchoring region. For example, in the embodiment in FIGS. 33A-C, the proximal growth region is from 1-3 times the length of the distal anchoring region, and is from 1-2 times the length of the distal anchoring region. The relative lengths and ratio may depend on wherein the implant regions are disposed after implantation, and the function that is needed from the different implant regions based on the adjacent tissue.

The distal anchoring region (e.g. region 3302, 3102) may be a double lead threaded region, such as the embodiment in FIG. 33A-33C. For example without limitation, the thread pitch may be from 4 mm-8 mm, such as from 5 mm to 7 mm (e.g., 6 mm), with the threaded region having a 3 mm lead. The dual lead threaded region helps adapt the distal anchoring region for enhanced anchoring into the harder cortical bone. The implant 3100 shown in FIG. 31 also has a distal anchoring region with a dual lead threaded region.

In the embodiment in FIGS. 33A-33C, the inner component 3320 includes a shaft region 3322. The shaft outer diameter ("OD") is less than the inner diameter ("ID") of the outer sleeve 3340. In some embodiments the distance (i.e., the spacing) between the OD and the ID may be between 0.1 mm and 5 mm, such as from 0.5 mm to 3 mm. As set forth herein, this spacing creates the volume that facilitates growth therein.

In some merely exemplary embodiments, outer component 3340 (e.g. outer sleeve) can have a thread (e.g. 3103) that has a pitch that may be constant along most of its length, as is the case in FIGS. 33A-33. The pitch may be from 3 mm to 9 mm, for example (e.g., from 4 mm-8 mm, such as from 5 mm-7 mm, such as 6 mm), even if the thread has one or more discontinuities along its length (e.g. as in the embodiment in FIG. 31). The threaded region may be single lead along at least 50% of its length or more, as is the case in FIG. 31 and FIGS. 33A-33C, and in these embodiments the threaded region is single lead along at least 75% of its length. The pitch of the threaded region of the outer component can be designed to maintain enough surface area in the body of the outer component to create enough fenestrations (e.g. fenestrations 3114 or 3305), which can facilitate growth.

The outer component in FIG. 31 and in FIGS. 33A-33C includes a proximal region that is dual lead (e.g., 3303 and 3308 in FIG. 33C). Dual-lead and dual-thread are terms that may be used interchangeably in this disclosure. The dual (or double) lead region helps better anchor this region of the implant into the more dense cortex of the sacrum, similar to how the dual lead anchoring region of the implant can be dual lead to provide better anchoring in cortical iliac bone. Any of the implants herein can have this proximal dual lead region.

As set forth herein, the internal surface of the outer component 3340 can have an internal threaded region, which is configured to interface with external threaded region 3321 (see FIG. 33B) on the inner component 3320. This can help secure the internal and outer components.

In some embodiments the outer and inner components are adapted such that when assembled the outer component is put under compression due to the secured engagement between the two components. Components in bending may fail on the surface that is exposed to tension, so pre-stressing one or more components in compression can provide the benefit a higher working load range. Pre-stressing the outer component is, however, optional. Any of the implants herein can be pre-stressed in this manner to provide the benefit of a higher working load range.

With any of the implants herein, the distal end (or proximal end) of the outer component can be secured to the inner component while the proximal end (or distal end) is not secured to resist relative movement in at least one direction. By allowing the proximal end (or distal end) to be freely moveable relative to the inner component, the implant may beneficially be less likely to fatigue, due to fewer forces acting on the implant.

In alternative embodiments, the shaft region of the inner component (e.g. 3322 in FIG. 33B) may include one or more apertures or fenestrations therein, which may be a wide variety of sizes and configurations. Having one or more openings in the inner component could allow a substance (e.g. a therapeutic) to be delivered into an inner channel or bore in the inner component and out the openings, which could also pass through the opening (e.g., apertures, smaller fenestrations) in the outer component and interact with tissue.

It is understood that any suitable feature described with respect to any of the implants in FIG. 25-33 can be incorporated into any other embodiment in FIGS. 25-33, particularly if the feature can be clearly and easily incorporated therein.

Even if not specifically described, the implants disclosed in FIGS. 31-47 include a proximal end region that is configured to be coupled to a tulip, and is similar to the tulip or coupling devices or members at the proximal ends of the implants in FIG. 25-30. Any of the tulip or coupling devices described in the context of FIGS. 25-30 herein are expressly incorporated by reference into the embodiments in FIGS. 31-33. The tulip coupling members are configured to enable the implants to be coupled to other bone stabilization systems, which are described elsewhere herein.

Any of the exemplary features in any of the composite implants herein may be integrated or incorporated into other composite implant examples herein, unless specifically indicated to the contrary.

Figure 34A:
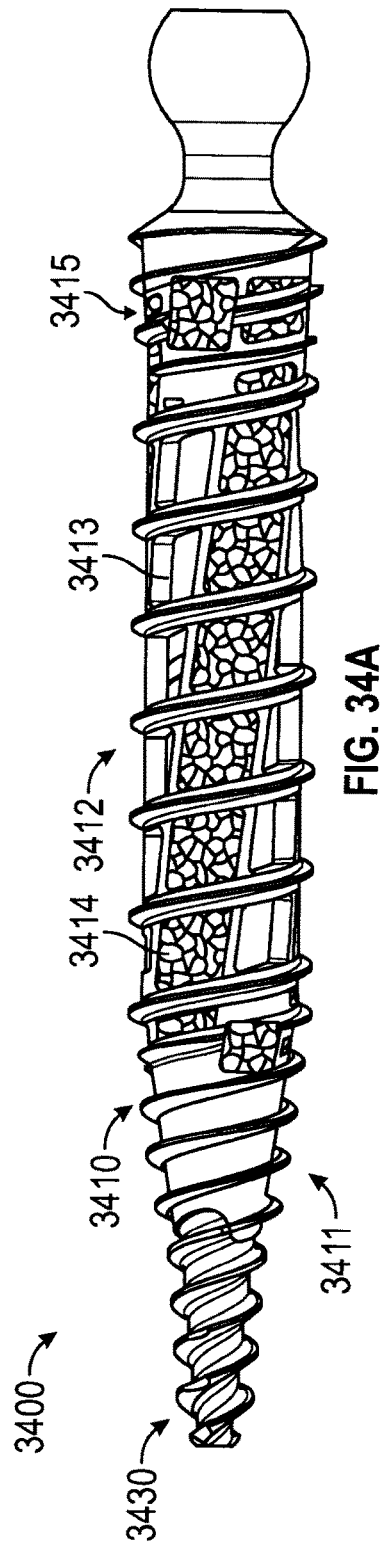
FIGS. 34A and 34B illustrate an exemplary composite implant.
Figure 34B:
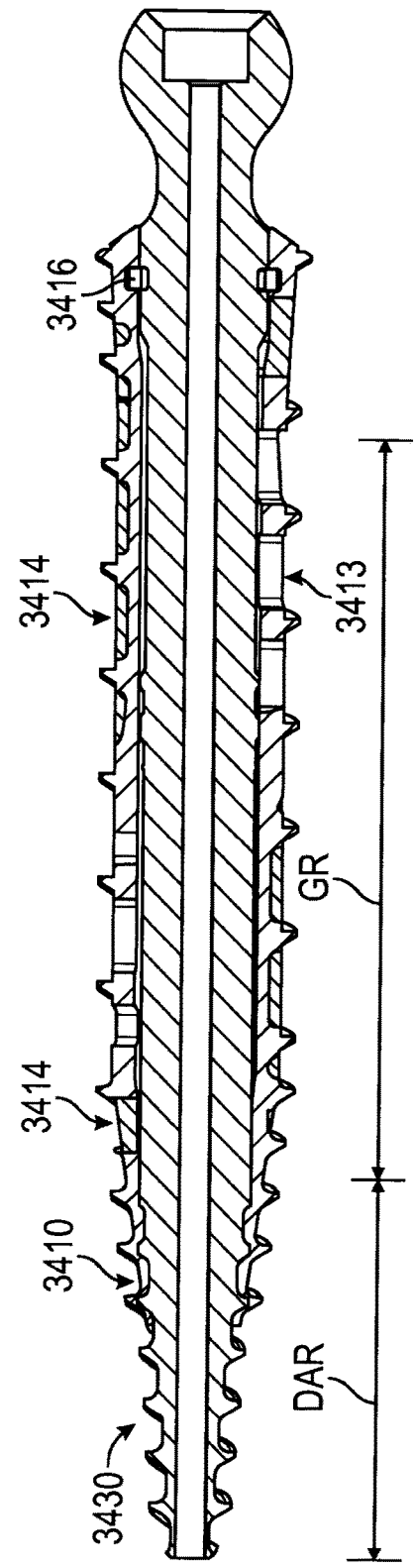

FIGS. 34A and 34B illustrate side views of an exemplary composite implant (assembled) that can be sized and configured for methods of implantation across a sacro-iliac (SI) joint via a posterior sacral alar-iliac ("SAI") trajectory, for example a posterior second sacral alar-iliac ("S2AI") trajectory. FIG. 34A is an assembled side view (without a tulip coupled thereto), while FIG. 34B is a sectional assembled view. Implant 3400 includes a sleeve 3410 and shank 3430, wherein the sleeve is sized and configured to be positioned over at least a portion of the shank. The sleeves herein have an inner lumen sized and configured to receive therethrough an inner member. The has one or more growth surface features adapted to facilitate at least one of bony on-growth, in-growth, or through-growth. The sleeve is positioned relative to the shank to form the composite implant with a shank interface feature and a sleeve interface feature interfacing each other so as to resist relative motion between the sleeve and shank in at least one direction. A shank herein may be referred to as an inner shank in cases where a sleeve is disposed around at least a portion of the shank. Inner and outer in this context refers to relative radial positions, relative to an optional long axis of the implant.

In this embodiment, sleeve 3410 is configured such that it can be front loaded over the shank 3430. That is, the distal end of the shank can be advanced into the proximal end of the sleeve (relative motion) to assemble the shank and sleeve into the assembled configuration shown in FIGS. 34A and 34B.

Sleeve 3410 includes a tapered distal threaded region 3411, any portion of which may be textured. In this embodiment tapered distal threaded region 3411 is a dual lead thread. Sleeve 3410 also includes central region 3412, which includes a single lead as shown, a plurality of fenestrations 3413, and a plurality of discrete lattice sections 3414 (only one labeled). In this example, each of (in other embodiments at least some of) the plurality of fenestrations 3413 is disposed between axially adjacent thread regions, as shown. In this example each of (in other embodiments at least some of) the plurality of lattice sections 3413 is disposed between axially adjacent thread regions, as shown. In this example multiple subsets of the plurality of fenestrations are each disposed to a partial helical configuration, as shown. In this example multiple subsets of the plurality of lattice sections are each disposed to a partial helical configuration, as shown.

Implant 3400 includes a distal anchoring region ("DAR" in FIG. 34B) and growth region ("GR" in FIG. 34B). The distal anchoring region includes one or more distal surface features (in this embodiment threads) that better adapt the distal anchoring region for anchoring into iliac bone than the growth region. The growth region includes one or more growth features that better adapt the growth region to facilitate at least one of bony on-growth, in-growth, or through-growth than the anchoring region (such as more fenestrations 3413, more lattice sections 3414 and single thread versus dual threads).

Figure 36A:
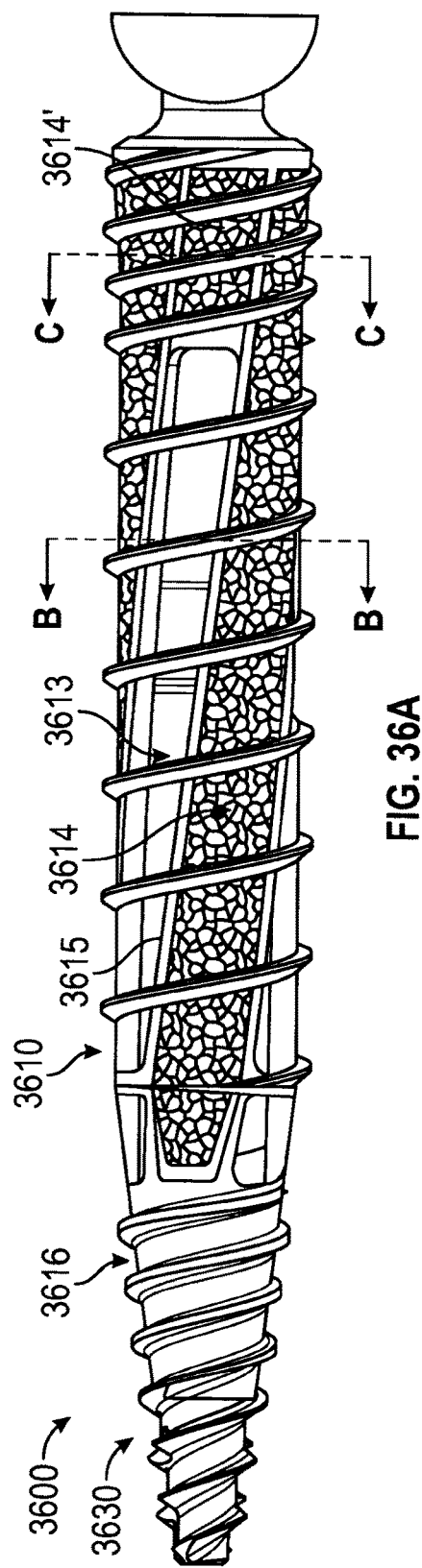
FIGS. 36A-36C illustrate views of an exemplary composite implant.
Figure 36C:
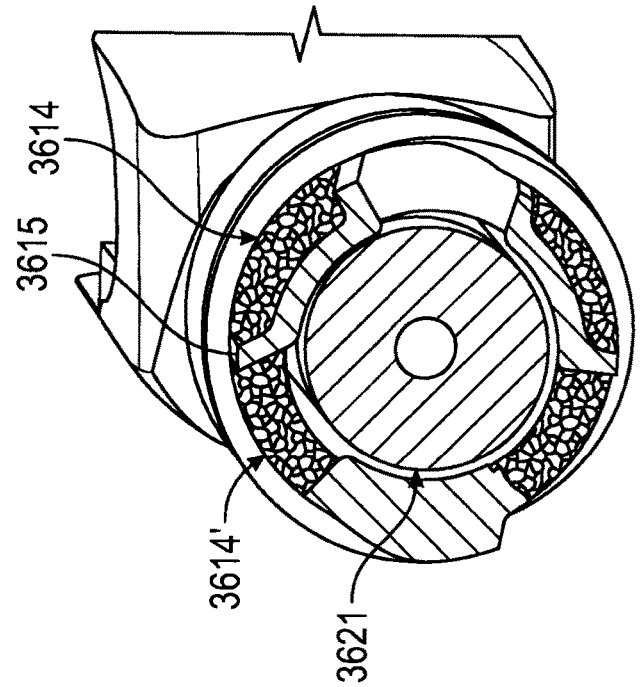
Figure 36B:
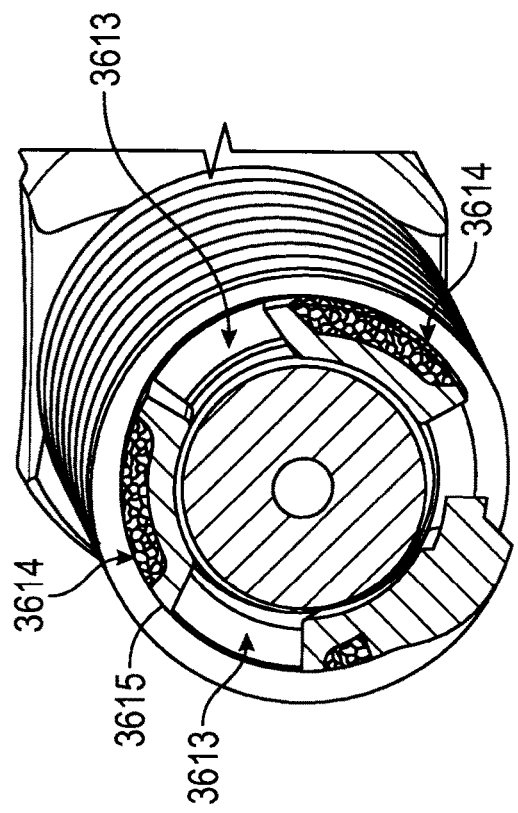

FIGS. 36A-36C illustrate an exemplary composite implant 3600 that can include any relevant feature of any composite implant (multi-component) herein. Any features not specifically described may be incorporated by reference into this embodiment from other examples herein. Similar features may be similarly labeled in the figures. Implant 3600 includes sleeve 3610 and shank 3630. In the embodiment in FIGS. 36A-C, sleeve 3610 includes a distal tapered threaded region as shown. The distal tapered threaded region includes optional textured surface 3616 on the minor diameter of the threads. As shown in Section B-B from FIG. 36A, as shown in FIG. 36B, lattice sections 3614 are disposed in the sleeve flutes 3615, and the lattice sections 3614. In Section C-C from FIG. 36A, as shown in FIG. 36C, however, the sleeve also includes lattice sections 3614' that fill the cutting fluid void. In this proximal region of the sleeve, the lattice sections 3614' essentially fill in, or take the place of, apertures 3613. These through lattice sections 3614' can increase the amount of tissue growth through sections 3614'. Also shown in FIG. 36C is a volume (or void) defined between the shank outer dimension and the sleeve inner diameter, in which tissue ingrowth can occur.

The sleeve in FIG. 36A-36C is adapted to be front loaded onto the shank. Front loading the sleeve makes it easier to match the locations of the threads on the sleeve and shank.

In any of the composite implant examples herein, the sleeves may be manufactured by printing.

Figure 35:
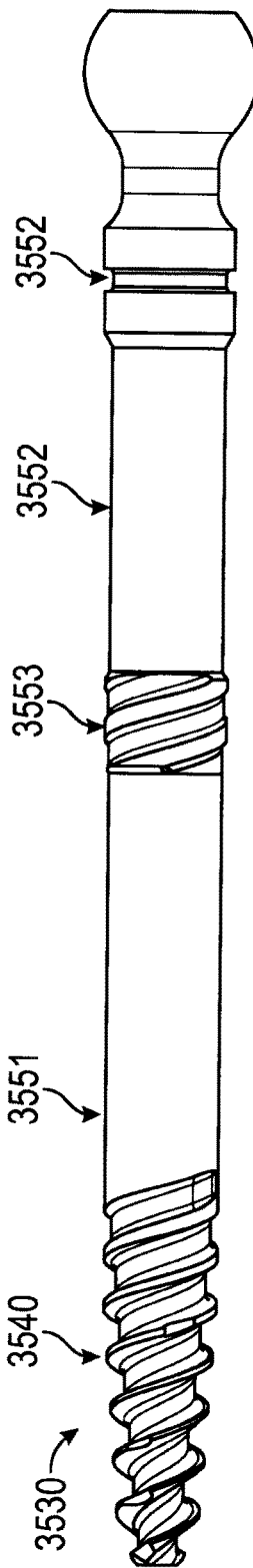
FIG. 35 illustrate an exemplary inner member.

FIG. 35 illustrates an exemplary shank 3530. Any of the shanks herein may also be referred to as an inner member. Shank 3530 includes a distal region 3540, which is threaded in this embodiment and has a dual thread in this embodiment. Distal region 3540 is tapered.

The shank includes a section 3551 and a section 3552, with section 3553 axially in between. Either or both of sections 3551 and 3552 may be textured, such as with TPS, grit blast, HA, for example without limitation, to facilitate one or more of in growth, on-growth, or through growth. Section 3553 can include a central thread as shown. The thread in central section 3553 may be made with the same thread pass as the pass creating the threads on the distal shank section. A benefit of the thread in central section 3553 can be that it creates volume between the sleeve and shank that can increase graft volume while providing support to the sleeve.

Any of the inner members herein, such as any shank herein, can be manufactured by machining the inner member. In some embodiments the inner member can be machined out of a solid material such as titanium. The central rib in section 3553 is an example of a central rib that can be configured to reduce the bending moment on the shank. This can be helpful for relatively longer shank lengths, such as 80-120 mm length shanks.

Figure 37:
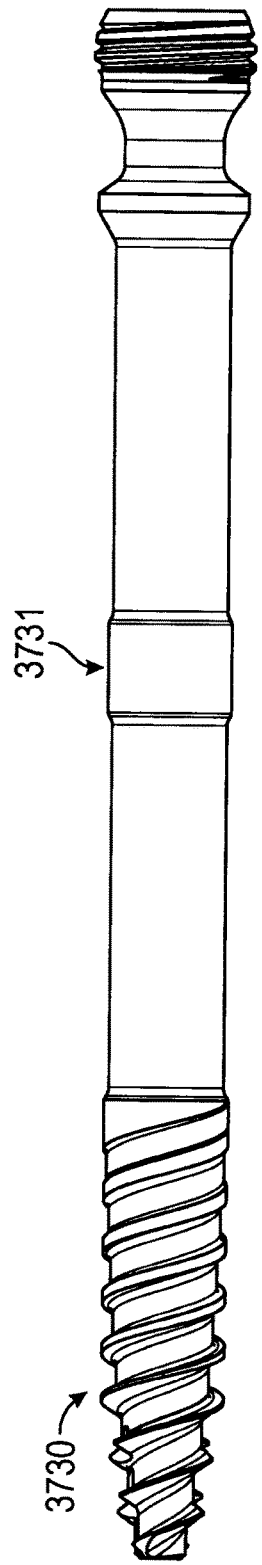
FIG. 37 illustrates an exemplary inner member.
Figure 38:
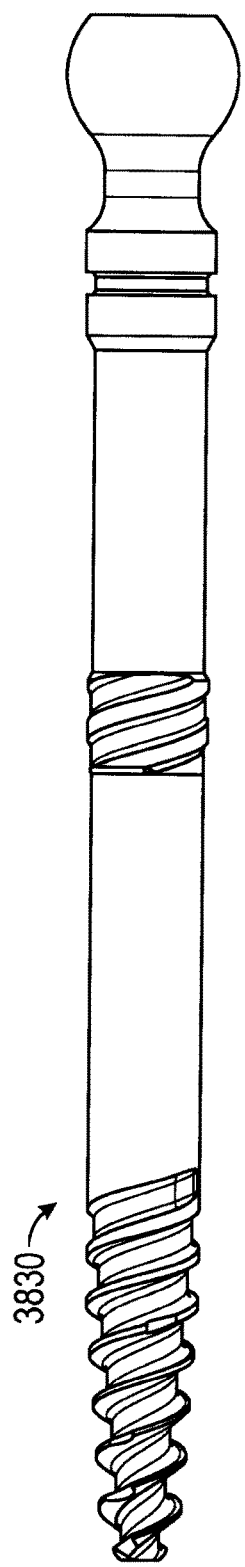
FIG. 38 illustrates an exemplary inner member.
Figure 39:
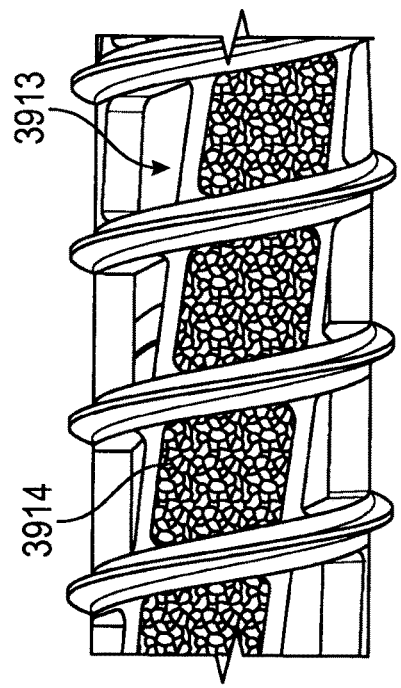
FIG. 39 illustrates a portion of an exemplary composite implant.

FIG. 37 illustrates a shank 3700 that includes a central rib 3731. The central rib 3731 is a region with a larger radial dimension than adjacent sections of the shank, as shown in FIG. 37. The rib can increase graft volume, while optionally help stabilize the sleeve.

Any of the shanks herein (one any section thereof) may have one or more holes therethrough, such as to facilitate post-implant administering one or more agents (e.g. PMMA into the ilium).

In any of the examples herein, the sleeve apertures herein may have one angled edge to help cut bone while screwing the implant into position, and the other edge can be straight, as shown in the examples in FIGS. 34A-47. This can help self-harvest the bone and help fill the fenestrations with bone.

Figure 40:
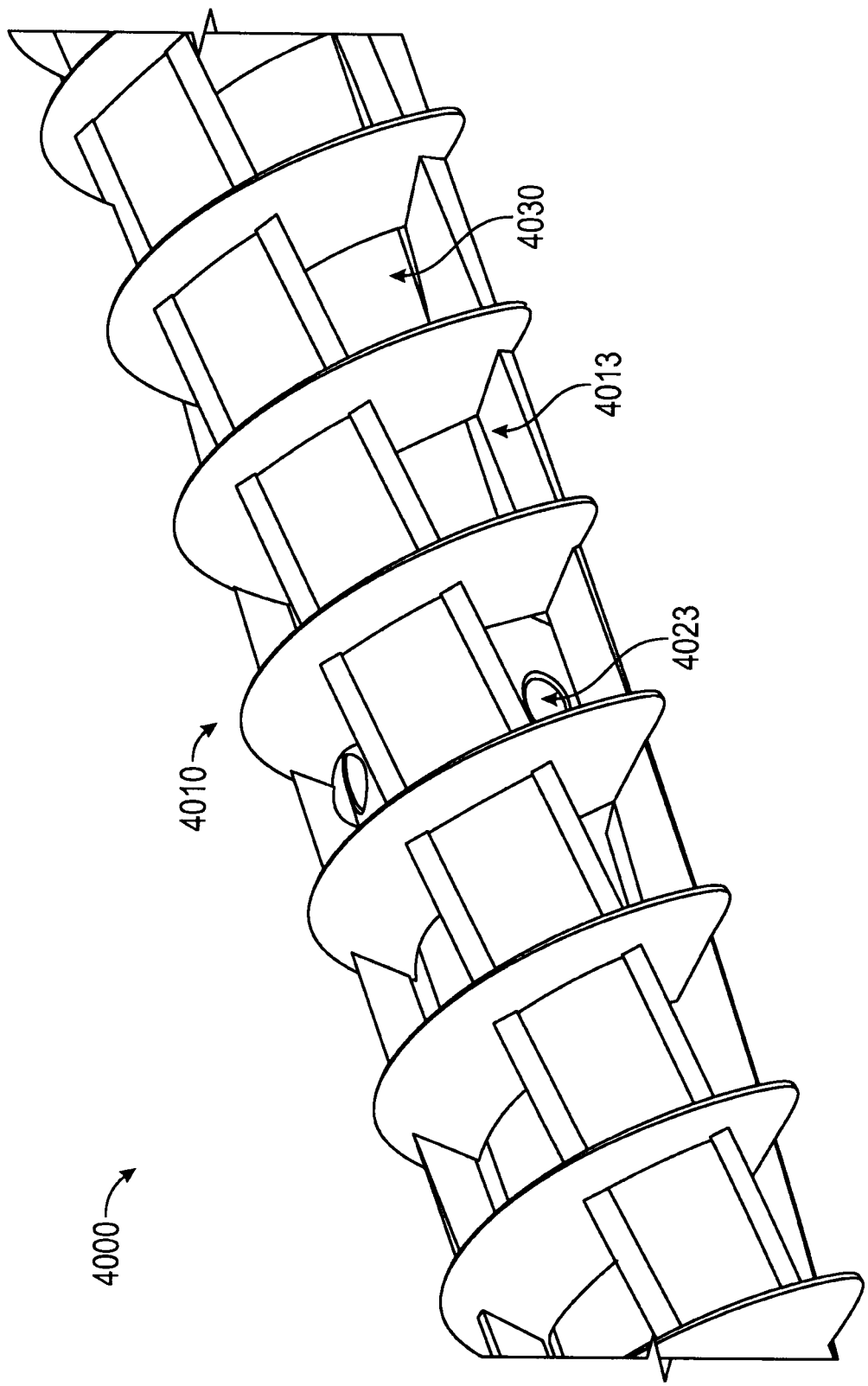
FIG. 40 illustrates a portion of an exemplary composite implant.

FIG. 40 illustrates a portion of composite implant 4000 that includes sleeve 4010 and shank 4030. Optional apertures 4013 are also shown. Any other feature from any other embodiment herein can be incorporated into implant 4000. Implant 4000 includes a shank 4030 that includes optional plurality of holes 4023 that are adapted to function as post-fill graft ports. The holes 4023 can communicate with an inner shank volume to facilitate post-implant filling. In this embodiment apertures 4023 are optionally aligned with holes 4023.

FIGS. 41A and 41B illustrate exemplary composite implant 4100 that includes sleeve 4110 and shank 4130. In this embodiment (or any other embodiment herein), sleeve 4110 includes cutting flutes in the distal region. In this exemplary embodiment, cutting flutes have a 15 degree to 25 degree cutting face 4128, as shown in FIG. 41B. The cutting faces may be angled at other degrees. Implant 4100 includes any other features of any other composite implant herein.

The implant may have one or more ways in which the sleeve interacts with the shank to help stabilize the sleeve relative to the shank when assembled. For example, the shank can have a shank interface feature and the sleeve can have a sleeve interface feature that are configured to interface with each other so as to resist relative motion between the sleeve and the inner shank in at least one direction (e.g. axial, radial, rotational). For example, the sleeve and shank may interface in one or both of a distal anchoring region and a proximal region of the implant to help stabilize the sleeve relative to the shank. In some examples the shank and sleeve do not interface in a central region of the implant.

Figure 42:
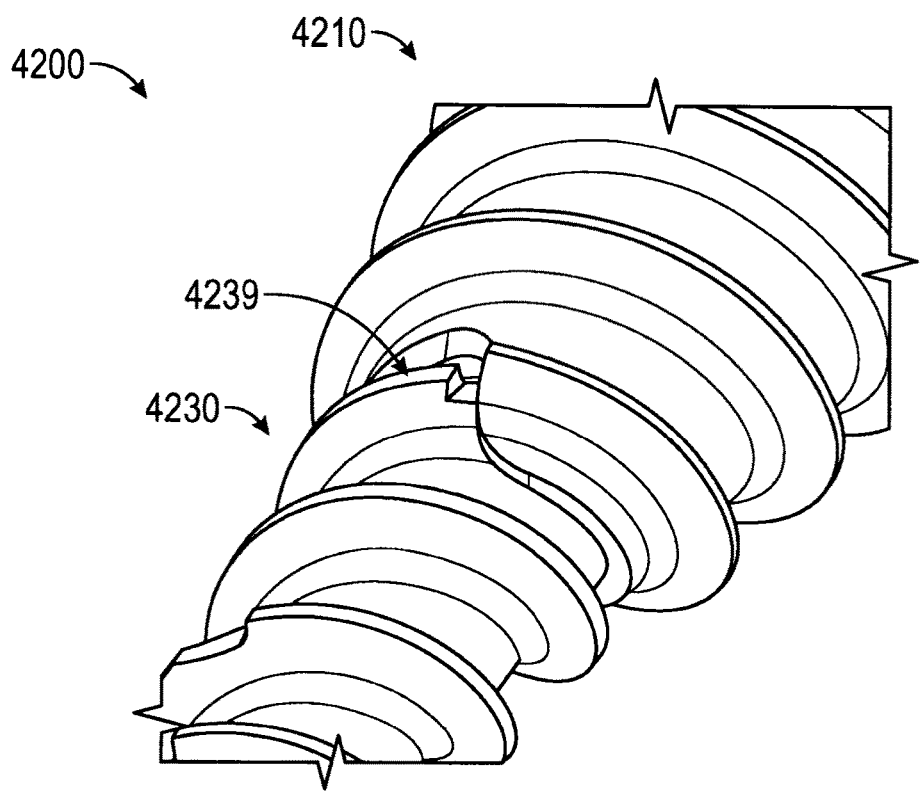
FIG. 42 illustrates a portion of an exemplary composite implant.

For example, the shank 4230 may include, in the distal threaded region, a detent, depression, or barb 4239 in a thread, as shown in FIG. 42. The barb 4239 can be configured to interface with the sleeve to prevent sleeve 4210 from advancing too far distally relative to the shank. This may function as a back-up or secondary stop feature if a primary locking mechanism fails.

Figure 43:
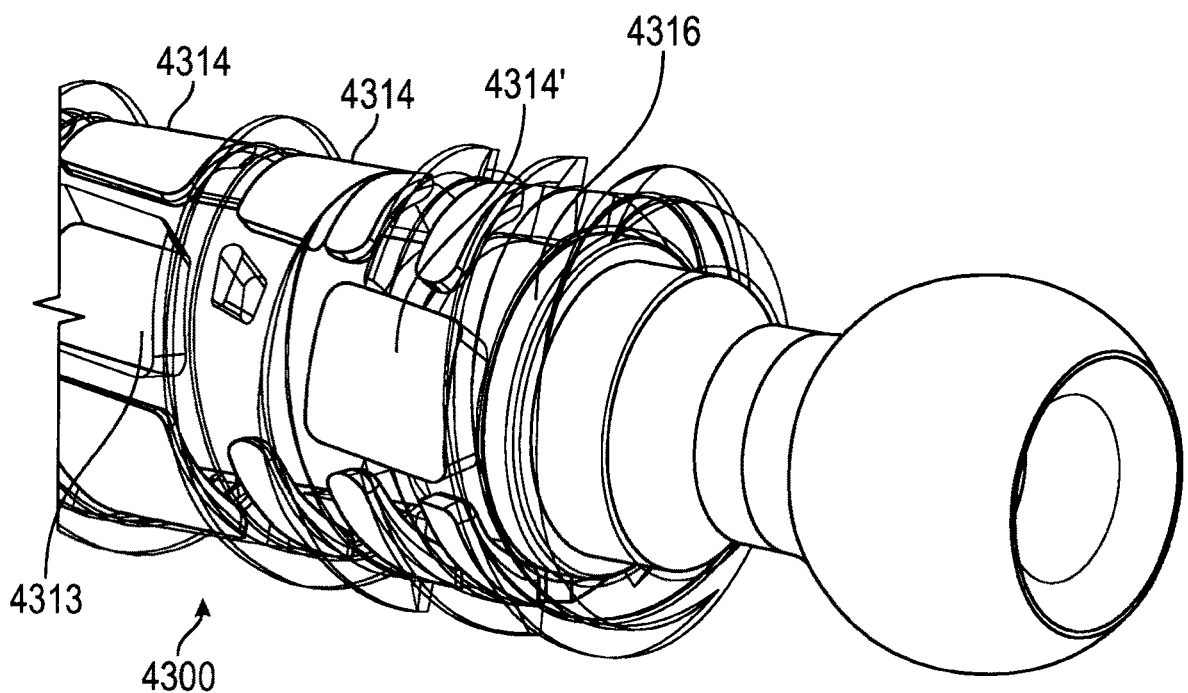
FIG. 43 illustrates a portion of an exemplary composite implant.

The sleeve and the shank may alternatively or in addition to interface in a proximal end region of the composite implant to resist relative movement therebetween in at least one direction. FIG. 43 illustrates an exemplary proximal end region locking mechanism, which may be incorporated into any of the composite implants herein. The side sectional view of FIG. 34B also includes the same or similar proximal end region locking mechanism as that shown in FIG. 43. Composite implant 4300 is shown with the sleeve in a model view with lattice regions 4314 and 4314' illustrated as solid regions. Locking ring 4316 (which can be the same or similar to locking ring 3416 in FIG. 34B) is a separate component, which is configured to snap into grooves in the shank and the sleeve during assembly of the shank and sleeve. The optional annular lock ring functions to prevent potential migration of a loose sleeve.

Figure 44A:
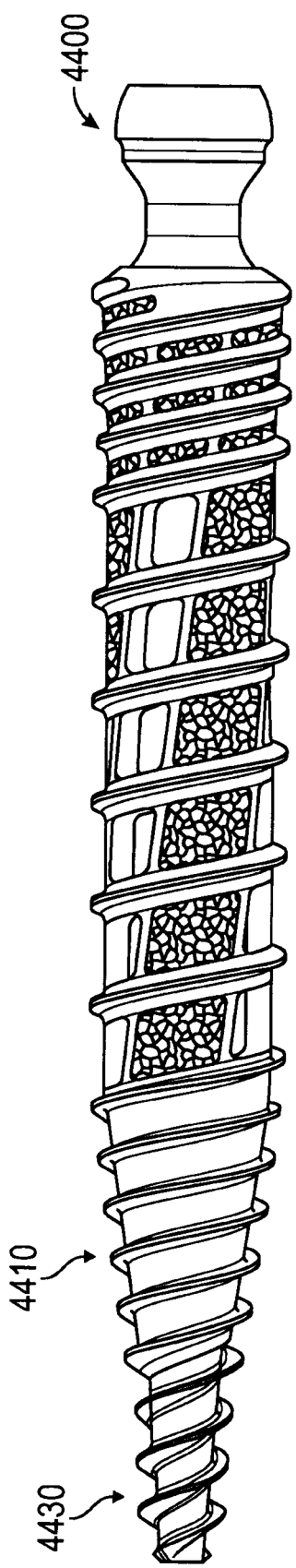
FIGS. 44A and 44B illustrates views of an exemplary composite implant.
Figure 44B:
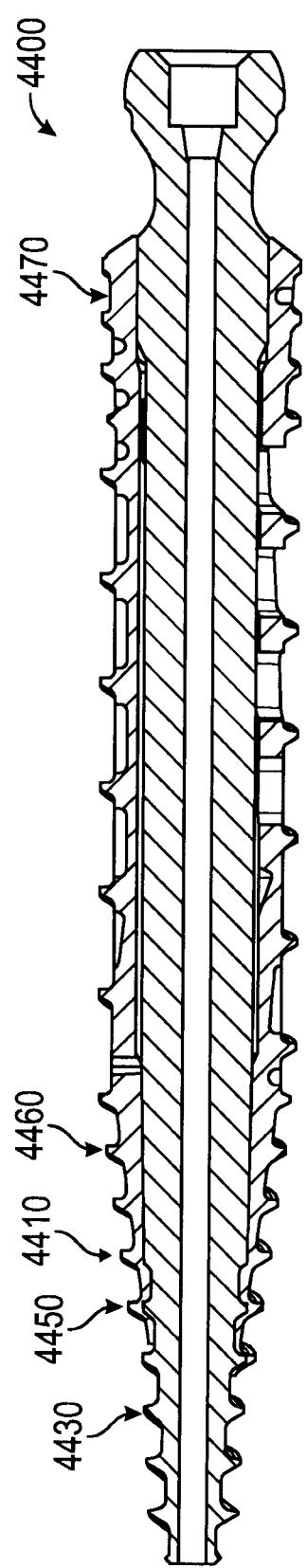
Figure 44C:
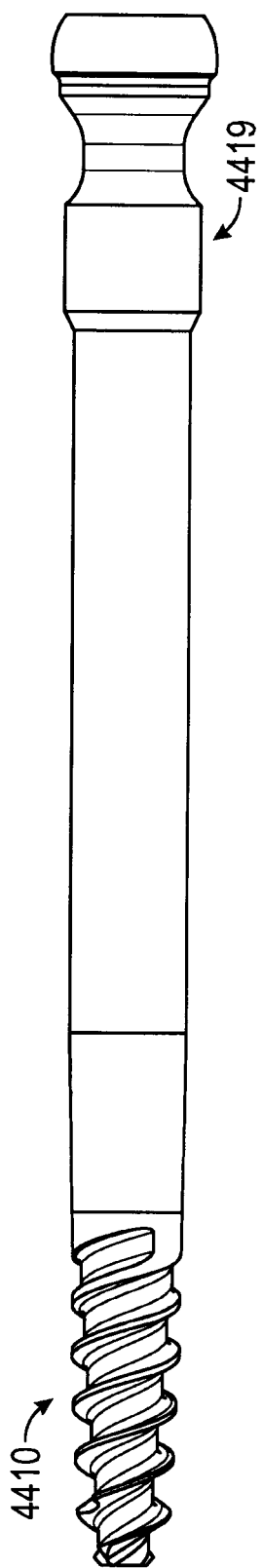
FIG. 44C illustrates an exemplary inner member.

FIGS. 44A-C are side views of an exemplary composite implant 4400 (FIG. 44C shows shank 4410). FIG. 44B is a side sectional view. FIGS. 44A-44C illustrate additional or alternative ways in which the sleeve and shank can interface to resist relative motion therebetween in at least one direction. The shank and sleeve can have interference-fit threads in thread interface region 4450, as shown in the sectional view of FIG. 44B, which can help resist relative motion between the shank and sleeve. Any portion(s) of the threads may have no clearance therebetween. In these embodiments the sleeve includes internal threads in the distal end region that are configured to interface with the outer threads on the shank.

Alternatively or in addition to, the shank/sleeve interface can include a tapered locking connection in tapered locking connection region 4460. At this interface region the shank and sleeve can include distal tapers as shown, which together form a taper lock.

Alternatively or in addition to, the shank/sleeve interface can include a proximal end region interface in region 4470, which in this embodiment includes a tight sliding fit between optionally smooth surface of the sleeve and shank. The surface 4419 of the shank that sleeve interfaces with is shown in FIG. 44C. FIGS. 44A-44C is an example of a composite implant in which the sleeve and shaft interface in distal end regions and proximal end regions, but does not interface in a central region in between the distal and central regions.

In any of the embodiments herein, the sleeve and shank can interface in a distal region, such as in one or both of regions 4450 and/or 4460 in FIG. 44B, but may not interface in a proximal region (e.g., optionally not in region 4470 in FIG. 44B).

Additionally, if the sleeve and shank interface in a proximal region, the proximal interface region may provide for some relative movement between the sleeve and shank, but can still provide some degree of overall resistance to movement therebetween in at least one direction.

FIGS. 45A and 45B illustrate (in side and sectional side views, respectively) an exemplary composite implant 4500, including sleeve 4510 and shank 4530. Implant 4500 may alternatively or in addition to include any of the features herein of any other composite implant. Shank 4530 illustrates an example of how distal threaded region 4541 and proximal threaded region 4542 may be cut from a blank starting material during the same step so that the threads share the same start. Proximal threaded 4542 can be dual-lead thread as shown, similar to other embodiments shown herein. Region 4519 of outer sleeve is dual-lead, as with other embodiments herein.

FIG. 45B illustrates an exemplary shank/sleeve distal interface that includes a threaded interface between sleeve 4510 and shank 4530. In the interface region 4538 as shown, the shank thread crest optionally becomes gradually flatter in the proximal direction, as shown. That is, the crest is less flat further distally in region 4538 and becomes flatter moving proximally, as shown in FIG. 45B.

Implant 4500 is an example of a composite implant in which the sleeve can be placed under compression upon assembly of the shank, for exemplary benefits set forth herein. For example, components in bending may fail on the surface that is exposed to tension, so pre-stressing one or more components in compression can provide the benefit of a higher working load range. Pre-stressing the outer component is, however, optional. Any of the implants herein can be pre-stressed in this manner to provide the benefit of a higher working load range. Implant 4500 includes shank 4530 that includes stop 4539 in the configuration of a shoulder, as shown. The stop 4339 provides a mechanical stop for sleeve 4510 and help compress the sleeve (pre-strain), for reasons set forth herein. One separate aspect of this disclosure is thus a composite implant wherein an outer member (e.g. sleeve) is put under compression when interfaced with an inner member (e.g. shank). One of the optional benefits of pre-straining/pre-compressing the sleeve would be in cases where the sleeve might or would be more likely to break before the shank due to material properties of the sleeve compared to the shank.

Figure 46A:
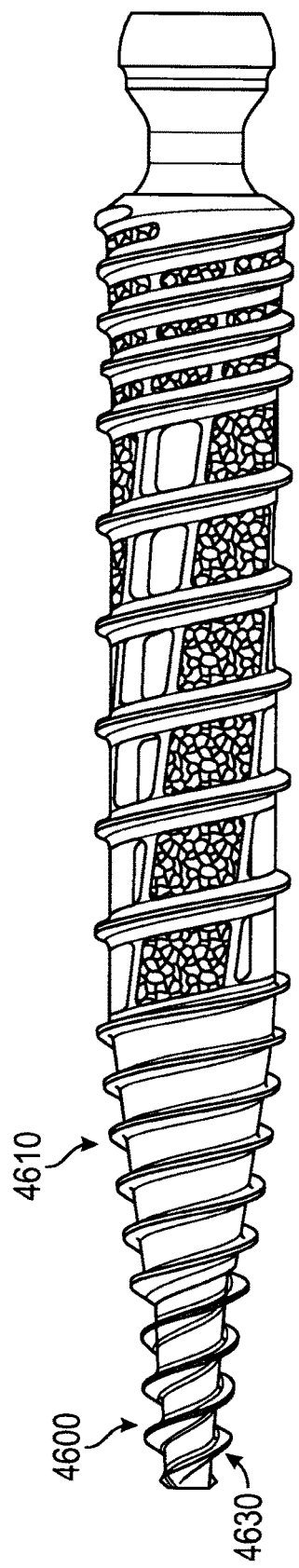
FIGS. 46A-46D illustrates views of an exemplary composite implant.
Figure 46B:
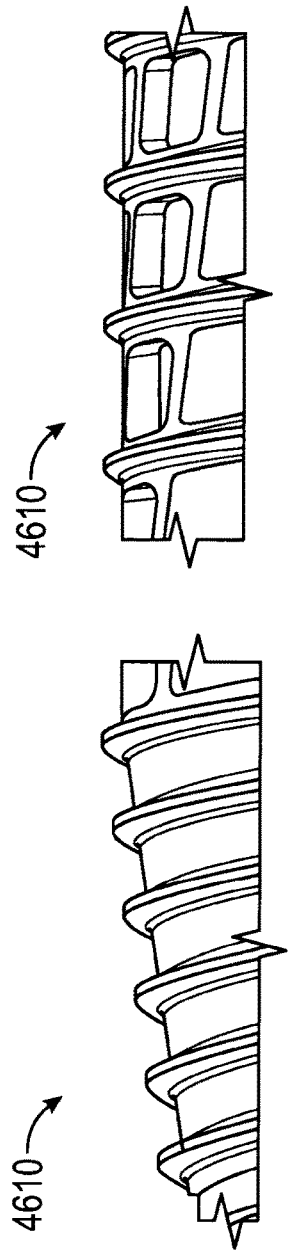
Figure 46C:
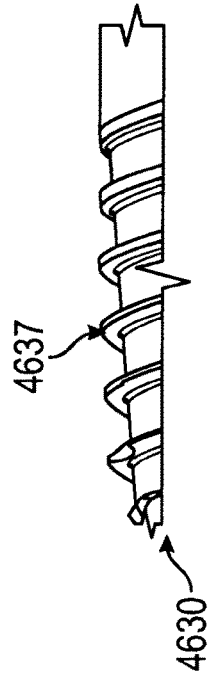
Figure 46D:
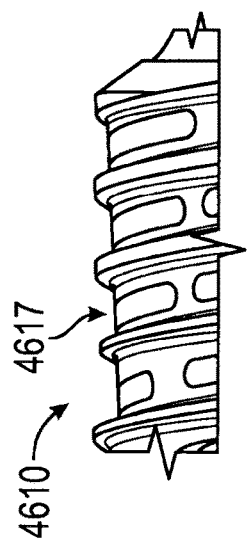
Figure 46E:
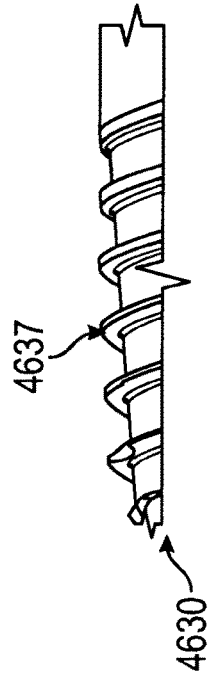
FIG. 46E illustrates an exemplary inner member.

FIG. 46A illustrates an exemplary composite implant 4600, including sleeve 4610 and shank 4630. Implant 4600 may alternatively or in addition to include any other features of other composite implants herein. The other composite implants herein may include any feature of implant 4600. FIGS. 46B-46D illustrate exemplary features of exemplary sleeve 4610. Any of the sleeves herein may be 3D printed, for example. In the sleeve distal thread region shown in FIG. 46B, the thread may have a 5° to 15° back flank angle, for example. FIG. 46C illustrates a central region of exemplary sleeve 4610 in the more centrally disposed growth region of the implant. In this threaded region the thread may have a 0° to 3° back flank angle, for example. FIG. 46D illustrates a proximal region of sleeve 4610, which has a dual lead thread. As shown, the sleeve minor diameter surface 4617 tapers radially outward from the distal end to the proximal end, as shown in both FIG. 46A and 46D. The major diameter can be maintained constant or substantially constant. The thread may have a 0° to 3° back flank angle, for example. FIG. 46E illustrates a distal end region of exemplary shank 4630. Any of the shanks herein may be machined using a variety of known machining processes. Thread 4637 has a small flat at the crest, as shown, which gradually increases in length in the proximal direction, also as shown. The distal shank thread may optionally include a plurality of cutting flutes in this region, optionally first and second flutes that are 180 degrees from each other. The distal shank thread may optionally have a 10° to 15° back flank angle, for example.

Figure 47:
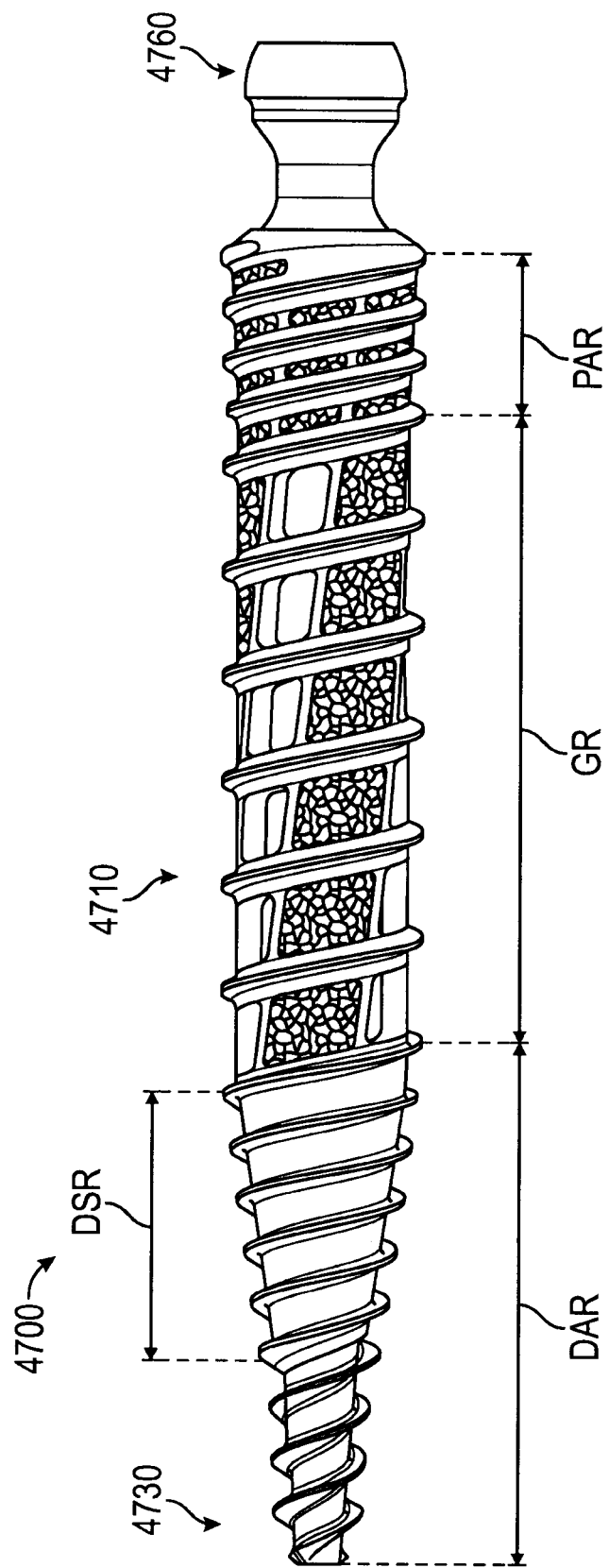
FIG. 47 illustrates an exemplary composite implant.

FIG. 47 is a side view that illustrates an exemplary composite implant 4700 that includes outer member 4710 (e.g. sleeve) and inner member 4730 (e.g. shank). The inner member, like any of the inner members herein, can include a proximal end 4760 that is configured to be coupled to a tulip, to which a reinforcing rod may be secured (details of which are described herein). As set forth herein, different regions of the implant can be configured to facilitate one or more functions once implanted (e.g. distal anchoring region, growth region, proximal anchoring region, etc.). Those regions can have lengths such that when implanted based on a trajectory (or range of general trajectories, such as posterior sacral alar-iliac ("SAI") trajectories) the regions will be adjacent certain anatomical regions to better adapt them to perform those functions than other regions of the implant.

In some embodiments, a distal anchoring region ("DAR" in FIG. 47) of an implant (e.g. composite implant) may have a length from 15 mm to 40 mm, such as from 15 mm to 35 mm, such as from 15 mm to 30 mm, such as from 20 mm to 30 mm, such as 25 mm.

In some embodiments, a growth region (e.g. "GR" in FIG. 47) of an implant (e.g. a composite implant) may have a length from 25 mm to 65 mm, such as from 30 mm to 60 mm, such as 30 mm to 55 mm, such as 35 mm to 55 mm, such as 45 mm.

In some embodiments, a proximal anchoring region (e.g. "PAR" in FIG. 47) of an implant (e.g. a composite implant) may be from 3 mm to 20 mm, such as 5 mm to 15 mm.

In some embodiments, an overall screw length of the implant (such as a composite implant), which may a combination of DAR, GR, and PAR, in some embodiments, may be from 60 mm-100 mm, such as 65 mm to 95 mm, such as 70 mm, to 90 mm, such as 75 mm to 85 mm, such as 80 mm.

In some embodiments, an overall implant length (such as a composite implant), which may a combination of DAR, GR, optional PAR, and proximal coupling region 4760, may be from 65 mm-110 mm, such as 70 mm to 105 mm, such as 75 mm, to 100 mm, such as 80 mm to 95 mm, such as 85 mm.

With reference to FIG. 47, in methods of use, distal anchoring region DAR may be implanted in an ilium. Growth region GR may be implanted across an SI joint, and proximal anchoring region PAR may be implanted in a sacrum. A tulip can be coupled to proximal coupling region 4760, and a stabilizing rod can be secured to the tulip. More than one composite implant can be positioned across an SI joint in the trajectories described herein. One or more stabilizing rods may be secured to any number of implanted composite implants herein.

Figure 48A:
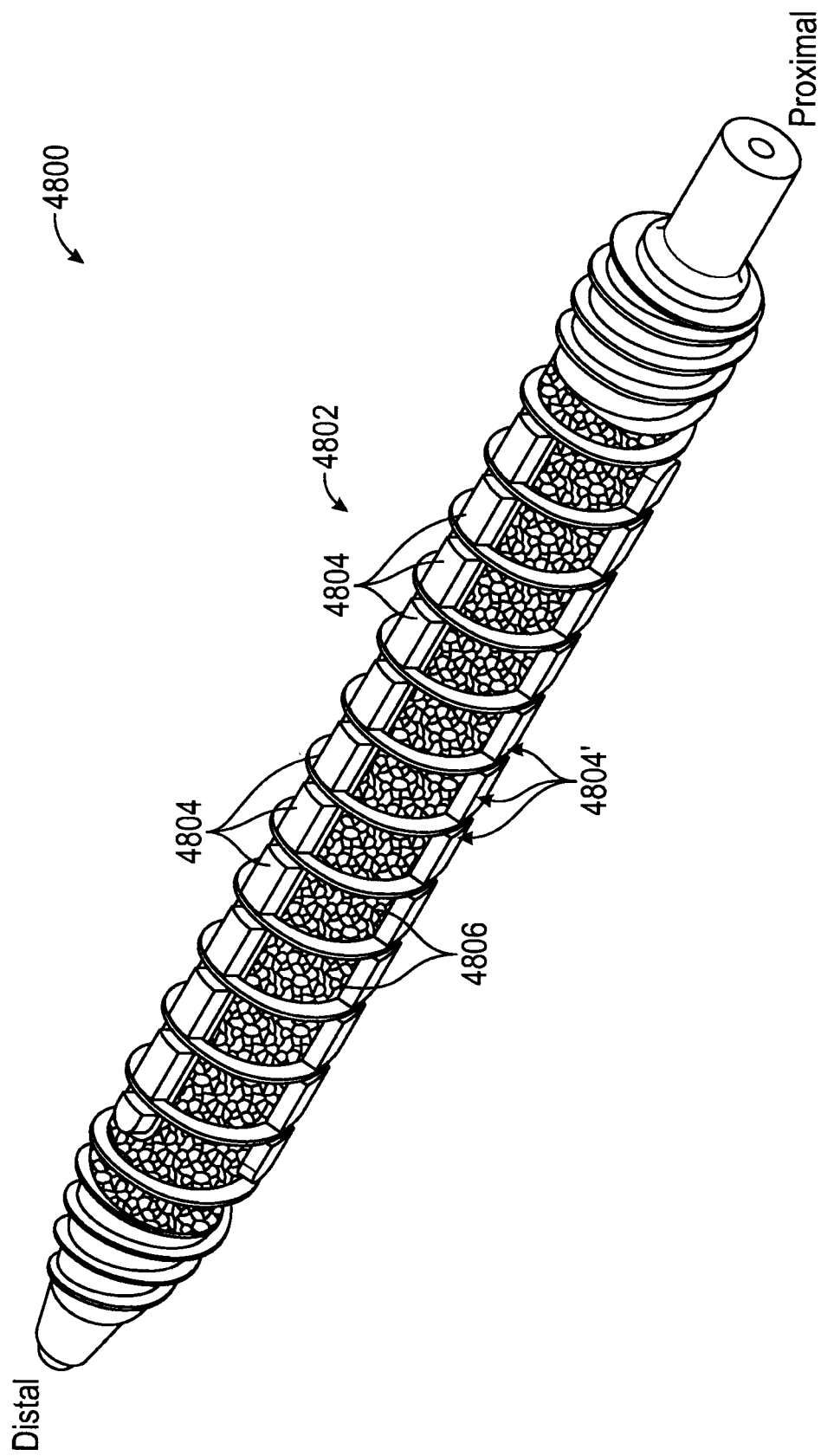

One aspect of this disclosure is related to bone stabilizing implant that includes one or more deployable members, the one or more deployable members having non-deployed configurations and a deployed configuration. FIGS. 48A-48H illustrate an exemplary embodiment of a bone stabilizing implant that includes one or more deployable members. FIG. 48A is a perspective view of exemplary bone stabilizing implant 4800 including an elongate implant body 4802 and a plurality of deployable members 4804 and 4804' (only some or each are labeled for clarity). The deployable members in this embodiment may generally be referred to as protrusions or fins, and in FIG. 48A are shown in their deployed configurations. If the term "fin" or "fins" is used in the text or figures, the more generalized term "deployable member(s)" is understood to apply as well. FIG. 48B shows deployable members in deployed configurations/positions, while FIG. 48C shows the deployable members in non-deployed (e.g., recessed) configurations/positions.

Figure 48D:
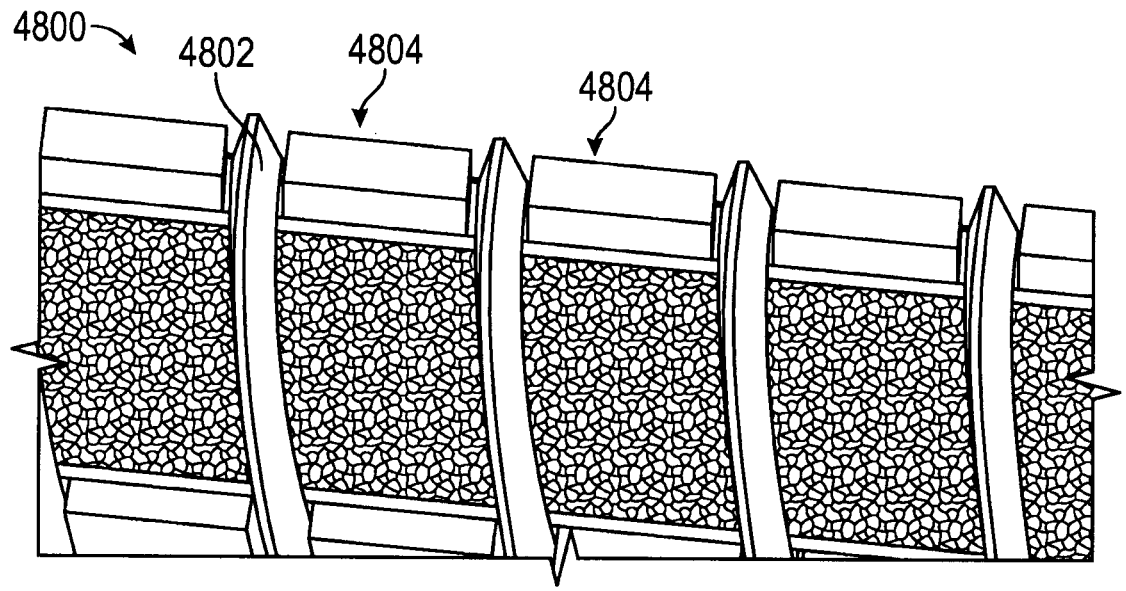

FIG. 48D shows a side view of implant 4800. FIG. 48D illustrates threads of the elongate implant body 4802 pass through openings between adjacent deployable members 4804. The threads thereby provide a mechanical stop for the deployable members 4804 by limiting upward travel, and prevent the opening from bowing under load. The deployable members are deployed.

Figure 48E:
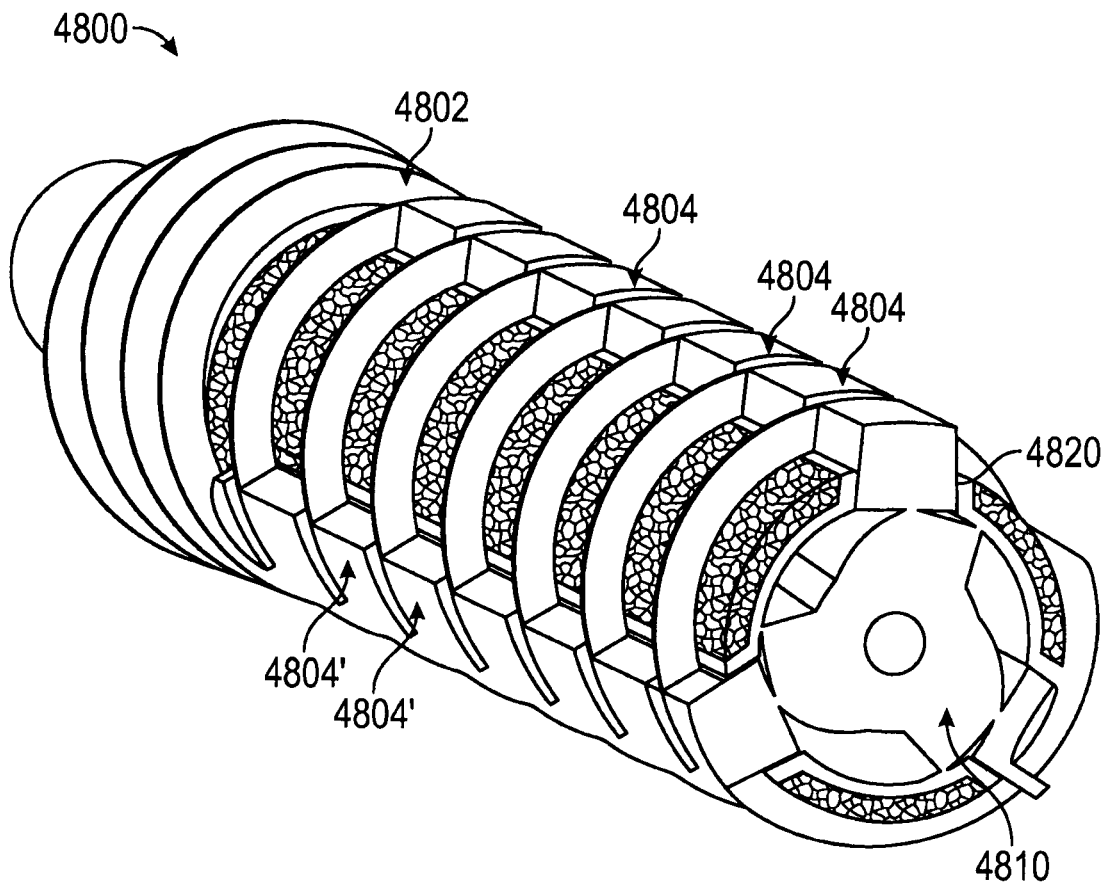

FIG. 48E shows a perspective sectional view of the implant in the region shown in FIG. 48D. FIG. 48E shows internal deployment member 4810, which can be part of the implant or a deployment tool that is not part of the implant and is removed from the patient following the deployment step. The internal deployment member can be function as a camming member, and when rotated has camming surfaces that urge the deployable member(s) radially outward to their deployed positions/configurations. The internal deployment member 4810 may stay in place with the implant, and may help the deployable members stay in their deployed configurations. The openings 4820 in the elongate body 4802 (through which the deployable members extend), one of which is labeled in FIG. 48G can be tapered to limit the play between the deployable members and the elongate implant body 4802. In some embodiments the internal deployment member 4810 may be made titanium (for example without limitation), and may be manufactured with subtractive manufacturing techniques. The deployable member(s) may in some embodiments be titanium (for example without limitation), and can be manufactured using subtractive manufacturing techniques.

Figure 48F:
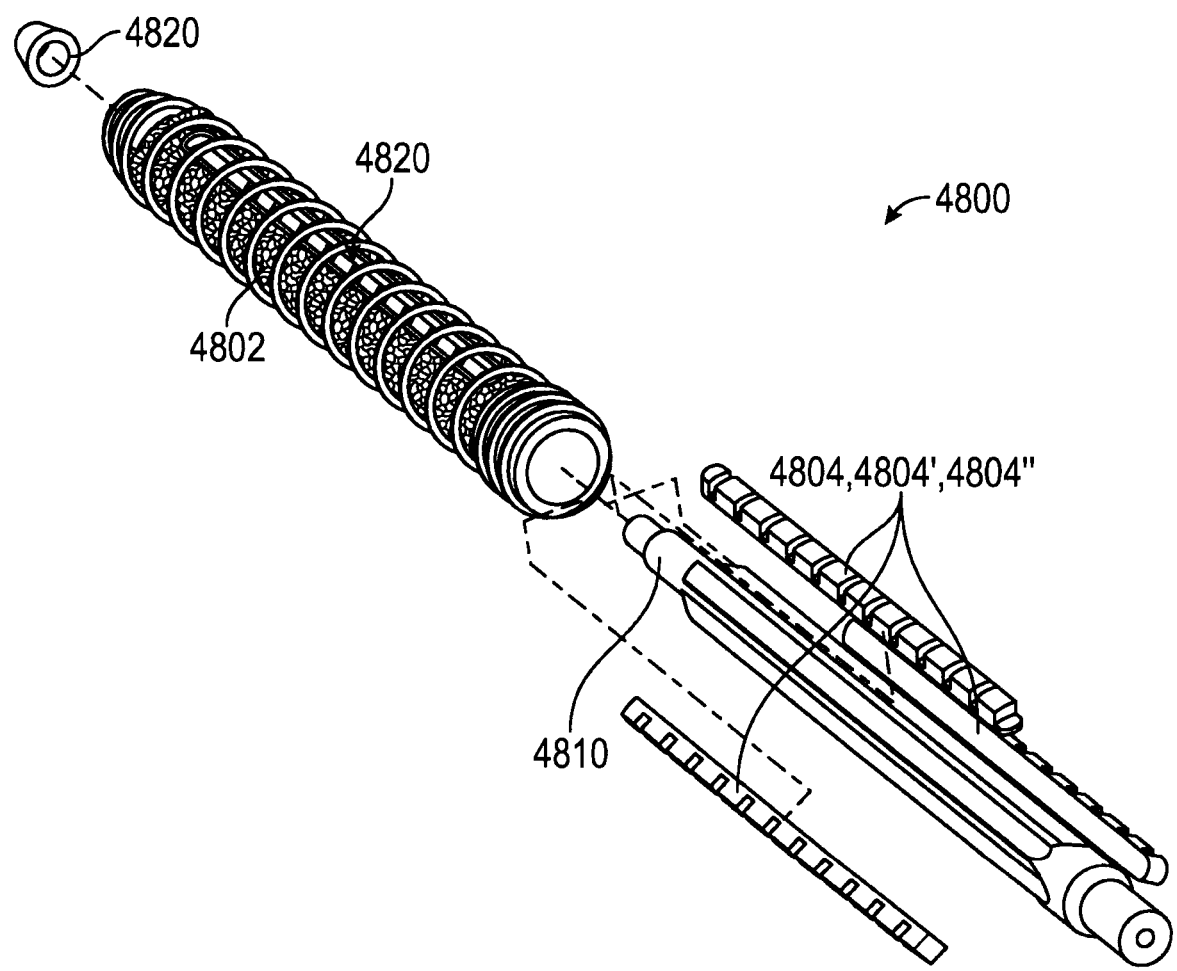

FIG. 48F shows an exemplary exploded view of implant 4800. Implant 4800 includes elongate body or sleeve 4802, which is threaded as shown and includes a plurality of sets of linear openings 4820 separated by the threads. The implant includes deployable or expandable members 4804, which in this embodiment are each coupled to a spine from which each of the deployable members 4804 extends, as shown in FIG. 48F. The spine and deployable members may be integrally formed from the same material or not. The linear spine and deployable members are disposed within the body 4802, and urged radially outward by actuation member 4810, details of which are shown in FIG. 48E. Threaded tip 4820 can be coupled to the distal end region of body 4802 using a variety of coupling techniques.

Figure 48G:
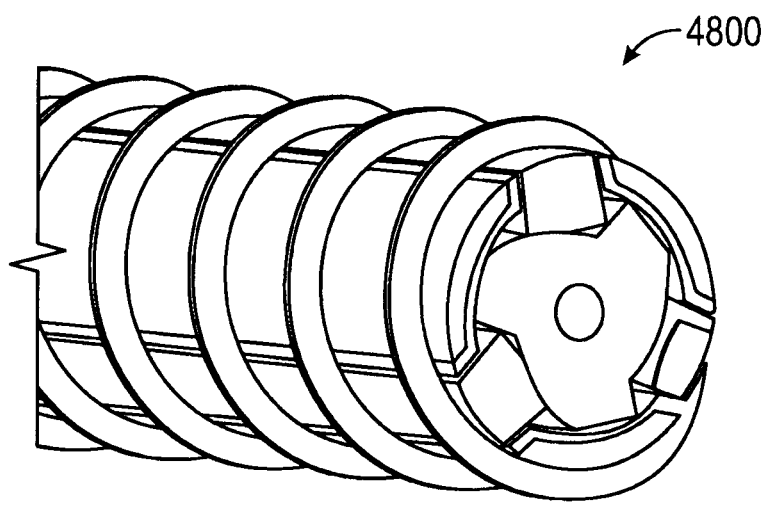
Figure 48H:
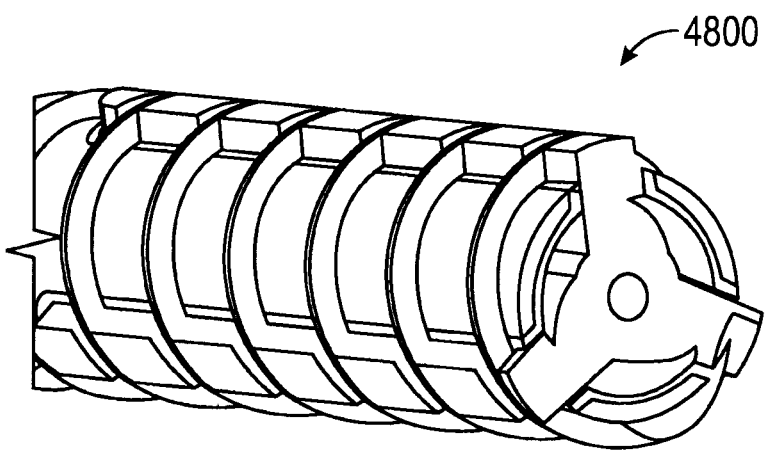

FIGS. 48G and 48H illustrate perspective sectional views of implant 4800 in non-deployed (FIG. 48G) and deployed (FIG. 48H) configurations. Additional details are shown in other figures within FIG. 48A-48F.

Exemplary methods of implanting implant 4800 can include one or more of following steps, and may not necessary be in the order that follows. During implant insertion, the deployable members 4804, 4804', 4804" are in non-deployed (e.g. recessed) positions relative to implant body 4802. The implant can be threaded into bone similar to a screw. After the implant is located in a target location, the deployable members can be deployed by actuating the inner actuation member, such as by rotating the inner actuating member, which may include one or more camming surfaces. The deployed member (e.g., 4804) are configured, once deployed, to aid in preventing joint rotation, thereby increasing the stability of the joint. The elongate body 4804, which can include any features of any sleeve herein, can include one or more growth features (e.g., fenestrations, lattice sections) to facilitate one or more of bony on-growth, in-growth, or through-growth.

Implant 4800 is an example of an implant with an elongate implant body that includes one or more threads, optionally a plurality of regions having different number of leads.

Implant 4800 is an example of an implant with an elongate body (e.g. 4802) that includes a plurality of rows of openings (optionally linear rows), each of the rows including a plurality of openings separated by a portion of the elongate implant body.

Implant 4800 is an example of an implant with an elongate implant body that separates a plurality of openings, wherein the separating portion includes one or more threads.

Implant 4800 is an example of an implant with deployable members, wherein any of the deployable members include a plurality of protrusions extending from a spine, the protrusions extending further radially outward than the spine, and optionally the protrusions formed integrally with the spine.

Implant 4800 is an example of an implant with one or more deployable members that are positioned relative to an elongate implant body 4802 such that they are deployed upon actuation of an internal deployment member.

Implant 4800 is an example of an implant wherein an internal deployment member comprises a plurality of radially protruding camming surfaces that when rotated cause one or more deployable members to move radially outward.

Implant 4800 is an example of an implant with one or more threads on an elongate implant body, wherein the threads provide a mechanical radial stop to one or more deployable members, optionally preventing the opening(s) from bowing under load.

Implant 4800 is an example of an implant with an implant body with openings that can be tapered to limit play between the elongate implant body and the one or more deployable members.

Implant 4800 is an example of an implant with an elongate implant body that can have one or more porous surfaces.

Implant 4800 is an example of an implant with a plurality of deployable members that can be actuated and deployed by an inner actuatable member.

Any of the composite implants herein can include a volume defined by an inner surface of the sleeve and an outer surface of the shank. That is, a gap can exist between the outer surface of the shank and the inner surface of the sleeve. The volume can facilitate bony ingrowth.

As set forth above, when the composite implants herein are advanced via a posterior sacral alar-iliac ("SAI") trajectory and disposed across an SI joint, it can be advantageous when certain regions of the implant are adjacent certain bone or tissue once fully implanted. As set forth above, the distal region of the implant is generally configured to be able to better anchor into relatively denser cortical bone, such as with a dual threaded distal region. With some of the composite implants above (e.g. FIG. 34A), the sleeve is tapered in a distal region and includes a dual threaded region. A central region of the sleeve proximal to the distal tapered region (which can be part of an implant growth region) may be single thread (e.g. FIG. 34A), and can have one or more growth features configured to better facilitate at least one of bony on-growth, in-growth, or through-growth than the distal anchoring region. For example, in several examples herein (e.g. FIGS. 34-47), the central growth region includes at least one of one or more fenestrations or one or more lattice sections, examples of each are provided herein. Some sleeves herein can optionally also include a dual-lead proximal end region, such as in FIG. 31, 33C, 34A, 36A, 41A, 44A, which can better configure the composite implant proximal region to anchor into the more dense cortex of the sacrum. In some embodiments, the sleeve may have a central region with a single lead, a proximal region with a multi-lead (e.g. dual), and optionally a distal region that is multi-lead (e.g. dual lead).

In some methods of use, the implants herein (e.g. the composite implants) as delivered with a posterior sacral alar-iliac ("SAI") trajectory. Without intending to be limiting, there can be benefits to implanting any of the composite implants herein such that at least 15 mm of the implant extends distal to the SI joint in the final implanted position. In some methods of use the implants extend at least 15 mm-20 mm beyond the SI joint. The distal anchoring region thus can have lengths that facilitate a distal anchoring region of the implant extending at least 15 mm beyond the joint. This can help ensure the implant distal anchoring region extends into the dense cortical ilium bone and helps anchor the implant.

Any of the sleeves herein include an inner lumen, the inner lumen sized and configured to receive at least a portion of an inner member (e.g. inner shank).

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of assembling a composite bone implant prior to implantation within a patient, the method comprising:
    positioning a monolithic elongate shank within a sleeve such that the sleeve is disposed over at least a central portion of the shank,
        wherein the positioning step positions a growth region of the sleeve in a central region of the composite implant, the growth region comprising a plurality of lattice sections spaced apart and extending about the sleeve, and a plurality of fenestrations spaced apart and extending about the sleeve and through the sleeve, and
        wherein the plurality of fenestrations each have a size that is larger than pore sizes of the plurality of lattice sections.

2. The method of claim 1, wherein the positioning step comprises rotating at least one of the monolithic shank or the sleeve.

3. The method of claim 2, wherein rotating further comprising interfacing a sleeve inner thread and a shank outer thread to thereby resist axial motion between the shank and the sleeve at the location of the interface.

4. The method of claim 1, wherein the positioning step leaves exposed a distal threaded region of the monolithic shank.

5. The method of claim 1, wherein the positioning step creates a thread continuity between a shank outer thread and a sleeve outer thread at the distal end of the sleeve.

6. The method of claim 1, wherein the positioning step exposes a smoother shank surface through the plurality of fenestrations.

7. The method of claim 1, further comprising positioning the assembled composite implant in a packaging.

8. The method of claim 1, wherein the positioning step creates a composite implant distal anchoring region that is distal to the growth region, the distal anchoring region having one or more distal surface features that better adapt the distal anchoring region for anchoring into iliac bone than the growth region, and the growth region having one or more growth features that better adapt the growth region to facilitate at least one of bony on-growth, in-growth, or through-growth than the anchoring region.

9. A method, comprising:
    assembling a composite bone implant prior to implantation within a patient, the composite bone implant including a monolithic elongate shank and a sleeve that are both sized, configured and arranged to be coupled together to form the composite implant and remain implanted in the patient following implantation, wherein the assembling step comprises,
        rotationally moving one or both of the monolithic elongate shank and the sleeve relative to the other to position the monolithic elongate shank within the sleeve such that a sleeve inner thread and a shank outer thread interface and thereby resist axial motion between the shank and the sleeve at the location of the interface and such that the sleeve is disposed over at least a central portion of the shank, wherein rotationally moving one or both of the monolithic elongate shank and the sleeve relative to the other positions a shank distal thread distal to a distal end of the sleeve,
        wherein, once assembled, the composite implant has a central region that includes a growth region of the sleeve, the growth region of the sleeve comprising at least one thread, a plurality of lattice structures, and a plurality of fenestrations through the sleeve, wherein the plurality of lattice structures and the plurality of fenestrations are disposed axially between the at least one thread in the growth region of the sleeve.

10. The method of claim 9, wherein the rotationally moving step creates an outer implant thread continuity between a shank outer thread and a sleeve outer thread at the distal end of the sleeve.

11. A method, comprising:
    assembling a composite bone implant prior to implantation within a patient, the composite bone implant including a monolithic elongate shank and a sleeve that are both sized, configured and arranged to be coupled together to form the composite implant and remain implanted in the patient following implantation, wherein the assembling step comprises,
        rotationally moving one or both of the monolithic elongate shank and the sleeve relative to the other to position the monolithic elongate shank within the sleeve such that a sleeve inner thread and a shank outer thread interface and such that the sleeve is disposed over at least a central portion of the shank, wherein rotationally moving one or both of the monolithic elongate shank and the sleeve relative to the other positions a shank distal thread distal to a distal end of the sleeve,
        wherein, once assembled, the composite implant has a growth region of the sleeve in a central region of the composite implant, the growth region of the sleeve comprising at least one thread, a plurality of lattice structures, and a plurality of fenestrations through the sleeve, wherein the plurality of fenestrations are axially between the at least one thread in the growth region of the sleeve.

12. The method of claim 9, further comprising positioning the assembled composite implant in a packaging.

* * * * *